United States Patent
Fern et al.

(10) Patent No.: US 10,689,311 B2
(45) Date of Patent: Jun. 23, 2020

(54) REDUCED POLYMER FORMATION FOR SELECTIVE ETHYLENE OLIGOMERIZATIONS

(71) Applicant: Chevron Phillips Chemical Company LP, The Woodlands, TX (US)

(72) Inventors: Jared T. Fern, Kingwood, TX (US); Orson L. Sydora, Houston, TX (US); Uriah J. Kilgore, Kingwood, TX (US); Steven M. Bischof, Humble, TX (US); Eric R. Fernandez, Houston, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 16/408,110

(22) Filed: May 9, 2019

(65) Prior Publication Data

US 2019/0263733 A1    Aug. 29, 2019

Related U.S. Application Data

(62) Division of application No. 15/167,009, filed on May 27, 2016, now Pat. No. 10,329,212.

(51) Int. Cl.
*C07C 2/36*     (2006.01)
*C07F 9/46*     (2006.01)
(Continued)

(52) U.S. Cl.
CPC ............... *C07C 2/36* (2013.01); *B01J 31/24* (2013.01); *C07F 9/46* (2013.01); *C07F 9/6561* (2013.01);
(Continued)

(58) Field of Classification Search
CPC ... C07C 2/36; C07C 2531/14; C07C 2531/34; C07C 2531/24; C07C 2/32; C07C 11/02;
(Continued)

(56) References Cited

U.S. PATENT DOCUMENTS

| | | |
|---|---|---|
| 3,361,525 A | 1/1968 | Rycke et al. |
| 4,538,018 A | 8/1985 | Carter |

(Continued)

FOREIGN PATENT DOCUMENTS

| | | |
|---|---|---|
| CN | 1490291 A | 4/2004 |
| DE | 1146892 B | 4/1963 |

(Continued)

OTHER PUBLICATIONS

Notice of Allowance dated Feb. 14, 2019 (9 pages), U.S. Appl. No. 15/167,009, filed May 27, 2016.
(Continued)

*Primary Examiner* — Ali Z Fadhel
(74) *Attorney, Agent, or Firm* — Conley Rose, P.C.

(57) ABSTRACT

Disclosed are processes, systems, and reaction systems for the oligomerization of ethylene to form an ethylene oligomer product in a reaction zone using a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane. A $C_{3+}$ olefin can be present in the reaction zone for a period of time, where the $C_{3+}$ olefin is not an ethylene oligomer formed in-situ within the reaction zone.

26 Claims, 4 Drawing Sheets

(51) Int. Cl.
*C07F 9/6561* (2006.01)
*C07F 11/00* (2006.01)
*B01J 31/24* (2006.01)

(52) U.S. Cl.
CPC ........ *C07F 11/005* (2013.01); *C07C 2531/14* (2013.01); *C07C 2531/24* (2013.01); *C07C 2531/34* (2013.01); *Y02P 20/52* (2015.11)

(58) Field of Classification Search
CPC .......... C07C 11/04; C07C 11/107; C07F 9/46; C07F 9/6561; C07F 11/005; B01J 31/24; B01J 8/02; B01J 31/143; B01J 31/22; B01J 2531/60; Y02P 20/52
See application file for complete search history.

(56) References Cited

U.S. PATENT DOCUMENTS

| | | | |
|---|---|---|---|
| 5,217,703 | A | 6/1993 | Goodson |
| 7,276,566 | B2 | 10/2007 | Muruganandam et al. |
| 7,300,904 | B2 | 11/2007 | Dixon et al. |
| 7,361,623 | B2 | 4/2008 | Dixon et al. |
| 7,554,001 | B2 | 6/2009 | Dixon et al. |
| 7,994,363 | B2 | 8/2011 | Gao et al. |
| 8,252,956 | B2 | 8/2012 | Gao et al. |
| 8,367,786 | B2 | 2/2013 | Dixon et al. |
| 8,680,003 | B2 | 3/2014 | Sydora et al. |
| 8,865,610 | B2 | 10/2014 | Sydora et al. |
| 9,283,555 | B2 | 3/2016 | Sydora et al. |
| 9,707,549 | B1 | 7/2017 | Kilgore et al. |
| 9,732,106 | B2 | 8/2017 | Sydora et al. |
| 10,183,960 | B1 | 1/2019 | Bischof et al. |
| 10,232,339 | B2 | 3/2019 | Bischof et al. |
| 2002/0182124 | A1 | 12/2002 | Woodard et al. |
| 2003/0195307 | A1 | 10/2003 | Kaji et al. |
| 2004/0008572 | A1 | 1/2004 | Stuart |
| 2004/0152935 | A1 | 8/2004 | Jones et al. |
| 2005/0002841 | A1 | 1/2005 | Moberg |
| 2006/0223960 | A1 | 10/2006 | Jaber et al. |
| 2006/0247399 | A1 | 11/2006 | McConville et al. |
| 2007/0185360 | A1 | 8/2007 | Buchanan et al. |
| 2008/0207973 | A1 | 8/2008 | Palmas et al. |
| 2010/0041841 | A1 | 2/2010 | Terry et al. |
| 2010/0222622 | A1 | 9/2010 | Overett et al. |
| 2010/0240847 | A1 | 9/2010 | Dixon et al. |
| 2010/0274065 | A1 | 10/2010 | Sydora |
| 2012/0142989 | A1 | 6/2012 | Jaber et al. |
| 2012/0309965 | A1* | 12/2012 | Sydora ...................... C07F 9/46 544/64 |
| 2013/0090508 | A1 | 4/2013 | Wang et al. |
| 2013/0331629 | A1* | 12/2013 | Sydora ................... B01J 31/189 585/523 |
| 2015/0152200 | A1 | 6/2015 | Hanton et al. |
| 2016/0375431 | A1 | 12/2016 | Carney et al. |
| 2017/0341998 | A1 | 11/2017 | Bischof et al. |
| 2017/0341999 | A1 | 11/2017 | Fern et al. |
| 2017/0342000 | A1 | 11/2017 | Bischof et al. |
| 2017/0342001 | A1 | 11/2017 | Fern et al. |
| 2017/0349505 | A1 | 12/2017 | Kilgore et al. |
| 2019/0091675 | A1 | 3/2019 | Bischof et al. |
| 2019/0092708 | A1 | 3/2019 | Bischof et al. |
| 2019/0092709 | A1 | 3/2019 | Bischof et al. |

FOREIGN PATENT DOCUMENTS

| | | |
|---|---|---|
| EP | 0780353 A1 | 6/1997 |
| EP | 2684857 A1 | 1/2014 |
| WO | 0204119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |
| WO | 2019067466 A1 | 4/2019 |

OTHER PUBLICATIONS

Foreign communication from a related counterpart application—International Search Report and Written Opinion, PCT/US2018/036068, dated Feb. 25, 2019, 15 pages.
Office Action dated Mar. 13, 2019 (58 pages), U.S. Appl. No. 16/262,164, filed Jan. 30, 2019.
Advisory Action dated May 1, 2019 (5 pages), U.S. Appl. No. 15/719,107, filed Sep. 28, 2017.
Notice of Allowance dated May 7, 2019 (8 pages), U.S. Appl. No. 15/167,024, filed May 7, 2019.
Notice of Allowance dated May 13, 2019 (13 pages), U.S. Appl. No. 15/166,991, filed May 27, 2016.
Agapie, Theodor, et al., "Mechanistic Studies of Olefin and Alkyne Trimerization with Chromium Catalysts: Deuterium Labeling and Studies of Regiochemistry Using a Model Chromacyclopentane Complex," J. Am. Chem. Soc., 2007, pp. 14281-14295, vol. 129, No. 46, American Chemical Society.
Bollmann, Annette, et al., "Ethylene Tetramerization: A New Route to Produce 1-Octene in Exceptionally High Selectivities," J. Am. Chem. Soc., 2004, pp. 14712-14713, vol. 126, No. 45, American Chemical Society.
Carter, Anthea, et al., "High activity ethylene trimerisation catalysts based on diphospine ligands," Chemical Communications, vol. 8, 2002, pp. 858-859 plus 2 pages Supplementary Information.
Group notation revised in periodic table, Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Sydora, Orson L., et al., "Selective Ethylene Tri-/Tetramerization Catalysts," ACS Catalysis, 2012, pp. 2452-2455, vol. 2, American Chemical Society.
Office Action dated Apr. 25, 2017 (21 pages), U.S. Appl. No. 15/166,991, filed May 27, 2016.
Office Action dated Jul. 24, 2017 (33 pages), U.S. Appl. No. 15/167,009, filed May 27, 2016.
Foreign communication from a related counterpart application—International Search Report and Written Opinion, PCT/US2017/033165, dated Aug. 3, 2017, 11 pages.
Foreign communication from a related counterpart application—International Search Report and Written Opinion, PCT/US2017/033168, dated Aug. 3, 2017, 8 pages.
Office Action dated Aug. 2, 2017 (36 pages), U.S. Appl. No. 15/167,024, filed May 27, 2016.
Foreign communication from a related counterpart application—International Search Report and Written Opinion, PCT/US2017/032191, dated Aug. 14, 2017, 15 pages.
Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.

(56) References Cited

OTHER PUBLICATIONS

Office Action dated Aug. 30, 2017 (28 pages), U.S. Appl. No. 15/167,017, filed May 27, 2016.
Foreign communication from a related counterpart application—International Search Report and Written Opinion, PCT/US2017/032199, dated Aug. 17, 2017, 14 pages.
Office Action (Final) dated Nov. 1, 2017 (40 pages), U.S. Appl. No. 15/166,991, filed May 27, 2017.
AkzoNobel Product Data Sheet MMAO-3A/Heptane Solutions, 2014, 2 pgs.
AkzoNobel Safety Data Sheet MMAO-3A 7 wt% Al in Heptane, 2016, 17 pgs.
AkzoNobel Product Data Sheet MMAO-20/Heptane Solutions, 2014, 2 pgs.
AkzoNobel Safety Data Sheet MMAO-20 11-30% in Heptane, 2007, 9 pgs.
Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186.
Bartlett, Stuart A., et al., "Activation of [CrCl3{R—SN(H)S—R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.
Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.
Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.
Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of Chemistry.
Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.
Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.
Hossain, Anwar, et al., "Spin-crossover in Chromium-catalyzed Ethylene Trimerization" Density Functional Theory Study, "Bulletin of the Korean Chemical Society, Sep. 2014," pp. 2835-2838, vol. 35, No. 9, Korea Chemical Society.
Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.
Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.
Van Rensburg, Werner Janse, et al., "A DFT Study toward the Mechanish of Chromium-Catalyzed Ethylene Trimerization," Organometallics, Feb. 17, 2004, pp. 1207-1222, vol. 23, No. 6, American Chemical Society.
Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.
Fawcett, F.S., et al., "Cyanogen Fluoride: Synthesis and Properties," Journal of the American Chemical Society, Jul. 5, 1964, pp. 2576-2579, vol. 86, No. 13, American Chemical Society.
Office Action (Final) dated Feb. 6, 2018 (43 pages), U.S. Appl. No. 15/167,009, filed May 27, 2016.
Office Action (Final) dated Feb. 6, 2018 (53 pages), U.S. Appl. No. 15/167,024, filed May 27, 2016.
Morse, J. G., et al., "Substituted Difluoro- and Dichlorophosphines," Inorganic Syntheses, 1967, pp. 147-156, vol. 10, McGraw-Hill Book Company, Inc.
Singh, Rajendra P., et al., "The first application of SelectfluorTM in electrophilic fluorination of amines: a new route to –NF2, -NHF, and >NF compounds," Chemical Communication, 2001, pp. 1196-1197, vol. 13, Royal Society of Chemistry.
Imhoff, Donald W., et al., "Characterization of Methylaluminoxanes and Determination of Trimethylaluminum Using Proton NMR," Organometallics, 1998, pp. 1941-1945, vol. 17, American Chemical Society.
Office Action (Final) dated Feb. 28, 2018 (43 pages), U.S. Appl. No. 15/167,017, filed May 27, 2016.
Office Action dated Jun. 25, 2018 (43 pages), U.S. Appl. No. 15/719,107, filed Sep. 28, 2017.
Office Action dated Jun. 28, 2018 (24 pages), U.S. Appl. No. 15/166,991, filed May 27, 2016.
Office Action dated Jul. 27, 2018 (24 pages), U.S. Appl. No. 15/167,017, filed May 27, 2016.
Office Action dated Aug. 2, 2018 (19 pages), U.S. Appl. No. 15/167,024, filed May 27, 2016.
Office Action dated Sep. 18, 2018 (31 pages), U.S. Appl. No. 15/712,295, filed Sep. 22, 2017.
Office Action dated Oct. 1, 2018 (26 pages), U.S. Appl. No. 15/167,009, filed May 27, 2016.
Foreign communication from a related counterpart application—International Search Report and Written Opinion, PCT/US2018/052709, dated Jan. 11, 2019, 12 pages.
Office Action (Final) dated Jan. 23, 2019 (25 pages), U.S. Appl. No. 15/166,991, filed May 27, 2016.
Office Action (Final) dated Jan. 23, 2019 (16 pages), U.S. Appl. No. 15/719,107, filed Sep. 28, 2017.
Notice of Allowance dated Jan. 29, 2019 (7 pages), U.S. Appl. No. 15/712,295, filed Sep. 22, 2017.
Office Action (Final) dated Feb. 13, 2019 (17 pages), U.S. Appl. No. 15/167,024, filed May 27, 2016.

* cited by examiner

REDUCED POLYMER FORMATION FOR SELECTIVE ETHYLENE OLIGOMERIZATIONS

CROSS-REFERENCE TO RELATED APPLICATIONS

This application is a divisional of and claims priority to U.S. patent application Ser. No. 15/167,009 filed May 27, 2016, published as U.S. Patent Application Publication US 2017/0342001 A1, and entitled "Reduced Polymer Formation for Selective Ethylene Oligomerizations," which is incorporated by reference herein in its entirety.

TECHNICAL FIELD

The present disclosure relates to processes, systems and/or reaction systems configurations for the selective oligomerization of ethylene.

BACKGROUND

The development of alpha olefin oligomerization techniques for the selective production of linear alpha olefins ($C_6$ to $C_{20}$) which do not utilize triethylaluminum (TEA) as part of the catalyst system has been a challenge. Both the economics and relative efficiency of TEA-based techniques have been difficult to match in alternative techniques. Some commercial success has been achieved using alternative techniques which use homogeneous catalyst systems; however, these techniques require extended secondary processing to recover the linear alpha olefins from undesired fractions/products such as butene or waxes. Other alternative catalyst systems have been developed for selective ethylene oligomerization. The selective ethylene oligomerization catalyst systems can produce desired linear alpha olefins without the drawbacks of the alternative techniques which use homogeneous catalyst systems. There is an ongoing need for improvements to selective ethylene oligomerization techniques.

SUMMARY

Disclosed herein is a process comprising: a) introducing into a reaction zone containing a $C_3$ olefin (any disclosed herein) and optionally an organic reaction medium (any disclosed herein) wherein the reaction zone is substantially devoid of ethylene, i) ethylene ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iii) the organic reaction medium, and iv) optionally hydrogen; and b) forming an ethylene oligomer product in the reaction zone; wherein the $C_3$ olefin is not an ethylene oligomer formed in-situ within the reaction zone.

Also disclosed herein is a process comprising: a) contacting in a reaction zone i) a $C_{3+}$ olefin (e.g., any disclosed herein), ii) ethylene, iii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iv) an organic reaction medium (any disclosed herein), and v) optionally hydrogen into the reaction zone; and c) forming an ethylene oligomer product; wherein the $C_{3+}$ olefin is not an ethylene oligomer formed in-situ within the reaction zone.

Also disclosed herein is a process comprising: a) contacting i) ethylene, ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iii) an organic reaction medium (any described herein), and iv) optionally hydrogen in a reaction zone; b) forming an ethylene oligomer product in the reaction zone; wherein ethylene, the catalyst system, and the organic reaction medium are introduced into the reaction zone and for a period of time a $C_{3+}$ olefin is introduced into the reaction zone.

Also disclosed herein is a process comprising: a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); b) for a period of time separately feeding to the reaction zone a feedstock mixture comprising ethylene and i) a $C_{3+}$ olefin (e.g., any described herein), and ii) at least a portion of an organic reaction medium (e.g., any described herein), or iii) combinations of i) and ii); wherein the feedstock mixture is substantially free of the catalyst system; c) contacting the catalyst system and the feedstock mixture in the reaction zone; and d) forming an ethylene oligomer product in the reaction zone.

Also disclosed herein is a process comprising: a) contacting i) ethylene, ii) at least a portion of an organic reaction medium (e.g., any disclosed herein), and iii) for a period of time a $C_{3+}$ olefin (e.g., any disclosed herein) to form a feedstock mixture; b) subsequent to a), contacting in a reaction zone the feedstock mixture with a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) forming an ethylene oligomer product in the reaction zone.

Also disclosed herein is a process comprising: a) diluting ethylene by an addition of at least a portion of an organic reaction medium (any described herein), for a period of time a $C_{3+}$ olefin (e.g., any described herein), or for a period of time at least a portion of an organic reaction medium (any described herein) and a $C_{3+}$ olefin to form a feedstock mixture prior to contacting the ethylene with a catalyst system in a reaction zone; b) contacting in the reaction zone the feedstock mixture and the catalyst system, wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) forming an ethylene oligomer product in the reaction zone.

Also disclosed herein is a system comprising: a) a feedstock mixture comprising ethylene, an organic reaction medium (e.g., any described herein), and for a period of time a $C_{3+}$ olefin (e.g., any described herein); b) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) a reaction zone receiving the feedstock mixture separately from the catalyst stream.

Also disclosed herein is a process comprising: a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); b) separately feeding to the reaction zone a feedstock mixture comprising i) ethylene, ii) an organic reaction medium (e.g., any described herein), and iii) a $C_{3+}$ olefin (e.g., any described herein) for a period of time to contact the catalyst system; wherein during a reaction zone startup the feedstock mixture $C_{3+}$ olefin:ethylene weight ratio periodically or continuously decreases; c) forming an ethylene oligomer product in the reaction zone; and d) operating the reaction zone in about steady-state conditions subsequent to the reaction zone start-up; wherein the period of time is a reaction zone period of time or a $C_{3+}$ olefin/ethylene feed period of time.

Also disclosed herein is a process for startup of a reaction zone, the process comprising: contacting in the reaction zone 1) ethylene, 2) a catalyst system comprising a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and b) an aluminoxane (any disclosed herein), 3) an organic reaction medium, and 4) optionally hydrogen to form an ethylene oligomer product; wherein: the catalyst system is fed to the reaction zone, a feedstock mixture comprising i) ethylene, ii) an organic reaction medium (any described herein), and iii) for a period of time a $C_{3+}$ olefin (any described herein) is fed to the reaction zone, wherein the feedstock mixture is substantially free of the catalyst system prior to contact in the reaction zone.

Also disclosed herein is a reaction system comprising: a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein) to the reaction zone; a second reaction zone inlet configured to introduce ethylene, an organic reaction medium, and optionally hydrogen to the reaction zone; a $C_{3+}$ olefin feed line in fluid communication with the first reaction zone inlet, the second reaction zone inlet, or a third reaction zone inlet configured to introduce a $C_{3+}$ olefin to the reaction zone; and one or more reaction zone outlets configured to discharge the reaction zone effluent comprising an ethylene oligomer product from the reaction zone.

Also disclosed herein is a reaction system comprising: a reaction zone; a reaction zone inlet configured to introduce a catalyst system, ethylene, an organic reaction medium, and a $C_{3+}$ olefin to the reaction zone; an ethylene feed line comprising ethylene, a $C_{3+}$ olefin feed line comprising a $C_{3+}$ olefin, an organic reaction medium feed line comprising an organic reaction medium and optionally a hydrogen feedline comprising hydrogen all in fluid communication with the reaction zone inlet, wherein the organic reaction medium feed line combines with the ethylene feed line to form a feedstock mixture feed line in fluid communication with the reaction zone inlet; a catalyst system feed line comprising the catalyst system in fluid communication with the reaction zone inlet, wherein the catalyst system feed line combines with the ethylene feed line, the organic reaction medium feed line, the feedstock mixture feed line, or a dispersed feedstock mixture feed line formed by passing the feedstock mixture through a mixing device; one or more reaction zone outlets configured to discharge the reaction zone effluent comprising an ethylene oligomer product from the reaction zone, wherein the catalyst system comprises (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), and wherein the $C_{3+}$ olefin feed line joins with one or more of the ethylene feed line, the organic reaction medium feed line, the feedstock mixture feed line, the dispersed feedstock mixture feed line, or a combined feed line formed by joining the catalyst system feed line and the dispersed feedstock mixture feed line.

Also disclosed herein is a reaction system comprising: a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein) to the reaction zone; a second reaction zone inlet configured to introduce ethylene and optionally hydrogen to the reaction zone; a third reaction zone inlet configured to introduce an organic reaction medium to the reaction zone; a $C_{3+}$ olefin feed line in fluid communication with one or more of the first reaction zone inlet, the second reaction zone inlet, the third reaction zone inlet, or a fourth reaction zone inlet which is configured to introduce the $C_{3+}$ olefin directly to the reaction zone; and one or more reaction zone outlets configured to discharge the reaction zone effluent comprising an ethylene oligomer product from the reaction zone.

BRIEF DESCRIPTION OF THE DRAWINGS

For a detailed description, reference will now be made to the accompanying drawings.

DETAILED DESCRIPTION

Figure 1:
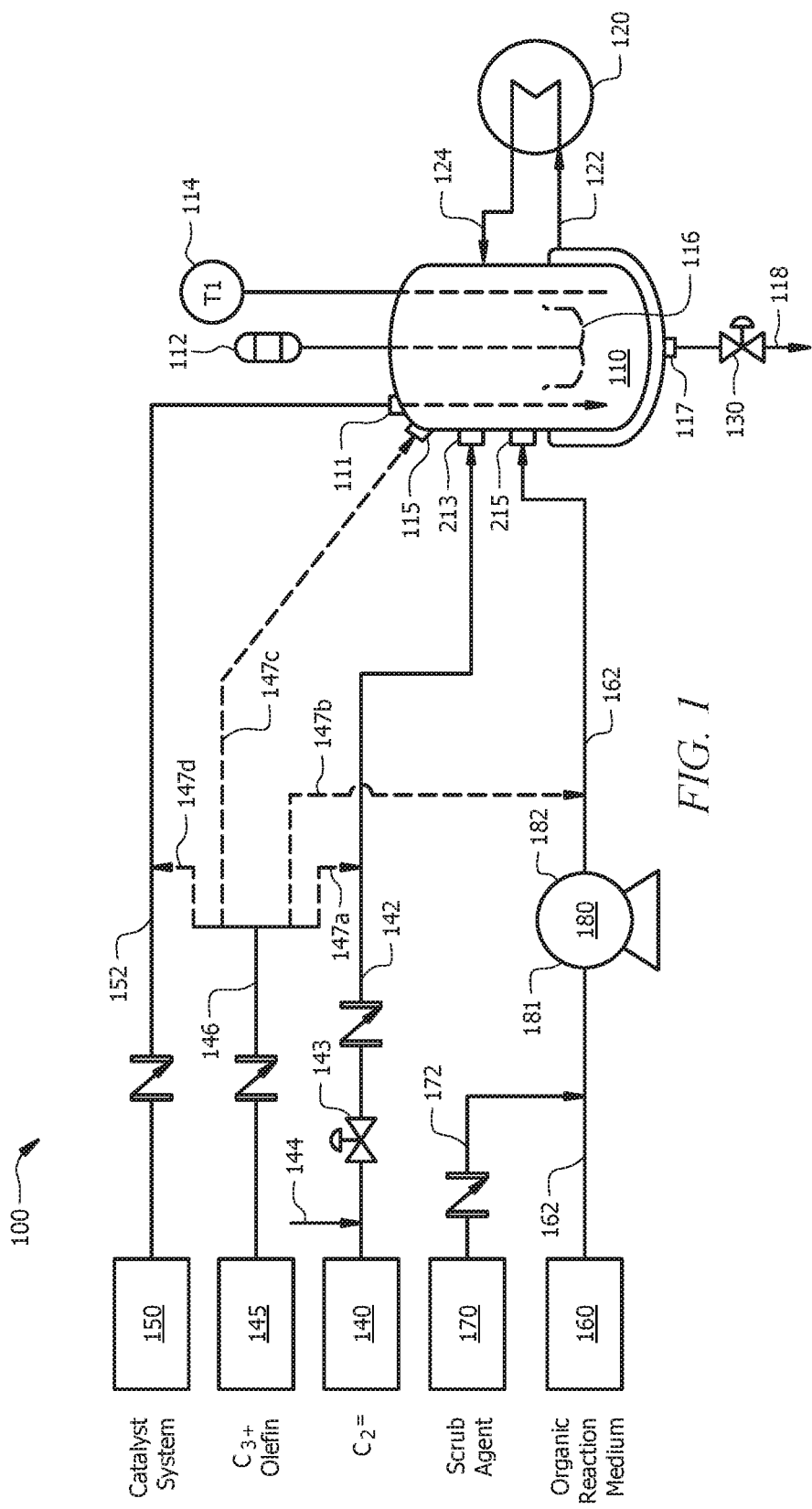
FIG. 1 shows a process flow diagram of another reaction system according to the present disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of material A. When a claim includes different features and/or feature classes (for example, a method step, feedstock features, and/or product features, among other possibilities), the transitional terms comprising, consisting essentially of, and consisting of apply only to the feature class that is utilized and it is possible to have different transitional terms or phrases utilized with different features within a claim. For example a method can comprise several recited steps (and other non-recited steps) but utilize a catalyst system preparation consisting of specific steps can utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News,* 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group in a $N^2$-phosphinyl amidine can be an inert functional group because a single metal compound cannot complex with both the para ether group and the $N^2$-phosphinyl amidine group in a single metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction zone effluent," and it derivatives generally refers to all materials which exit the reaction zone through a reaction zone outlet which discharges a reaction mixture and can include reaction system feed(s) (e.g., ethylene, catalyst system or catalyst system components, and/or organic reaction medium), and/or reaction product(s) (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction system through the reaction zone outlet/discharge, a reaction zone oligomer product effluent refers to only the oligomer product within the reaction zone effluent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Processes, systems, and/or reaction systems described herein can utilize steps, features, compounds, and/or equipment which are independently described herein. The process and/or methods described herein may or may not utilize step identifiers (e.g., 1), 2), etc., a), b), etc., i), ii), etc., or first, second etc., among others), feature identifiers (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes, systems, and/or reaction systems described herein can have multiple steps, features (e.g. reagent ratios, formation conditions, among other considerations), and/or multiple compounds and/or composition using no descriptor or sometimes having the same general identifier. Consequently, it should be noted that the processes, systems, and/or reaction systems described herein can be modified to use an appropriate step or feature identifier (e.g., 1), 2), etc., a), b), etc., i), ii), etc., or first, second etc., among others), feature identifier (e.g., 1), 2), etc., a), b), etc., i), ii), etc., or first, second etc., among others), and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the process, systems, and/or reaction systems without detracting from the general disclosure.

Processes, systems, and/or reaction systems for forming ethylene oligomer products are described herein. Such processes generally comprise contacting ethylene and a catalyst system to form an ethylene oligomer product under oligomerization conditions. As used herein, the term "oligomerization" and its derivatives, refers to processes which produce a mixture of products containing at least 70 weight percent products containing from 2 to 30 ethylene units. Similarly, as used herein, an "ethylene oligomer" is a product that contains from 2 to 30 ethylene units while an "ethylene oligomer product" includes all products made by the process including the "ethylene oligomers" and products which are not "ethylene oligomers" (e.g., products which contain more than 30 monomer units). Further the terms "ethylene oligomer product" and "ethylene oligomerization product" can be used interchangeably.

As used herein, the term "trimerization," and it derivatives, refers to a process which produces a mixture of products containing at least 70 weight percent products containing three and only three ethylene units. As used herein a "trimer" is a product which contains three and only three ethylene units while a "trimerization product" includes all products made by the trimerization process including trimer and product which are not trimers (e.g. dimers or tetramers). Generally, a "trimerization" process using ethylene produces an oligomer product containing at least 70 weight percent hexene(s).

As used herein, the term "tetramerization," and its derivatives, refers to a process which produces a mixture of products containing at least 70 weight percent products containing four and only four ethylene units. As used herein a "tetramer" is a product which contains four and only four ethylene units while a "tetramerization product" includes all products made by the tetramerization process including tetramer and products which are not tetramers (e.g. dimers or trimer). Generally, a "tetramerization" process using ethylene produces an oligomer product containing at least 70 weight percent octene(s).

As used herein, the term "trimerization and tetramerization," and it derivatives, refers to a process which produces an oligomer product containing at least 70 weight percent products containing three and/or four and only three and/or four ethylene units. As used herein a "trimerization and tetramerization product" includes all products made by the "trimerization and tetramerization" process including trimer, tetramer, and products which are not trimers or tetramers (e.g. dimers). Generally, a "trimerization and tetramerization" process using ethylene produces an oligomer product containing at least 70 weight percent hexene(s) and/or octene(s).

As used herein, mass and weight in any form (e.g., mass or weight, mass ratio or weight ratio) can be used interchangeably.

As used herein, the phrases "the $C_{3+}$ olefin is not an ethylene oligomer formed in-situ within the reaction zone," "the $C_{3+}$ olefin and the $C_{3+}$ olefin of the reaction zone C3+ olefin:ethylene weight ratio is not an ethylene oligomer formed in-situ within the reaction zone," "the $C_{3+}$ olefin of the reaction zone and/or the $C_{3+}$ olefin of the C3+ olefin:ethylene weight ratio is not an ethylene oligomer formed in-situ within the reaction zone," and similar terms used herein, refer to the $C_{3+}$ olefin which is used in particular aspects and embodiments disclosed herein. In particular, these phrases specifically indicate that the $C_{3+}$ olefin to which they refer is not an ethylene oligomer formed in-situ within the reaction zone. That is to say that while the $C_{3+}$ olefin to which they refer can have the identity of an ethylene oligomer that is formed in the reaction zone, the $C_{3+}$ olefin to which they refer was not formed in the reaction as a consequence of the oligomerization reaction the is occurring in the reaction zone. For example, an olefin comprising 1-hexene and/or 1-octene can be added to the reaction which is producing 1-hexene and/or 1-octene, however, since the 1-hexene and/or 1-octene was added to the reaction, it is not an ethylene oligomer produced in-situ within the reaction zone and thus would be considered in the noted phrases while the 1-hexene and/or 1-octene produce in-situ within the reaction zone would not be not considered in the noted phrases.

Various aspects and embodiments described herein may refer to a substituted group or compound. In an embodiment, each substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy group can be a $C_1$ to $C_{10}$ hydrocarboxy group; or alternatively, a $C_1$ to $C_5$ hydrocarboxy group.

In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

Aspects disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

Disclosed herein are processes, systems, and/or reaction systems for the oligomerization of ethylene to form an ethylene oligomer product comprising normal linear alpha olefins (NAO). In particular, processes, systems, and/or reaction systems described herein can selectively trimerize, tetramerize, or trimerize and tetramerize ethylene to produce an ethylene oligomer product containing hexenes (e.g., 1-hexene) and/or octenes (e.g., 1-octene). It has been unexpectedly found that the selective ethylene oligomerization processes, systems, and/or reaction systems using the catalyst systems disclosed herein are sensitive to specific reactor feed conditions. It has been unexpectedly found that large amounts of polymer can form during the startup of the reaction zone of a selective ethylene oligomerization. This polymer formation decreases as reaction zone on-stream time increases. Particularly, and while not wishing to be bound by theory, it is believed that that in the absence of a significant amount of $C_{3+}$ olefin, the catalyst systems disclosed herein have a greater propensity to produce polymer. Consequently, during a reaction zone startup catalyst system produces a large amount of polymer when very little $C_{3+}$ olefin is present. It has been discovered that the presence of a $C_{3+}$ olefin during the initial phase of selective ethylene oligomerization (e.g., during the start of a selective ethylene oligomerization reaction zone) can reduce that amount of polymer formed and can lead to the improved operation of processes, systems, and/or reaction systems for selective ethylene oligomerizations. It has also believed, without being limited to theory, that polymer can form with use of the herein disclosed selective oligomerization catalyst systems when concentrated portions of ethylene are contacted with a catalyst system. Thus, the contacting of a high concentration of ethylene with the selective ethylene oligomerization catalyst system can be another situation which can make polymer plugging and/or fouling of reaction zone components a limiting factor in oligomer production. In this latter situation, it has been discovered that contacting (or diluting) the ethylene with an organic reaction medium prior to contacting ethylene with the catalyst system can reduce polymer formation when compared to contacting a high concentration of ethylene with the catalyst system and provide improved operation of processes, systems, and/or reaction systems. Further it has be found that 1) the presence of a $C_{3+}$ olefin during the initial phase of selective ethylene oligomerization and 2) the contacting (or diluting) the ethylene with organic reaction medium prior to the contact of the ethylene with the catalyst systems either during the initial phase of the selective ethylene oligomerization, after the initial phase of the selective ethylene oligomerization, or both can lead to improved operation of processes, systems, and/or reaction systems for selective ethylene oligomerizations. The disclosed processes, systems, and/or reaction systems can 1) reduce the amount of polymer formed during startup of a selective ethylene oligomerization reaction, 2) reduce the amount of polymer formed during normal operation of a selective ethylene oligomerization reaction, and/or 3) increase hexenes and/or octenes productivity and/or production, and thus avoid fouling and/or plugging of the reaction zone and/or reaction system components.

The disclosed processes, systems, and reaction systems (e.g., those illustrated in FIGS. 1 to 3) can comprise a) contacting i) ethylene, ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane, iii) an organic reaction medium, and iv) optionally hydrogen; and b) forming an ethylene oligomer product in a reaction zone. In an embodiment, a $C_3$ olefin can be present in the reaction zone of the disclosed processes, systems, and reaction systems for a period of time, where the $C_{3+}$ olefin is not an ethylene oligomer formed in-situ within the reaction zone. In a combinable embodiment of the processes, systems, and/or reaction systems disclosed herein, the reaction zone can have a $C_{3+}$ olefin:ethylene weight ratio that over a period of time decreases from at least an initial value (any disclosed herein) to less than a final value (any disclosed herein). In an embodiment of the processes, systems, and/or reaction systems disclosed herein, the period of time can be initiated at a point in time when the reaction zone is not producing ethylene oligomer product and/or when the flow rate of ethylene is zero.

A disclosed process can comprise a) introducing into a reaction zone containing a $C_{3+}$ olefin and optionally an organic reaction medium wherein the reaction zone can be substantially devoid of ethylene; i) ethylene ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane, iii) the organic reaction medium, and iv) optionally hydrogen; and b) forming an ethylene oligomer product in the reaction zone. In an embodiment of this process, the $C_{3+}$ olefin is not an ethylene oligomer formed in-situ within the reaction zone. In a combinable embodiment of this process, the reaction zone can have a $C_{3+}$ olefin:ethylene weight ratio that over a period of time decreases from at least an initial value (any disclosed herein) to less than a final value (any disclosed herein).

A disclosed process or system can comprise a) contacting in a reaction zone i) a $C_3$ olefin, ii) ethylene, iii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane, iv) the organic reaction medium, and v) optionally hydrogen into the reaction zone; and c) forming an ethylene oligomer product. Another disclosed process can comprise a) contacting i) ethylene, ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane, iii) an organic reaction medium, and iv) optionally hydrogen in a reaction zone; b) forming an ethylene oligomer product in the reaction zone; wherein ethylene, the catalyst system, and the organic reaction medium are introduced into the reaction zone and for a period of time a $C_{3+}$ olefin is introduced into the reaction zone. In an embodiment, ethylene, the organic reaction medium, and for the period of time the $C_{3+}$ olefin can be separately introduced into the reaction zone; alternatively, ethylene and at least a portion of the organic reaction medium can be contacted to form a feedstock mixture prior to the ethylene contacting the catalyst system and the feedstock mixture can be introduced into the reaction zone, and for the period of time the $C_{3+}$ olefin can be separately introduced to the reaction zone; or alternatively, ethylene, at least a portion of the organic reaction medium, and for the period of time the $C_{3+}$ olefin can be contacted to form a feedstock mixture prior to the ethylene contacting the catalyst system and the feedstock mixture introduced into the reaction zone. When the ethylene and the $C_{3+}$ olefin are separately introduced into the reaction zone, the processes can further comprise introducing the $C_{3+}$ olefin to the reaction zone prior to introducing the ethylene, the catalyst system, or both the ethylene and the catalyst system to the reaction zone. In an embodiment, the reaction zone can have a $C_3$ olefin:ethylene weight ratio that over a period of time decreases from at least an initial value (any disclosed herein) to less than a final value (any disclosed herein) and wherein the $C_{3+}$ olefin and the $C_{3+}$ olefin of the reaction zone $C_{3+}$ olefin:ethylene weight ratio is not an ethylene oligomer formed in-situ within the reaction zone.

A disclosed process can comprise a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; b) for a period of time separately feeding to the reaction zone a feedstock mixture comprising ethylene and i) a $C_{3+}$ olefin, and ii) at least a portion of an organic reaction medium, or iii) combinations of i) and ii); wherein the feedstock mixture is substantially free of the catalyst system; c) contacting the catalyst system and the feedstock mixture in the reaction zone; and d) forming an ethylene oligomer product in the reaction zone. Another disclosed process can comprise a) contacting i) ethylene, at least a portion of an organic reaction medium, and for a period of time a $C_{3+}$ olefin to form a feedstock mixture; b) subsequent to a), contacting in a reaction zone the feedstock mixture with a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) forming an ethylene oligomer product in the reaction zone. A further disclosed process can comprise a) diluting ethylene by an addition of i) at least a portion of an organic reaction medium, ii) for a period of time a $C_{3+}$ olefin, or iii) for a period of time at least a portion of an organic reaction medium and $C_{3+}$ olefin to form a feedstock mixture prior to contacting the ethylene with a catalyst system in a reaction zone; b) contacting in the reaction zone the feedstock mixture and the catalyst system, wherein the catalyst system comprises i) a chromium component comprising a chromium compound, ii) a heteroatomic ligand, and iii) an aluminoxane (alternatively, a catalyst system comprising i) a chromium component comprising a heteroatomic ligand chromium compound complex, and ii) an aluminoxane); and c) forming an ethylene oligomer product in the reaction zone. A disclosed system can comprise: a) a feedstock mixture comprising ethylene, an organic reaction medium, and for a period of time a $C_{3+}$ olefin; b) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; and c) a reaction zone receiving the feedstock mixture separately from the catalyst stream. In an embodiment, the system can further comprise a reaction zone effluent line comprising an ethylene oligomer product formed in the reaction zone. In some embodiments of the processes and systems, 1) the $C_{3+}$ olefin can be dispersed in the feedstock mixture, for a period of time, prior to introducing/feeding the feedstock mixture into the reaction zone and/or 2) ethylene can be dispersed within the feedstock mixture prior to ethylene contacting the catalyst system. In another combinable embodiment of the processes and systems, ethylene can be dispersed within the feedstock mixture prior to introduction of the feedstock mixture into the reaction zone. In an embodiment of the processes and systems, the period of time can occur during a reaction zone startup.

A disclosed process can comprise a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane; b) separately feeding to the reaction zone a feedstock mixture comprising i) ethylene, ii) an organic reaction medium, and iii) for a period of time a $C_{3+}$ olefin to contact the catalyst system. In an embodiment, the period of time can occur during a reaction zone startup. Another disclosed process can be for a startup of a reaction zone, where the process can comprise contacting in the reaction zone 1) ethylene, 2) a catalyst system comprising a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and b) an aluminoxane, 3) an organic reaction medium, and 4) optionally hydrogen to form an ethylene oligomer product; wherein: the catalyst system can be introduced/fed to the reaction zone in a feedstock mixture comprising i) ethylene, ii) at least a portion of the organic reaction medium, and iii) for a period of time a $C_{3+}$ olefin is introduce/fed to the reaction zone, wherein the feedstock mixture is substantially free of the catalyst system prior to the feedstock mixture contacting the catalyst system in the reaction zone. In an embodiment of these processes, for the period of time the $C_{3+}$ olefin is part of the feedstock mixture introduced/fed to the reaction zone, the $C_{3+}$ olefin can be dispersed the feedstock mixture prior to introducing/feeding the feedstock mixture into the reaction zone and/or ethylene can be dispersed within the feedstock mixture prior to ethylene contacting the catalyst system.

A disclosed reaction system can comprise a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane to the reaction zone; a second reaction zone inlet configured to introduce ethylene, an organic reaction medium, and optionally hydrogen to the reaction zone; a $C_{3+}$ olefin feed line in fluid communication with the first reaction zone inlet, the second reaction zone inlet, or a third reaction zone inlet configured to introduce a $C_{3+}$ olefin to the reaction zone; and one or more reaction zone outlets configured to discharge the reaction zone effluent comprising an ethylene oligomer product from the reaction zone. In an embodiment, the reaction system can further comprise a catalyst system feed line flowing the catalyst system to the first reaction zone inlet; an ethylene feed line comprising the ethylene; an organic reaction medium feed line comprising the organic reaction medium, wherein the organic reaction medium feed line and the ethylene feed line can combine to yield the feedstock mixture which can introduced to the reaction zone via the second reaction zone inlet, wherein the $C_{3+}$ olefin feed line can combine with at least one of the catalyst system feed line, the ethylene feed line, the organic reaction medium feed line, the feedstock mixture feed line, or a dispersed feedstock mixture feed line formed by passing the feedstock mixture through a mixing device prior to flowing to the reaction zone via the second reaction zone inlet. In a combinable embodiment, the reaction system can further comprise a pump in fluid communication with the second reaction zone inlet and can be located upstream of a point where the ethylene feed line and the organic reaction medium feed line join to produce the feedstock mixture; and a mixing device positioned between i) the joining of the ethylene feed line and the organic reaction medium feed line and ii) the second reaction zone inlet to disperse the ethylene and the organic reaction medium prior to the feedstock mixture entering the reaction zone. In another combinable reaction system embodiment, during steady state operation the first reaction zone inlet can be configured to periodically or continuously introduce the catalyst system to the reaction zone, the second reaction zone inlet is configured to periodically or continuously introduced the feedstock mixture to the reaction zone, and the one or more reaction zone outlets can be configured to periodically or continuously discharge the reaction zone effluent from the reaction zone.

Another disclosed reaction system can comprise a reaction zone; a reaction zone inlet configured to introduce a catalyst system, ethylene, an organic reaction medium, and a $C_{3+}$ olefin to the reaction zone; an ethylene feed line comprising ethylene, a $C_{3+}$ olefin feed line comprising a $C_{3+}$ olefin, an organic reaction medium feed line comprising an organic reaction medium and optionally a hydrogen feedline comprising hydrogen all in fluid communication with the reaction zone inlet, wherein the organic reaction medium feed line can combine with the ethylene feed line to form a feedstock mixture feed line in fluid communication with the reaction zone inlet; a catalyst system feed line comprising the catalyst system in fluid communication with the reaction zone inlet, wherein the catalyst system feed line combines with the ethylene feed line, the organic reaction medium feed line, the feedstock mixture feed line, or a dispersed feedstock mixture feed line formed by passing the feedstock mixture feed line through a mixing device; one or more reaction zone outlets configured to discharge the reaction zone effluent comprising an ethylene oligomer product from the reaction zone, wherein the catalyst system comprises (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane, and wherein the $C_{3+}$ olefin feed line can join with one or more of the ethylene feed line, the organic reaction medium feed line, the feedstock mixture feed line, the dispersed feedstock mixture feed line, or a combined feed line formed by joining the catalyst system feed line and the dispersed feedstock mixture feed line. In an embodiment, the reaction system can further comprise a mixing device positioned between i) the joining of the ethylene feed line and the organic reaction medium feed line and ii) the reaction zone inlet to disperse the ethylene within the feedstock mixture prior to the feedstock mixture joining with the catalyst system and entering the reaction zone. In a combinable embodiment, the reaction zone inlet can be configured to periodically or continuously introduce the catalyst system and the feedstock mixture to the reaction zone, and the one or more reaction zone outlets can be configured to periodically or continuously discharge the reaction zone effluent from the reaction zone.

A further disclosed reaction system can comprise a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane to the reaction zone; a second reaction zone inlet configured to introduce ethylene and optionally hydrogen to the reaction zone; a third reaction zone inlet configured to introduce an organic reaction medium to the reaction zone; a $C_{3+}$ olefin feed line in fluid communication with one or more of the first reaction zone inlet, the second reaction zone inlet, the third reaction zone inlet, or a fourth reaction zone inlet which is configured to introduce the $C_{3+}$ olefin directly to the reaction zone; and one or more reaction zone outlets configured to discharge the reaction zone effluent comprising an ethylene oligomer product from the reaction zone. In an embodiment, the reaction system can further comprise a catalyst system feed line flowing the catalyst system to the first reaction zone inlet; an ethylene feed line flowing ethylene to the second reaction zone inlet; and an organic reaction medium feed line flowing the organic reaction medium to the third reaction zone inlet, wherein the $C_{3+}$ olefin feed line i) can combine with at least one of the catalyst system feed line, the ethylene feed line, or the organic reaction medium feed line, or ii) can flow directly to the fourth reaction zone inlet.

In an embodiment, the processes, systems, and/or reaction system disclosed herein can further comprise removing/withdrawing a reaction zone effluent comprising an ethylene oligomer product from the reaction zone. In an embodiment, the processes, systems, and/or reactions systems disclosed herein can be continuous processes, systems, and/or reaction systems wherein the feeds (e.g., ethylene, catalyst system or catalyst system components, organic reaction medium, $C_{3+}$ (where applicable in the processes, systems, and/or reaction systems), and any other feeds can be periodically or continuously introduced/fed to the reaction zone and a reaction zone effluent comprising the ethylene oligomer product can be periodically or continuously removed/withdrawn from the reaction zone.

In an embodiment of the processes, systems, and/or reaction system disclosed herein, the reaction zone can have a $C_{3+}$ olefin:ethylene weight ratio that over a period of time can decrease; or alternatively, have a $C_{3+}$ olefin:ethylene weight ratio fed/introduced to the reaction zone that over a period of time can decrease from at least an initial value (any disclosed herein) to less than a final value (any disclosed herein). Generally, the $C_{3+}$ olefin of the reaction zone and/or the $C_{3+}$ olefin of the $C_{3+}$ olefin:ethylene weight ratio are/is not an ethylene oligomer formed in-situ within the reaction zone. In a combinable embodiment, the applicable processes, systems, and/or reaction system disclosed herein can have ethylene and the $C_{3+}$ olefin fed/introduced to the reaction zone (either separately, together in a feedstock mixture, or both) wherein a $C_{3+}$ olefin:ethylene weight ratio fed/introduced to the reaction zone can decrease; or alternatively, decrease from at least an initial value to less than a final value over a period of time. In further combinable embodiment, the $C_{3+}$ olefin:ethylene weight ratio and/or the $C_{3+}$ olefin:ethylene weight ratio fed/introduced to the reaction zone can decrease in steps; or alternatively, can decrease periodically or continuously.

Generally, the catalyst system, the catalyst system components (e.g., the chromium component, the aluminoxane, among others), the organic reaction medium, the ethylene oligomer product, the conditions at which the ethylene oligomer product can be formed (or the reaction zone can operate), the $C_{3+}$ olefin, the reaction zone, a reaction zone $C_{3+}$ olefin:ethylene weight ratio, a reaction zone period of time, a feedstock mixture $C_{3+}$ olefin:ethylene weight ratio, a feedstock mixture period of time, an ethylene to organic reaction medium mass ratio, an (ethylene+$C_{3+}$ olefin) to organic reaction medium mass ratio, components of the reaction system, and any other features disclosed herein for the processes, systems, and/or reaction system disclosed herein are independently described herein. Additionally, further steps that can be utilized in the processes, systems, and/or reaction system are independently disclosed herein. These independent descriptions can be utilized without limitation, and in any combination, to further describe the processes, systems, and/or reaction systems disclosed herein. In particular these independent descriptions can be utilized without limitation, and in any combination, to further describe the processes, systems, and/or reaction systems where for a period of time a $C_{3+}$ olefin which is not an ethylene oligomer formed in-situ within the reaction zone, is present in the reaction zone.

During the reaction zone period of time a $C_{3+}$ olefin:ethylene weight ratio in the reaction zone can decrease from at least an initial value to less than a final value. In an embodiment, the reaction zone $C_{3+}$ olefin:ethylene weight ratio at least initial value independently can be any at least initial value disclosed herein, and the reaction zone $C_{3+}$ olefin:ethylene weight ratio less than final value independently can be any less than final value disclosed herein. In an embodiment, the reaction zone $C_{3+}$ olefin:ethylene weight ratio at least initial value can be a value of at least 0.5:1, 0.75:1, 1:1, 1.5:1, 2:1, 3:1, 5:1, 10:1, 25:1, 50:1, or 100:1. In an embodiment, the reaction zone $C_{3+}$ olefin:ethylene weight ratio less than final value can be a value less than 0.2:1, 0.15:1, 0.1:1, 0.08:1, 0.06:1, 0.04:1, 0.02:1, or 0.01:1. In an embodiment, the reaction zone $C_{3+}$ olefin:ethylene weight ratio can decrease from any reaction zone $C_{3+}$ olefin:ethylene weight ratio greater than initial value disclosed herein to any reaction zone $C_{3+}$ olefin:ethylene weight ratio less than final value disclosed herein. Thus, in some non-limiting embodiments, the reaction zone $C_{3+}$ olefin:ethylene weight ratio can decrease from at least 0.5:1 to less than 0.2:1, from at least 1:1 to less than 0.2:1, from at least 2:1 to less than 0.15:1, from at least 3:1 to less than 0.1:1, from at least 5:1 to less than 0.15:1, from at least 10:1 to less than 0.2:1, or from at least 100:1 to less than 0.1:1. Other embodiments, for which the reaction zone $C_{3+}$ olefin:ethylene weight ratio can decrease from a reaction zone $C_{3+}$ olefin:ethylene weight ratio initial value to a reaction zone $C_{3+}$ olefin:ethylene weight ratio final value are readily apparent to those skilled in the art with the aid of this disclosure. In an embodiment, the reaction zone period of time can begin when the reaction zone $C_{3+}$ olefin:ethylene weight ratio falls below the reaction zone $C_{3+}$ olefin:ethylene weight ratio greater than initial value. In an embodiment, the reaction zone period of time can end when the reaction zone $C_{3+}$ olefin:ethylene weight ratio falls below the less than final value. In an embodiment, the reaction zone period of time can begin when the reaction zone is not producing ethylene oligomer product and/or when the flow rate of ethylene to the reaction zone is zero. In an embodiment, the reaction zone period of time can encompass a time where the reaction zone $C_{3+}$ olefin:ethylene weight ratio decreases from about 1:0 to about 0:1. In an embodiment, the reaction zone period of time represents the startup of the reaction zone.

In any embodiment wherein ethylene and the $C_{3+}$ olefin are fed/introduced to the reaction zone (either separately, together in a feedstock mixture, or both), a $C_{3+}$ olefin:ethylene weight ratio fed/introduced (either separately, together in a feedstock mixture, or both) to the reaction zone can decrease from at least an initial value to less than a final value over a period of time. In an embodiment, the at least initial value of the $C_{3+}$ olefin:ethylene weight ratio fed/introduced to the reaction zone independently can be any at least initial value disclosed herein and the less than final value of the $C_{3+}$ olefin:ethylene weight ratio fed/introduced to the reaction zone independently can be any less than final value disclosed herein. In an embodiment, the at least initial value can be a value of at least 0.5:1, 0.75:1, 1:1, 1.5:1, 2:1, 3:1, 5:1, 10:1, 25:1, 50:1, or 100:1. In an embodiment, the less than final value can be a value less than 0.2:1, 0.15:1, 0.1:1, 0.08:1, 0.06:1, 0.04:1, 0.02:1, or 0.01:1. In an embodiment, the $C_{3+}$ olefin:ethylene weight ratio can decrease from any greater than initial value disclosed herein to any less than final value disclosed herein. Thus, in some non-limiting embodiments, the $C_{3+}$ olefin:ethylene weight ratio fed/introduced to the reaction zone can decrease from at least 0.5:1 to less than 0.2:1, from at least 1:1 to less than 0.2:1, from at least 2:1 to less than 0.15:1, from at least 3:1 to less than 0.1:1, from at least 5:1 to less than 0.15:1, from at least 10:1 to less than 0.2:1, from at least 100:1 to less than 0.1:1. Other embodiments for which the $C_{3+}$ olefin:ethylene weight ratio fed/introduced to the reaction zone can decrease from an initial value to a final value are readily apparent to those skilled in the art with the aid of this disclosure. In an embodiment wherein ethylene and the $C_{3+}$ olefin are fed/introduced to the reaction zone, the period of time can begin when the $C_{3+}$ olefin:ethylene weight ratio falls below the greater than initial value. In an embodiment wherein ethylene and the $C_{3+}$ olefin are fed/introduced to the reaction zone, the period of time can end when the feedstock mixture $C_{3+}$ olefin:ethylene weight ratio falls below the less than final value. In another embodiment wherein ethylene and the $C_{3+}$ olefin are fed/introduced to the reaction zone, the period of time can begin when the feedstock mixture has an initial $C_{3+}$ olefin:ethylene weight ratio of about 1:0; or alternatively, the flow rate of ethylene is about zero. In an embodiment wherein ethylene and the $C_{3+}$ olefin are fed/introduced to the reaction zone, the period of time can end when the feedstock mixture has a $C_{3+}$ olefin:ethylene weight ratio of about 0:1; or alternatively, the flow rate of the $C_{3+}$ olefin is about 0. In an embodiment wherein ethylene and the $C_{3+}$ olefin are fed/introduced to the reaction zone, the period of time can encompass a time where the feedstock mixture $C_{3+}$ olefin:ethylene weight ratio decreases from about 1:0 to about 0:1. In an embodiment wherein ethylene and the $C_{3+}$ olefin are fed/introduced to the reaction zone, the period of time can occur during the startup of the reaction zone.

In an embodiment, the reaction zone period of time and/or the $C_{3+}$ olefin/ethylene feed period of time over which the $C_{3+}$ olefin:ethylene weight ratio can decrease (e.g., from any at least initial value disclosed herein to any less than final value described herein) can provide a benefit to the ethylene oligomerization process, systems, and/or reaction systems described herein (e.g., a decrease in polymer production among other benefits described herein). In an embodiment, the reaction zone period of time and/or the $C_{3+}$ olefin/ethylene feed period of time over which the $C_{3+}$ olefin:ethylene weight ratio can decrease can be greater than or equal to 5, 10, 15, 20, 25, or 30 minutes; alternatively or additionally less than or equal to 6, 4, 3, 2, 1.5, or 1 hour. In an embodiment, the reaction zone period of time and/or the $C_{3+}$ olefin/ethylene feed period of time over which the $C_{3+}$ olefin:ethylene weight ratio can decrease can range from any greater than or equal to value described herein to any less than or equal to value described herein. In some non-limiting embodiments, the reaction zone period of time and/or the $C_{3+}$ olefin/ethylene feed period of time over which the $C_{3+}$ olefin:ethylene weight ratio can decrease can range from greater than or equal to 5 minutes to less than or equal to 6 hours; alternatively, greater than or equal to 10 minutes to less than or equal to 4 hours; alternatively, greater than or equal to 15 minutes to less than or equal to 4 hours; alternatively, greater than or equal to 20 minutes to less than or equal to 3 hours; alternatively, greater than or equal to 25 minutes to less than or equal to 3 hours; alternatively, greater than or equal to 30 minutes to less than or equal to 3 hours; alternatively, greater than or equal to 30 minutes to less than or equal to 2 hours; or alternatively, greater than or equal to 30 minutes to less than or equal to 1.5 hours. Other ranges over which the reaction zone period of time and/or the $C_{3+}$ olefin/ethylene feed period of time over which the $C_{3+}$ olefin:ethylene weight ratio can decrease are readily apparent to those skilled in the art with the aid of this disclosure. Additionally, multiple periods of time over which the reaction zone period of time and/or the $C_{3+}$ olefin/ethylene feed period of time over which the $C_{3+}$ olefin:ethylene weight ratio can decrease can be utilized and these multiple periode of time can have the same duration; or alternatively, at least one of the multiple periods of time can have a duration which is different from the duration of at least another of the multiple periods of time.

The reaction zone period of time and the $C_{3+}$ olefin/ethylene feed period of time over which the $C_{3+}$ olefin:ethylene weight ratio can decrease can occur over the same time, e.g., simultaneously. Alternatively, a portion of the reaction zone period of time can overlap a portion of the $C_{3+}$ olefin/ethylene feed period of time. For example, the reaction zone period of time can lag behind the $C_{3+}$ olefin/ethylene feed period of time period since, due to residence time consideration for the reaction zone 110, there will be a lag in time between when a decrease in the $C_{3+}$ olefin:ethylene weight ratio can be observed in the feed to the reaction zone 110 and when a decrease in the $C_{3+}$ olefin:ethylene weight ratio can be observed in the reaction zone 110 itself. Alternatively, the reaction zone period of time and the $C_{3+}$ olefin/ethylene feed period of time do not overlap. For example, the lag in time between when a decrease in the $C_{3+}$ olefin:ethylene weight ratio can be observed in the feed to the reaction zone 110 and when a decrease in the $C_{3+}$ olefin:ethylene weight ratio can be observed in the reaction zone 110 itself may be long enough that the periods of time (e.g., the reaction zone period of time and the $C_{3+}$ olefin/ethylene feed period of time) occur sequentially or in series (over time).

In any embodiment wherein ethylene and the $C_{3+}$ olefin are fed/introduced to the reaction zone (either separately, together in a feedstock mixture, or both), ethylene, the $C_{3+}$ olefin, or both can be contacted with the organic reaction medium (e.g., at least a portion of the organic reaction medium) prior to contacting the catalyst system. In other embodiments, the ethylene, the $C_{3+}$ olefin, or both can be dispersed with the organic reaction medium (e.g., at least a portion of the organic reaction medium) prior to contacting the catalyst system.

In an embodiment wherein the feedstock mixture comprises ethylene and the organic reaction medium (e.g., at least a portion of the organic reaction medium), ethylene and organic reaction medium can be contacted prior to ethylene contacting the catalyst system. In an embodiment, ethylene can be dispersed in the organic reaction medium (e.g., at least a portion of the organic reaction medium) prior to ethylene contacting the catalyst system. In some embodiments, ethylene and the organic reaction medium can be contacted, and/or the ethylene can be dispersed in the organic reaction medium prior to ethylene contacting the catalyst system in the reaction zone; or alternatively, prior to the ethylene contacting the catalyst system outside the reaction zone. In an embodiment, wherein ethylene and the organic reaction medium are contacted, and/or the ethylene is dispersed in the organic reaction medium prior to ethylene contacting the catalyst system in the reaction zone, the contact and/or dispersion can occur during the reaction zone period of time (e.g., during reaction zone startup), or after the reaction zone period of time (e.g., after reaction zone startup).

In an embodiment wherein the feedstock mixture comprises ethylene, the $C_{3+}$ olefin, and the organic reaction medium (e.g., at least a portion of the organic reaction medium), ethylene, the $C_{3+}$ olefin, and organic reaction medium can be contacted prior to ethylene contacting the catalyst system. In an embodiment, ethylene and/or the $C_{3+}$ olefin can be dispersed in the organic reaction medium (e.g., at least a portion of the organic reaction medium) prior to feedstock mixture contacting the catalyst system. In some embodiments, ethylene and/or the $C_{3+}$ olefin and the organic reaction medium can be contacted, and/or the ethylene and/or $C_{3+}$ olefin can be dispersed in the organic reaction medium prior to ethylene contacting the catalyst system in the reaction zone; or alternatively, prior to the ethylene contacting the catalyst system outside the reaction zone.

In another aspect of the disclosed processes, systems, and/or reaction systems, the presence of the $C_{3+}$ olefin in the reaction zone for a period of time or the introduction/feeding of the $C_{3+}$ olefin to the reaction zone for a period time can be utilized in conjunction with the contacting ethylene with at least a portion of the organic reaction medium to form a feedstock mixture prior to contacting ethylene with the catalyst system. In this aspect, the contacting of the ethylene with the at least a portion of the organic reaction medium can occur during the period of time of where the $C_{3+}$ olefin is present in the reaction zone for a period of time or where the $C_{3+}$ olefin is introduced/fed to the reaction zone; alternatively, after the period of time of where the $C_{3+}$ olefin is present in the reaction zone for a period of time or where the $C_{3+}$ olefin is introduced or fed to the reaction zone; or alternatively, during and after the period of time of where the $C_{3+}$ olefin is present in the reaction zone for a period of time or where the $C_{3+}$ olefin is introduced or fed to the reaction zone. In some embodiments, where ethylene is contacted with at least a portion of the organic reaction medium to form a feedstock mixture prior to contacting ethylene with the catalyst system, the $C_{3+}$ olefin can be present in the feedstock mixture for the period of time when the $C_{3+}$ olefin is introduced/fed to the reaction zone. In this situation, the $C_{3+}$ olefin can be contacted 1) with ethylene before the ethylene contacts the organic reaction medium; 2) with the organic reaction medium prior to ethylene contacting the organic reaction medium; and/or 3) with the feedstock mixture after the ethylene contacts the organic reaction medium. In an embodiment where the $C_{3+}$ olefin is part of the feedstock mixture during the period of time of where the $C_{3+}$ olefin can be introduced/fed to the reaction zone, the minimum (ethylene+$C_{3+}$ olefin) concentration in the feedstock mixture can be 4 mass %, 10 mass %, 25 mass %, 35 mass %, or 40 mass % based upon the total mass of the feedstock mixture; alternatively or additionally, at the maximum (ethylene+$C_{3+}$ olefin) concentration of the feedstock mixture cam be 65 mass %, 60 mass %, 55 mass %, 50 mass %, 48 mass % based upon the total mass in the feedstock mixture. In an embodiment, the (ethylene+$C_{3+}$ olefin) concentration in the feedstock mixture can from any minimum (ethylene+$C_{3+}$ olefin) concentration in the feedstock mixture disclosed herein to any maximum (ethylene+$C_{3+}$ olefin) concentration in the feedstock mixture disclosed herein. In some non-limiting embodiments, the (ethylene+$C_{3+}$ olefin) concentration in the feedstock mixture can be in a range of from 4 mass % to 60 mass %, from 10 mass % to 60 mass %, from 25 mass % to 55 mass %, 35 mass % to 50 mass %, or 40 mass % to 48 mass % based upon the total mass in the feedstock mixture. Other (ethylene+$C_{3+}$ olefin) concentrations in the feedstock mixture ranges that can be utilized are readily apparent to those skilled in the art with the aid of this disclosure.

It is contemplated that the $C_{3+}$ olefin can be present in the reaction zone of the disclosed processes, systems, and reaction systems (e.g., FIGS. 1 to 3) via: i) combination of the $C_{3+}$ olefin with ethylene before ethylene is introduced/fed to the reaction zone or before ethylene joins with organic reaction medium to form the feedstock mixture, ii) combination of the $C_{3+}$ olefin with organic reaction medium before the organic reaction medium is introduced/fed to the reaction zone or before ethylene joins with organic reaction medium to form the feedstock mixture, iii) introducing/feeding the $C_{3+}$ olefin directly to the reaction zone; iv) combination of the $C_{3+}$ olefin with the catalyst system prior to the catalyst system being introduced/fed to the reaction zone or prior to the catalyst system combining with another line outside the reaction zone; v) combination of the $C_{3+}$ olefin with feedstock mixture, vi) combination of the $C_{3+}$ olefin with the dispersed feedstock mixture when the feedstock mixture is dispersed prior to entering the reaction zone; vii) combination of the $C_{3+}$ olefin with a combined feed stream which includes ethylene, the organic reaction medium, and the catalyst system prior to being fed/introduced to the reaction zone; or viii) any combination of i)-vii).

Figure 2:
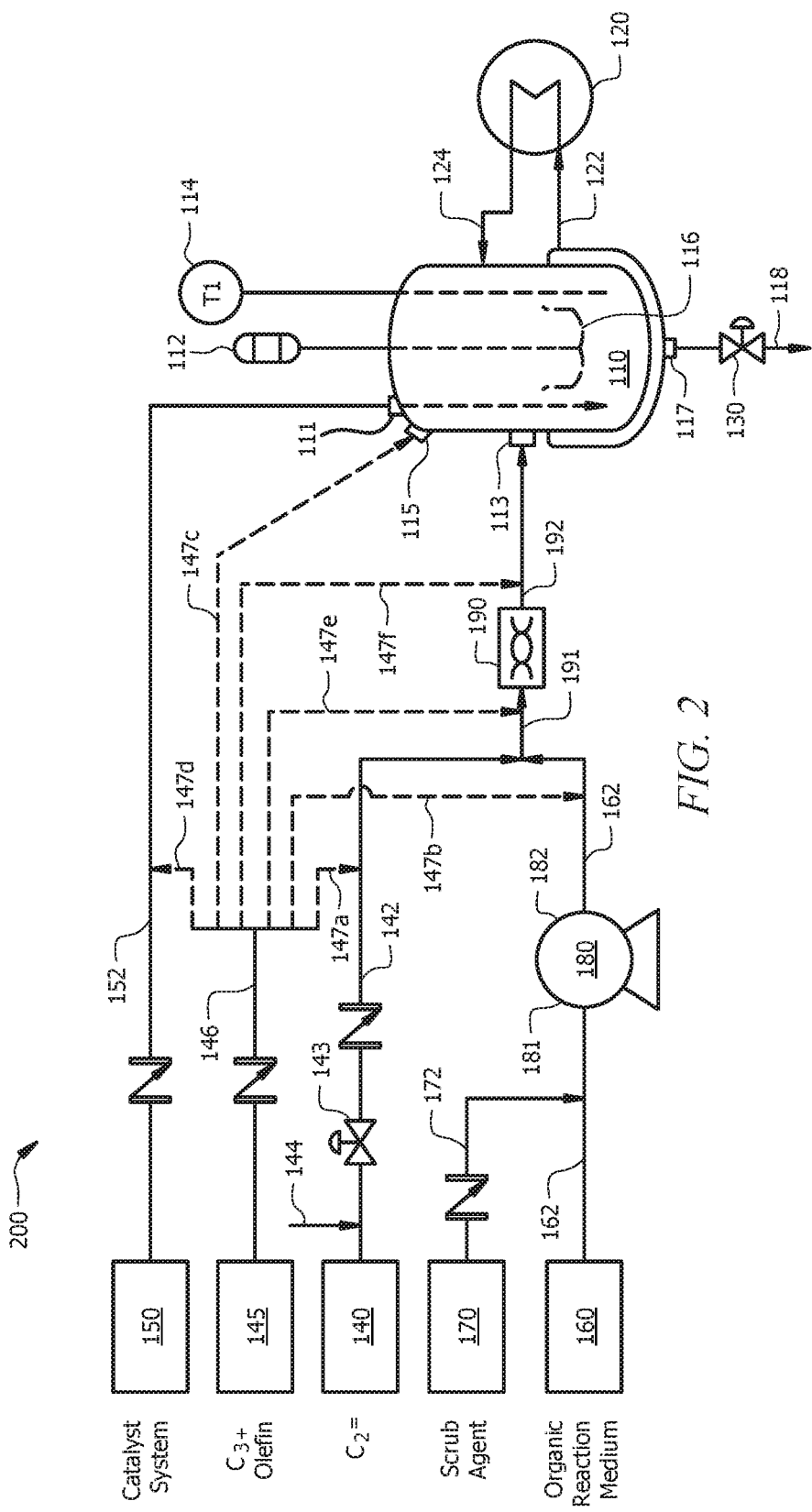
FIG. 2 shows a process flow diagram of another reaction system according to the present disclosure.
Figure 3:
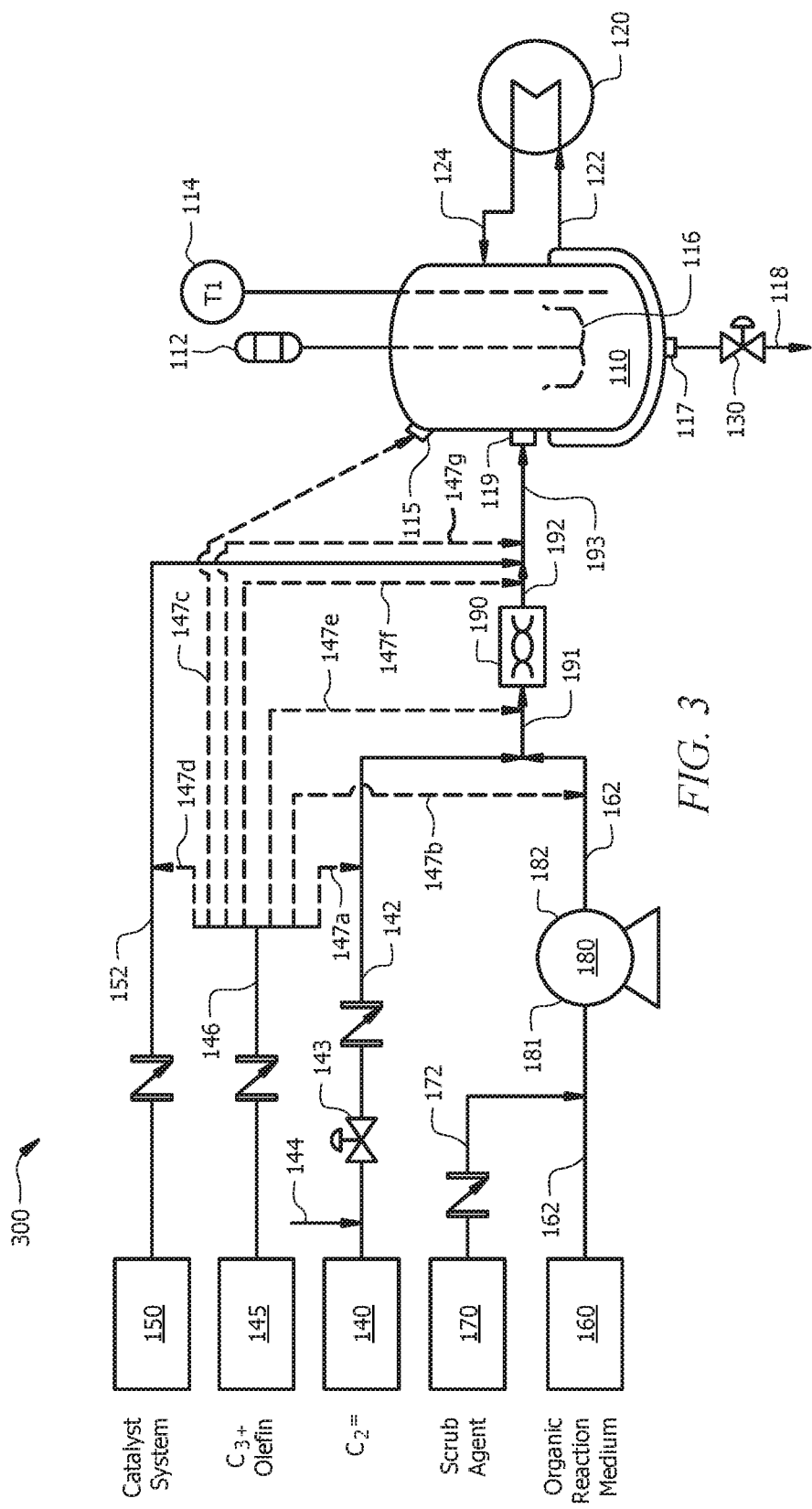
FIG. 3 shows a process flow diagram of another reaction system according to the present disclosure.

It is also contemplated that when a feedstock mixture comprising ethylene is formed, the feedstock mixture can be contacted with the catalyst system inside the reaction zone (an example of which is shown in FIG. 2) or outside the reaction zone (an example of which is shown in FIG. 3). It is further contemplated that ethylene and the organic reaction medium can be dispersed in the feedstock mixture prior to introducing the feedstock mixture to the reaction zone and prior to or after contact of the feedstock mixture with the catalyst system. For example, as shown in FIG. 2, the catalyst system can be introduced into the reaction zone (via line 152 which feeds to the first reaction zone inlet 111, discussed in detail below) separately from feedstock mixture (via line 192 which feeds to the reaction zone inlet 113, also discussed in detail below). Alternatively, as shown in FIG. 3, the catalyst system and the feedstock mixture can be contacted prior to entering the reaction zone 110 (line 152 combines with dispersed line 192 before the components enter the reaction zone inlet 119, discussed in detail herein).

In an embodiment, the ethylene oligomer product can be formed (or the reaction zone can have operating conditions) during the reaction zone period of time where the reaction zone $C_{3+}$ olefin:ethylene weight ratio is decreasing. In some embodiments, the ethylene oligomer product formation conditions (or reaction zone operating conditions) can be any of the ethylene oligomer product formation conditions (or the reaction zone operating conditions) described herein with the exception of any ethylene oligomer product formation conditions (or reaction zone operating conditions) which do not take into consideration embodiments and aspects that the reaction zone contains both ethylene and the $C_{3+}$ olefin and/or $C_{3+}$ olefin:ethylene reaction zone weight ratio is decreasing (e.g., the reaction zone ethylene concentration, the ethylene to chromium mass ratio, among others). Alternatively, the ethylene oligomer product formation conditions (or reaction zone operating conditions) can be any of the ethylene oligomer product formation conditions (or the reaction zone operating conditions) described herein which take into consideration that the reaction zone contains both ethylene and the $C_{3+}$ olefin and/or $C_{3+}$ olefin:ethylene reaction zone weight ratio is decreasing (e.g., the reaction zone ethylene concentration, the ethylene to chromium mass ratio, among others).

Aspects of the disclosure relate to initiating ethylene oligomerization (startup) of a reaction zone in any process, system, and/or reaction system (e.g., FIGS. 1 to 3) described herein. Startup can occur when the reaction zone (e.g., reaction zone 110 of FIGS. 1 to 3) is empty or after reaction zone cleaning (a hard startup) or when the reaction zone (e.g., reaction zone 110 of FIGS. 1 to 3) contains components for an ethylene oligomerization reaction but is not producing ethylene oligomer product (a soft startup). An example of a soft startup situation can be when the flow of ethylene and/or catalyst system is temporarily stopped to address a process, system or reaction system issue and it is desired to again start oligomerization reactions without emptying and/or cleaning the reaction zone (e.g., reaction zone 110 of FIGS. 1 to 3).

Startup of any process, system, and/or reaction system (e.g., FIGS. 1 to 3) described herein can include a reaction zone commencing stage (hereafter commencing stage), and/or a reaction zone phasing stage (hereafter phasing stage). In some embodiments, the startup of any process, system, and/or reaction system (e.g., FIGS. 1 to 3) described herein can further include an optional reaction zone filling stage (hereafter filling stage). Temporally, the filling stage can occur before the commencing stage and phasing stage.

The filling stage of any process, system, and/or reaction system (e.g., FIGS. 1 to 3) described herein can involve filling the reaction zone (e.g., reaction zone 110), either empty, already containing components for an ethylene oligomerization reaction, or simultaneously with one or more components for an ethylene oligomerization reaction, with the $C_{3+}$ olefin (e.g., using any one or more appropriate $C_{3+}$ olefin lines in FIGS. 1-3). Reaction zone filling can occur for any period of time needed to provide the desired amount of $C_{3+}$ olefin to the reaction zone (or attain any desired reaction zone $C_{3+}$ olefin:ethylene ratio disclosed herein). In an aspect, the reaction zone (e.g., reaction zone 110) can be filled with the $C_{3+}$ olefin while no ethylene is being fed or introduced into the reaction zone. Alternatively, the reaction zone (e.g., reaction zone 110) can be filled with the $C_{3+}$ olefin and ethylene (using any $C_{3+}$ olefin:ethylene weight ratio disclosed herein, or to achieve any reaction zone $C_{3+}$ olefin to ethylene $C_{3+}$ olefin weight ratio disclosed herein). In some embodiments, the reaction zone can contain, or can be substantially devoid of, organic reaction medium, catalyst system, hydrogen, and/or scrub agent.

The commencing stage can involve feeding/introducing one or more of the ethylene oligomerization components to the reaction zone (e.g., reaction zone 110 of FIGS. 1 to 3). During the commencing stage, the organic reaction medium, the catalyst system, optionally the $C_{3+}$ olefin, and optionally, hydrogen can be fed/introduced into the reaction zone (e.g., reaction zone 110 of FIGS. 1 to 3) before ethylene is fed/introduced to the reaction zone. The organic reaction medium, the catalyst system, optionally the $C_{3+}$ olefin, and optionally hydrogen can be fed/introduced to the reaction zone in any manner and/or any order including adding one or more simultaneously. For example, a non-limiting order of feeding/introducing the ethylene oligomerization components to the reaction zone during startup can be to first feed/introduce organic reaction medium to the reaction zone (e.g., using any one or more appropriate lines 162, 191, 192, and 193 in FIGS. 1-3), then feed/introduce the catalyst system and optionally hydrogen to the reaction zone in any order (e.g., using the catalyst system feed line 152 and/or one or more appropriate lines 144, 142, 191, 102, and 193 for hydrogen flow in FIGS. 1-3), and then feed/introduce the $C_{3+}$ olefin to the reaction zone (e.g., using any one or more appropriate lines 146 and 147a, b, c, d, e, f, or g in FIGS. 1-3). Another non-limiting order of feeding/introducing the ethylene oligomerization components to the reaction zone during startup can be to first feed/introduce organic reaction medium to the reaction zone (e.g., using any one or more appropriate lines 162, 191, 192, and 193 in FIGS. 1-3), then feed/introduce the $C_{3+}$ olefin to the reaction zone (e.g., using any one or more appropriate lines 146 and 147a, b, c, d, e, f, or g in FIGS. 1-3), and then then feed/introduce the catalyst system and optionally hydrogen to the reaction zone in any order (e.g., using the catalyst system feed line 152 and/or one or more appropriate lines 144, 142, 191, 102, and 193 for hydrogen flow in FIGS. 1-3). Other orders of feeding/introducing the ethylene oligomerization components to the reaction zone during startup are readily apparent to those having ordinary skill in the art with the aid of this disclosure.

In an alternative, the $C_{3+}$ olefin can be fed/introduced to the reaction zone (e.g., reaction zone 110 of FIGS. 1 to 3) in the phasing stage (e.g., introduced simultaneously, but not necessarily combined with ethylene). In such alternative, the organic reaction medium, the catalyst system, and optionally, hydrogen can be fed/introduced to the reaction zone in the commencing stage in any order such as those described herein. In another alternative, the $C_{3+}$ olefin can be fed/introduced to the reaction zone (e.g., reaction zone 110 of FIGS. 1 to 3) in the filling stage (e.g., using any one or more appropriate $C_{3+}$ olefin feed lines 146 and 147a, b, c, d, e, f, or g in FIGS. 1-3); that is, the $C_{3+}$ olefin is not introduced to the reaction zone in the commencing stage or the phasing stage.

The phasing stage of any process, system, and/or reaction system (e.g., FIGS. 1 to 3) described herein can involve decreasing the reaction zone (e.g., reaction zone 110 of FIGS. 1 to 3) $C_{3+}$ olefin:ethylene weight ratio over a period of time. In an embodiment, decreasing the reaction zone $C_{3+}$ olefin:ethylene weight ratio over a period of time can be accomplished by feeding/introducing ethylene to a reaction zone containing the $C_{3+}$ olefin and/or decreasing the $C_{3+}$ olefin:ethylene weight ratio of the $C_{3+}$ olefin and ethylene being fed/introduced to the reaction zone. In an aspect, the $C_{3+}$ olefin can be fed/introduced (e.g., using any one or more appropriate $C_{3+}$ olefin feed lines 146 and 147a, b, c, d, e, f, or g in FIGS. 1-3) to the reaction zone (e.g., reaction zone 110 of FIGS. 1 to 3) in the filling stage, followed by decreasing the reaction zone $C_{3+}$ olefin:ethylene weight ratio by feeding/introducing ethylene to the reaction zone using any one or more appropriate lines 142, 191, 192, and 193 in FIGS. 1-3. In another aspect, the ethylene and $C_{3+}$ olefin can be fed/introduced (e.g., using any appropriate lines 142, 191,192, and 193 for ethylene and one or more appropriate lines 146 and 147a, b, c, d, e, f, or g for $C_{3+}$ olefin) to the reaction zone (e.g., reaction zone 110 of FIGS. 1-3.) such that $C_{3+}$ olefin:ethylene weight ratio fed/introduced to the reaction zone and/or the reaction zone $C_{3+}$ olefin:ethylene weight ratio decreases from at least an initial value to less than a final value over a period of time. Embodiments for the decrease of the reaction zone $C_{3+}$ olefin:ethylene weight ratio and the decrease of the $C_{3+}$ olefin:ethylene weight ratio fed/introduced to the reaction zone are independently provided herein and can be utilized without limitation to further describe the phasing stage of the process, system, and/or reaction system (e.g., FIGS. 1 to 3) described herein. Without being limited by theory, it is believed that having $C_{3+}$ olefin in the reaction zone and/or feeding $C_{3+}$ olefin to the reaction zone during reaction zone startup can reduce the formation of polymer during reaction zone startup (hard startup or soft startup), as described herein.

In an aspect, the phasing stage can be initiated by feeding/introducing ethylene to the reaction (e.g., reaction zone 110 of FIGS. 1-3 using any appropriate line 142, 191, 192, and 193 for flow of ethylene). The phasing stage can be initiated after or simultaneously with feeding/introducing the $C_{3+}$ olefin to the reaction zone (e.g., reaction zone 110 of FIGS. 1-3 using any appropriate line 142, 191, 192, and 193 for flow of ethylene).

The decrease in the reaction zone $C_{3+}$ olefin:ethylene weight ratio and/or the decrease of the $C_{3+}$ olefin:ethylene weight ratio fed/introduced to the reaction zone during the phasing stage is not limited to a particular technique and can occur via linear decrease (e.g., a constant increase over a given period of time), a step change decrease (e.g., decrease by changing a set value at set points of time during the period of time), or a combination thereof. During the phasing stage the decrease in the reaction zone $C_{3+}$ olefin:ethylene weight ratio and/or the decrease of the $C_{3+}$ olefin:ethylene weight ratio fed/introduced to the reaction zone can be accomplished by increasing the ethylene flow rate and/or decreasing $C_{3+}$ olefin flowrate to the reaction zone until the desired reaction zone $C_{3+}$ olefin:ethylene weight ratio and/or $C_{3+}$ olefin:ethylene weight ratio is achieved. Alternatively, the decrease in the reaction zone $C_{3+}$ olefin:ethylene weight ratio and/or the decrease of the $C_{3+}$ olefin:ethylene weight ratio fed/introduced to the reaction zone can be accomplished by increasing the ethylene flow rate and decreasing $C_{3+}$ olefin flowrate to the reaction zone until the desired reaction zone $C_{3+}$ olefin:ethylene weight ratio and/or $C_{3+}$ olefin:ethylene weight ratio is achieved.

After ending the phasing stage, ethylene, the organic reaction medium, the catalyst system, and optionally hydrogen can be fed/introduced to the reaction zone (e.g., reaction zone 110 of FIGS. 1-3) to achieve the desired ethylene oligomerization operation and/or reaction zone conditions (e.g., ethylene oligomerization and/or reaction zone conditions to achieve steady state operation). In an aspect, it is contemplated that no significant amount of $C_{3+}$ olefin is fed/introduced to the reaction zone during steady state operation of the reaction zone (e.g., reaction zone 110 of FIGS. 1-3). Thus, no significant amount of $C_{3+}$ olefin is introduced to the reaction zone via a reaction zone inlet (e.g., any reaction zone inlet of FIGS. 1-3) during steady state operation. As used herein no significant amount of $C_{3+}$ olefin is fed/introduced to the reaction zone during steady state operation of the reaction zone is defined as a $C_{3+}$ olefin:ethylene weight ratio fed/introduced to the reaction zone of less than 0.1:1, 0.08:1, 0.06:1, 0.04:1, 0.02:1, or 0.01:1.

During steady state operation, ethylene, the organic reaction medium, the catalyst system, and optionally, hydrogen can be periodically or continuously introduced to the reaction zone (e.g., reaction zone 110 of FIGS. 1-3). Moreover, in some embodiments, reaction zone effluent can be periodically or continuously removed from the reaction zone (e.g., reaction zone 110 of FIGS. 1-3). For example, reaction zone inlets (e.g., the reaction zone inlets of FIGS. 1-3) can be configured to periodically or continuously introduce/feed the catalyst system, ethylene, organic reaction medium, and optionally hydrogen to the reaction zone while a reaction zone outlet (e.g., the reaction zone outlets of FIGS. 1-3) can be configured to periodically or continuously discharge or remove the reaction zone effluent from the reaction zone. In some embodiments, the desired ethylene oligomerization operation can include contacting ethylene with the organic reaction medium to form the feedstock mixture prior to ethylene contacting the catalyst system. Additionally, when ethylene is contacted with the organic reaction medium to form the feedstock mixture prior to ethylene contacting the catalyst system ethylene can be dispersed with the organic reaction medium prior to ethylene contacting the catalyst system. In an embodiment wherein the ethylene and the organic reaction medium are contacted, and/or the ethylene can be dispersed in the organic reaction medium prior to ethylene contacting the catalyst system in the reaction zone (e.g., reaction zone 110 of FIGS. 1-3), the ethylene can contact the catalyst system in the reaction zone; or alternatively, ethylene can contact the catalyst system outside the reaction zone.

In an embodiment, any process, system, and/or reaction system described herein can further comprise preparing the catalyst system. In an embodiment, the catalyst system can be prepared by 1) contacting the chromium component (any described herein) and the aluminoxane compound (any described herein) to form a catalyst system mixture, and 2) aging the catalyst system mixture in the substantial absence of ethylene to form and aged catalyst system mixture. In an embodiment the catalyst system mixture can be aged for a period of time. Typically, the minimum aging time can be 5 seconds, 10 seconds, 30 seconds, 1 minute, 5 minutes, 10 minutes, or 20 minutes; additionally or alternatively, the maximum aging time can be 48 hours, 36 hours, 24 hours, 18 hours, 12 hours, 6 hours, 4 hours, or 2 hours. Generally, the aging time can be in a range from any minimum time disclosed herein to any maximum time disclosed herein. Accordingly, suitable non-limiting ranges for the aging time can include from 5 seconds to 48 hours, from 10 seconds to 36 hours, from 30 seconds to 24 hours, from 1 minute to 18 hours, from 5 minutes to 6 hours, from 10 minutes to 4 hours, or from 20 minutes to 2 hours. Other appropriate ranges for the aging time are readily apparent from this disclosure. In further embodiments, the catalyst system mixture can be aged at any suitable temperature, ranging from sub-ambient temperatures, to ambient temperature (approximately 25° C.), to elevated temperatures. While not limited thereto, the catalyst system mixture can be aged at a temperature in a range from 0° C. to 100° C., from 10° C. to 75° C., from 15° C. to 60° C., or from 20° C. to 40° C. In these and other embodiments, these temperature ranges also are meant to encompass circumstances where the catalyst system mixture can be aged at a series of different temperatures, instead of at a single fixed temperature, falling within the respective ranges. In a non-limiting embodiment, a substantial absence of ethylene can be a maximum molar ratio of ethylene to chromium component of 5:1, 4:1, 3:1, 2:1, 1:1, 0.5:1, 0.25:1, or 0.1:1. In some non-limiting embodiments, the substantial absence of ethylene can be a maximum ethylene partial pressure 10 psig (69 kPa), 5 psig (34 kPa), 4 psig (28 kPa), 3 psig (21 kPa), 2 psig (14 kPa), 1 psig (7 kPa), or 0.5 psig (3.4 kPa). In some embodiments, the catalyst system can be formed by contacting a diluent and/or a solvent with the chromium component (any described herein) and the aluminoxane (any described herein). In an embodiment, the diluent and/or solvent can be any organic reaction medium described herein. In embodiments where the catalyst system can be formed by contacting a diluent and/or a solvent with the chromium component (any described herein) and the aluminoxane, the chromium component to solvent and/or diluent weight ratio can range from 1:100 to 1:15,000, or 1:150 to 1:10,000.

FIG. 1 shows a process flow diagram of a reaction system 100 according to the present disclosure. The system 100 includes one or more of an ethylene source 140 in fluid communication with an ethylene feed line 142; a $C_{3+}$ olefin source 145 in communication with a $C_{3+}$ feed line 146; a catalyst system source 150 in fluid communication with a catalyst system feed line 152; an organic reaction medium source 160 in fluid communication with an organic reaction medium feed line 162; an optional scrub agent source 170 in communication with a scrub agent feed line 172; an optional hydrogen feed line 144 feeding to the ethylene feed line 142; an optional pump 180; a reaction zone 110 having a first reaction zone inlet 111, a second reaction zone inlet 213, a third reaction zone inlet 215, a fourth reaction zone inlet 115, and a reaction zone outlet 117 representing one or more reaction zone outlets; and a heat exchanger 120. It is contemplated that the reaction system 100 of FIG. 1 can include appropriate equipment (e.g., valves, control devices, sensors, electrical writing, insulation) which are not shown in FIG. 1 yet can be included according to those skilled in the art with the aid of this disclosure.

The first reaction zone inlet 111 (representing one or more reaction zone inlets) can be configured to introduce a catalyst system (which can be optionally combined with $C_{3+}$ olefin for a period of time) as described herein to the reaction zone 110, the second reaction zone inlet 213 (representing one or more reaction zone inlets) can be configured to introduce ethylene (which can be optionally combined with $C_{3+}$ olefin for a period of time) to the reaction zone 110, the third reaction zone inlet 215 (representing one or more reaction zone inlets) can be configured to introduce organic reaction medium (which can be optionally combined with $C_{3+}$ olefin for a period of time) to the reaction zone 110, and the reaction zone outlet 117 (representing one or more reaction zone outlets) can be configured to discharge or remove a reaction zone effluent comprising an ethylene oligomer product from the reaction zone 110 via line 118. Valve 130 can be used in line 118 to control a flow of the reaction zone effluent in line 118 and/or to control a pressure of the reaction zone 110. Reaction zone effluent in line 118 can then feed to equipment (not shown) for isolating various streams (e.g., the desired oligomer) from the reaction zone effluent.

An aspect of the disclosed systems and processes is that an optional fourth reaction zone inlet 115 (representing one or more reaction zone inlets) can be configured to introduce the $C_{3+}$ olefin for a period of time to the reaction zone 110. For the reaction zone 110 configuration shown in FIG. 1, the inlets 111 and 213 can be placed as far away from one another as possible. In an aspect, the inlet 111 is placed near the stirring in the reaction zone 110 to improve dispersion of the catalyst system in the reaction zone 110 before contacting ethylene which is introduced via inlet 213. Moreover, inlets 111, 115, 213, and 215 can be separated as far as possible from the outlet 117. Other considerations for placement of the inlets 111, 115, 213, and 215 as well as outlet 117 may be taken into account, for example, when the reaction zone 110 includes a recycle feature.

The catalyst system can flow through catalyst system feed line 152 from the catalyst system source 150 to the first reaction zone inlet 111, where the catalyst system can be fed to the reaction zone 110. The catalyst system feed line 152 can optionally include a solvent and/or a diluent with the catalyst system. The solvent and/or diluent can be any organic reaction medium described herein. In an embodiment, the solvent and/or diluent can be the organic reaction medium utilized in the process, system, or reaction system.

The catalyst system can be dispersed in the solvent and/or the diluent in the catalyst system feed line 152. For example, the catalyst system feed line 152 can include a mixing device (not shown), similar to mixing device 190 described herein for FIG. 2 or in a precontactor apparatus (not shown), which can be configured to disperse the catalyst system in the solvent and/or diluent prior to the catalyst system entering the reaction zone 110 via first reaction zone inlet 111. When solvent and/or diluent and the catalyst system are present in the catalyst system feed line 152 of FIG. 1, the chromium: solvent and/or diluent mass ratio can be any disclosed herein.

Optionally, scrub agent (described herein) can flow in the scrub agent feed line 172. In an embodiment some or all of the aluminoxane of the catalyst system can flow in the scrub agent feed line 172. For example, all of the aluminoxane of the catalyst system can flow in scrub agent feed line 172 in the in-situ generation of the catalyst system; or alternatively, the aluminoxane can flow in both the catalyst system feed line 152 and the scrub agent feed line 172. In an embodiment, the scrub agent may not be an aluminoxane of the catalyst system.

Organic reaction medium can flow in organic reaction medium feed line 162 from the organic reaction medium source 160 to the suction side 181 of pump 180.

At least a portion of the organic reaction medium can be contacted with a scrub agent (e.g., an alkylaluminum compound, any described herein) prior to introduction to the reaction zone 110. FIG. 1 shows scrub agent can be added via feed line 172 to the organic reaction medium feed line 162 such that line 162 contains both the scrub agent and the organic reaction medium. Alternatively, the scrub agent may not be combined with the organic reaction medium in the organic reaction medium feed line 172. In a non-limiting embodiment where the catalyst system is formed in-situ within reaction zone 110, an aluminoxane can be utilized as the scrub agent and can be all or a portion of the aluminoxane component of the catalyst system. Alternatively, the scrub agent is not combined with the organic reaction medium in the organic reaction medium. The scrub agent is independently disclosed herein and can be utilized to further described reaction system 100. The scrub agent is independently disclosed herein and can be utilized to further described reaction system 100.

In embodiments where the organic reaction medium and ethylene are contacted to form a feedstock mixture, at least a portion of the organic reaction medium can be contacted with the scrub agent (e.g., an alkylaluminum compound, any described herein) prior to contact of the portion of organic reaction medium with ethylene. FIG. 1 shows the scrub agent can be added via line 172 to the organic reaction medium feed line 162, before the organic reaction medium contacts ethylene via combination of the organic reaction medium feed line 162 with the ethylene feed line 142. The scrub agent is independently disclosed herein and can be utilized to further described reaction system 100.

In FIG. 1, all of the organic reaction medium can be fed to the reaction zone via line 162. However, as is discussed herein, it is contemplated that only a portion of the total amount of organic reaction medium which is used in the system 100 is in line 162 and optionally contacted with the scrub agent prior to introduction to the reaction zone 110; e.g., the other portions can be mixed with the catalyst system in catalyst system feed line 152.

Ethylene flows in ethylene feed line 142 from the ethylene source 140 to the second reaction zone inlet 213.

Hydrogen optionally can be used to control the selective ethylene oligomerization reaction. The optional hydrogen can be fed into the ethylene feed line 142 via hydrogen feed line 144. The combination of hydrogen with ethylene in the ethylene feed line 144 can be upstream of valve 143 as shown in FIG. 1; or alternatively, downstream of valve 143. While the hydrogen feed line 144 in FIG. 1 is shown as feeding to the ethylene feed line 142, it is contemplated that the hydrogen feed line 144 can fluidly connect to any reaction zone inlet (e.g., reaction zone inlet 111, reaction zone inlet 115, reaction zone inlet 213, or reaction zone inlet 215) directly or via another line (e.g., line 146, line 147a, b, c, or d, line 152, line 162, or line 172).

The $C_{3+}$ olefin can be introduced, for a period of time, to reaction system 100 via one or more of lines 147a-d (the alternative nature being shown as dashed lines). For example, the $C_{3+}$ olefin, which can be introduced for a period of time, can flow from the $C_{3+}$ olefin source 145 via line 146 and one or more of: i) line 147a to combine with ethylene flowing in ethylene feed line 142, ii) line 147b to combine with the organic reaction medium flowing in line 162, iii) 147c to add the $C_{3+}$ olefin directly to the reaction zone 110, and iv) line 147d to combine with the catalyst system flowing in line 152.

When introducing the $C_{3+}$ olefin for a period of time via line 146 and line 147a, the $C_{3+}$ olefin can combine with ethylene flowing in ethylene feed line 142. The ethylene feed line 142 (comprising ethylene, the $C_{3+}$ olefin, and optionally hydrogen) can connect to the reaction zone 110 via the second reaction zone inlet 213. In the aspect where the $C_{3+}$ olefin is introduced for a period of time via line 146 and line 147a, the $C_{3+}$ olefin can flow via lines 146, 147a, and 142.

When introducing the $C_{3+}$ olefin for a period of time via line 146 and line 147b, the $C_{3+}$ olefin can combine with the organic reaction medium (which can optionally previously combined with the scrub agent) flowing in the organic reaction medium feed line 162. The organic reaction medium line 162 (comprising the organic reaction medium, the $C_{3+}$ olefin, and optionally scrub agent) can flow to the reaction zone 110 via the third reaction zone inlet 215. In the aspect where the $C_{3+}$ olefin is introduced for a period of time via line 146 and line 147b, the $C_{3+}$ olefin can flow via lines 146, 147b, and 162 to the reaction zone 110.

When introducing the $C_{3+}$ olefin for a period of time via line 146 and line 147c, the $C_{3+}$ olefin can flow directly to the reaction zone 110 via the fourth reaction zone inlet 115 which can be configured to introduce the $C_{3+}$ olefin for a period of time to the reaction zone 110.

When introducing the $C_{3+}$ olefin for a period of time via line 146 and line 147d, the $C_{3+}$ olefin can combine with the catalyst system flowing in catalyst system feed line 152. In such an aspect, the catalyst system can flow for a period of time with the $C_{3+}$ olefin in line 152 to the reaction zone 110 via the first reaction zone inlet 111.

With respect to the timing of the flow of the $C_{3+}$ olefin relative to the flow of ethylene for the period of time, the flow of $C_{3+}$ olefin can commence before or simultaneously with the flow of ethylene regardless which of lines 147a, 147b, 147c, and/or 147d the $C_{3+}$ olefin flows. Alternatively, the flow of the $C_{3+}$ olefin can commence before the flow of ethylene (when the reaction zone 110 is empty, for example, during hard startup, or when the reaction zone 110 already contains material, for example, in a soft startup after temporary cessation of the flow of ethylene and/or catalyst system to the reaction zone 110 to address process or system issues), then be stopped temporarily, and then again commenced before or at the same time (simultaneously) as the flow of ethylene and/or catalyst system. With respect to the timing of the flow of the $C_{3+}$ olefin relative to the flow of catalyst system for the period of time, the flow of the $C_{3+}$ olefin can commence before, simultaneously, or after the flow of the catalyst system regardless of which lines 147a, 147b, 147c, and/or 147d the $C_{3+}$ olefin flows. With respect to the timing of the flow of the $C_{3+}$ olefin relative to the flow of organic reaction medium for the period of time, the flow of the $C_{3+}$ olefin can commence before, simultaneously, or after the flow of the organic reaction medium regardless of which lines 147a, 147b, 147c, and/or 147d the $C_{3+}$ olefin flows. With respect to the timing of the flow of the $C_{3+}$ olefin relative to the flow of scrub agent for the period of time, the flow of the $C_{3+}$ olefin can commence before, simultaneously, or after the flow of the scrub agent regardless of which lines 147a, 147b, 147c, and/or 147d the $C_{3+}$ olefin flows.

It is noted that in the system 100 of FIG. 1, ethylene can be fed to the reaction zone 110 separately with respect to the catalyst system and with respect to the organic reaction medium. That is, ethylene can be fed to the reaction zone 110 via line 142 and via second reaction zone inlet 213; while, the catalyst system can be fed to the reaction zone 110 via line 152 and via first reaction zone inlet 111, and while the organic reaction medium can be fed to the reaction zone 110 via line 162 and via the third reaction zone inlet 215.

The separately fed ethylene can be substantially free of the catalyst system or at least a chromium component of the catalyst system. By "substantially free" it is meant that the ethylene has equal to or less than 1.0, 0.9, 0.8, 0.7, 0.6, 0.5, 0.4, 0.3, 0.2, or 0.1 wt. % of the catalyst system present based on the total weight of the catalyst system entering the reaction zone 110.

FIG. 2 shows a process flow diagram of a reaction system 200 according to the present disclosure. The system 200 includes one or more of an ethylene source 140 in fluid communication with an ethylene feed line 142; a $C_{3+}$ olefin source 145 in communication with a $C_{3+}$ feed line 146; a catalyst system source 150 in fluid communication with a catalyst system feed line 152; an organic reaction medium source 160 in fluid communication with an organic reaction medium feed line 162; an optional scrub agent source 170 in communication with a scrub agent feed line 172; an optional hydrogen feed line 144 feeding to the ethylene feed line 142; an optional pump 180; an optional mixing device 190; a reaction zone 110 having a first reaction zone inlet 111, a second reaction zone inlet 113, an optional third reaction zone inlet 115, and a reaction zone outlet 117 representing one or more reaction zone outlets; and a heat exchanger 120. It is contemplated that the reaction system 200 of FIG. 2 can include appropriate equipment (e.g., valves, control devices, sensors, electrical writing, insulation) which are not shown in FIG. 2 yet can be included according to those skilled in the art with the aid of this disclosure.

The first reaction zone inlet 111 (representing one or more reaction zone inlets) can be configured to introduce a catalyst system (which can be optionally combined with $C_{3+}$ olefin for a period of time) as described herein to the reaction zone 110, the second reaction zone inlet 113 (representing one or more reaction zone inlets) can be configured to introduce a feedstock mixture (which can be optionally combined with $C_{3+}$ olefin for a period of time) to the reaction zone 110, and the reaction zone outlet 117 (representing one or more reaction zone outlets) can be configured to discharge or remove a reaction zone effluent comprising an ethylene oligomer product from the reaction zone 110 via line 118. Valve 130 can be used in line 118 to control a flow of the reaction zone effluent in line 118 and/or to control a pressure of the reaction zone 110. Reaction zone effluent in line 118 can then feed to equipment (not shown) for isolating various streams (e.g., the desired oligomer) from the reaction zone effluent.

An aspect of the disclosed systems and processes is that an optional third reaction zone inlet 115 (representing one or more reaction zone inlets) can be configured to for a period of time introduce the $C_{3+}$ olefin directly to the reaction zone 110. For the reaction zone 110 configuration shown in FIG. 2, the inlets 111 and 113 can be placed as far away from one another as possible. In an aspect, the inlet 111 is placed near the stirring in the reaction zone 110 to improve dispersion of the catalyst system in the reaction zone 110 before contacting ethylene which is introduced via inlet 113. Moreover, inlets 111, 113, and 115 can be separated as far as possible from the outlet 117. Other considerations for placement of the inlets 111, 113, and 115 as well as outlet 117 may be taken into account, for example, when the reaction zone 110 includes a recycle feature.

The catalyst system can flow through catalyst system feed line 152 from the catalyst system source 150 to the first reaction zone inlet 111, where the catalyst system can be fed to the reaction zone 110. The catalyst system feed line 152 can optionally include a solvent and/or a diluent along with the catalyst system. The solvent and/or diluent can be any organic reaction medium described herein. In an embodiment, the solvent and/or diluent can be the organic reaction medium utilized the process, system, or reaction system. The catalyst system can be dispersed in the solvent and/or diluent in the catalyst system feed line 152. For example, the catalyst system feed line 152 can include a mixing device (not shown), similar to mixing device 190 or in a precontactor apparatus (not shown), which can be configured to disperse the catalyst system in the solvent and/or diluent prior to the catalyst system entering the reaction zone 110 via first reaction zone inlet 111. When solvent and/or diluent and the catalyst system are present in the catalyst system feed line 152 of FIG. 2, the chromium:solvent and/or diluent mass ratio can be any disclosed herein.

Optionally, scrub agent (described herein) can flow in the scrub agent feed line 172. In an embodiment some or all of the aluminoxane of the catalyst system can flow in the scrub agent feed line 172. For example, all of the aluminoxane of the catalyst system can flow in scrub agent feed line 172 in the in-situ generation of the catalyst system; or alternatively, the aluminoxane can flow in both the catalyst system feed line 152 and the scrub agent feed line 172. In an embodiment, the scrub agent may not be an aluminoxane of the catalyst system. In embodiments where the organic reaction medium and ethylene are contacted to form a feedstock mixture, at least a portion of the organic reaction medium can be contacted with the scrub agent (e.g., an alkylaluminum compound, any described herein) prior to contact of the portion of organic reaction medium with ethylene. FIG. 2 shows the scrub agent can be added via line 172 to the organic reaction medium feed line 162, before the organic reaction medium contacts ethylene via combination of the organic reaction medium feed line 162 with the ethylene feed line 142. The scrub agent is independently disclosed herein and can be utilized to further describe reaction system 200.

Organic reaction medium (optionally combined with the catalyst system) can flow in organic reaction medium feed line 162 from the organic reaction medium source 160, through the pump 180, and to the point where the ethylene feed line 142 and the organic reaction medium feed line 162 join.

At least a portion of the organic reaction medium can be contacted with a scrub agent (e.g., an alkylaluminum compound, any described herein) prior to introduction to the reaction zone 110. FIG. 2 shows scrub agent can be added via feed line 172 to the organic reaction medium feed line 162 such that line 162 can contain both the scrub agent and the organic reaction medium. Alternatively, the scrub agent may not be combined with the organic reaction medium in the organic reaction medium feed line 162. In a non-limiting embodiment where the catalyst system is formed in-situ within reaction zone 110, an aluminoxane can be utilized as the scrub agent and all or a portion of the aluminoxane component of the catalyst system. The scrub agent is independently disclosed herein and can be utilized to further described reaction system 200.

In embodiments where the organic reaction medium and ethylene are contacted to form a feedstock mixture, at least a portion of the organic reaction medium can be contacted with the scrub agent (e.g., an alkylaluminum compound) prior to contact of the portion of organic reaction medium with ethylene. FIG. 2 shows the scrub agent can be added via line 172 to the organic reaction medium feed line 162, before the organic reaction medium contacts ethylene via combination of the organic reaction medium feed line 162 with the ethylene feed line 142. Alternatively, the scrub agent may not be combined with the organic reaction medium in the organic reaction medium feed line 162. The scrub agent is independently disclosed herein and can be utilized to further described reaction system 200.

In FIG. 2, all of the organic reaction medium can be fed to the reaction zone via line 162. However, as is discussed herein, it is contemplated that only a portion of the total amount of organic reaction medium which is used in the system 200 can be in line 162 and optionally contacted with the scrub agent prior to introduction to the reaction zone 110; e.g., the other portions can be mixed with the catalyst system in catalyst system feed line 152 and/or can be included in a bypass line which feeds directly to the reaction zone 110. Alternatively, the scrub agent may not be combined with the organic reaction medium, and the organic reaction medium feed line 162 can flow directly to the suction side 181 of pump 180.

Ethylene (which can be optionally combined with the $C_{3+}$ olefin for a period of time and/or optionally combined with hydrogen) can flow in ethylene feed line 142 from the ethylene source 140 and can combine with organic reaction medium (which can be optionally previously combined with scrub agent and/or $C_{3+}$ olefin) flowing in line 162 on the head side 182 of the pump 180. Alternatively, ethylene can be combined with the organic reaction medium flowing in line 162 on the suction side 181 of the pump 180.

Combination of the ethylene in line 142 with the organic reaction medium in line 162 can yield a feedstock mixture in feedstock mixture feed line 191. The feedstock mixture can flow through an optional mixing device 190 where ethylene and the organic reaction medium (which can be optionally previously combined with scrub agent and/or $C_{3+}$ olefin) can be dispersed, and subsequently can flow via dispersed feedstock mixture feed line 192 as a dispersed feedstock mixture to the second reaction zone inlet 113.

Hydrogen optionally can be used to control oligomerization reactions. The optional hydrogen can be fed into the ethylene feed line 142 of reaction system 200 via hydrogen feed line 144. The combination of hydrogen with ethylene in the ethylene feed line 144 can be upstream of valve 143 as shown in FIG. 2; or alternatively, downstream of valve 143. While the hydrogen feed line 144 in FIG. 2 is shown as feeding to the ethylene feed line 142, it is contemplated that the hydrogen feed line 144 can fluidly connect to any reaction zone inlet (e.g., reaction zone inlet 111, reaction zone inlet 113, or reaction zone inlet 115) directly or via another line (e.g., line 146, line 147a, b, c, d, e, or f, line 152, line 162, line 172, line 191, or line 192).

The $C_{3+}$ olefin can be introduced, for a period of time, to reaction system 200 via any one or more of lines 147a-f (the alternative nature being shown as dashed lines). For example, the $C_{3+}$ olefin, which can be introduced/fed for a period of time to the reaction zone, can flow from the $C_{3+}$ olefin source 145 via line 146 and: i) via line 147a to combine with ethylene flowing in ethylene feed line 142, before ethylene joins with organic reaction medium flowing in feed line 162 to form the feedstock mixture in feedstock mixture line 191, ii) via line 147b to combine with the organic reaction medium flowing in line 162, before the organic reaction medium joins with ethylene to form the feedstock mixture in line 191, iii) via line 147c to add the $C_{3+}$ olefin directly to the reaction zone 110, iv) via line 147d to combine with the catalyst system flowing in line 152; v) via line 147e to combine with the feedstock mixture flowing in line 191, vi) via 147f to combine with the dispersed feedstock mixture flowing in line 192, or vii) any combination of i)-vi).

When introducing the $C_{3+}$ olefin for a period of time via line 146 and line 147a, the $C_{3+}$ olefin can combine with ethylene flowing in ethylene feed line 142. The ethylene feed line 142 (comprising ethylene, the $C_{3+}$ olefin, and optionally hydrogen) can join with the organic reaction medium (which can be optionally previously combined with scrub agent) line 162 to form the feedstock mixture line 191. That is, in an aspect where the $C_{3+}$ olefin flows in line 147a, the feedstock mixture includes ethylene, organic reaction medium (which can be optionally previously combined with scrub agent), and the $C_{3+}$ olefin (and optionally hydrogen). The feedstock mixture can flow into the optional mixing device 190 where ethylene, the organic reaction medium (which can be optionally previously combined with scrub agent), the $C_{3+}$ olefin, and optionally hydrogen are dispersed in the feedstock mixture. The dispersed components in line 191 can flow from the optional mixing device 190 in the dispersed feedstock mixture line 192 to the reaction zone 110 via the second reaction zone inlet 113. In the aspect where the $C_{3+}$ olefin is introduced via line 146 and line 147a, the $C_{3+}$ olefin can flow via lines 146, 147a, 142, 191, and 192 to the reaction zone 110.

When introducing the $C_{3+}$ olefin for a period of time via line 146 and line 147b, the $C_{3+}$ olefin can combine with the organic reaction medium (which can be optionally previously combined with scrub agent) flowing in the organic reaction medium feed line 162. The organic reaction medium line 162 (comprising the organic reaction medium, the $C_{3+}$ olefin, and optionally scrub agent) can join with the ethylene feed line 142 (comprising ethylene and optionally hydrogen) to form the feedstock mixture line 191. That is, in an aspect where the $C_{3+}$ olefin flows in line 147b, the feedstock mixture in line 191 includes ethylene, organic reaction medium, and the $C_{3+}$ olefin (and optionally scrub agent and/or hydrogen). The feedstock mixture can flow into the optional mixing device 190 where ethylene, the organic reaction medium, and the $C_{3+}$ olefin (and optionally the scrub agent and/or hydrogen) can be dispersed in the feedstock mixture. The dispersed feedstock mixture can flow from the optional mixing device 190 in the dispersed feedstock mixture line 192 to the reaction zone 110 via the second reaction zone inlet 113. In the aspect where the $C_{3+}$ olefin is introduced via line 146 and line 147b, the $C_{3+}$ olefin can flow via lines 146, 147b, 162, 191, and 192 to the reaction zone 110.

When introducing the $C_{3+}$ olefin for a period of time via line 146 and line 147c, the $C_{3+}$ olefin can flow directly to the reaction zone 110 via the reaction zone inlet 115 which is configured to introduce the $C_{3+}$ olefin to the reaction zone 110.

When introducing the $C_{3+}$ olefin for a period of time via line 146 and line 147d, the $C_{3+}$ olefin can combine with the catalyst system flowing in catalyst system feed line 152. In such an aspect, the catalyst system can flow for a period of time with the $C_{3+}$ olefin in line 152 to the reaction zone 110 via the first reaction zone inlet 111. In the aspect where the $C_{3+}$ olefin is introduced via line 146 and line 147d, the $C_{3+}$ olefin can flow via lines 146, 147d, and 152 to the reaction zone 110 via the first reaction zone inlet 111.

When introducing the $C_{3+}$ olefin for a period of time via line 146 and line 147e, the $C_{3+}$ olefin can combine with the feedstock mixture in line 191. In such an aspect, the feedstock mixture entering the optional mixing device 190 can contain the $C_{3+}$ olefin in addition to ethylene, and the organic reaction medium (and optionally the scrub agent and/or hydrogen). In the mixing device 190, ethylene, the organic reaction medium, and the $C_{3+}$ olefin (and optionally scrub agent and/or hydrogen) can be dispersed in the feedstock mixture. The dispersed feedstock mixture flows from the optional mixing device 190 in dispersed feedstock mixture line 192 to the reaction zone 110 via the second reaction zone inlet 113. In the aspect where the $C_{3+}$ olefin is introduced via line 146 and line 147e, the $C_{3+}$ olefin can flow for a period of time via lines 146, 147e, 191, and 192 to the reaction zone 110.

When introducing the $C_{3+}$ olefin for a period of time via line 146 and line 147f, the $C_{3+}$ olefin can combine with the dispersed feedstock mixture in line 192. In such an aspect, the feedstock mixture entering the mixing device 190 can comprise ethylene and organic reaction medium (and optionally scrub agent and/or hydrogen); the dispersed feedstock mixture exiting the optional mixing device 190 can comprise ethylene and the organic reaction medium (optionally scrub agent and/or hydrogen) dispersed in the feedstock mixture; and after line 147c containing the $C_{3+}$ olefin combines with line 192, the dispersed feedstock mixture additionally can comprise the $C_{3+}$ olefin. In certain aspects, the $C_{3+}$ olefin may or may not be dispersed in the dispersed feedstock mixture contained in line 192. The dispersed feedstock mixture additionally containing the $C_{3+}$ olefin can flow to the reaction zone 110 via the second reaction zone inlet 113. In the aspect where the $C_{3+}$ olefin is introduced via line 146 and line 147f, the $C_{3+}$ olefin can flow via lines 146, 147f, and 192 to the reaction zone 110.

With respect to the timing of the flow of the $C_{3+}$ olefin relative to the flow of ethylene for the period of time, the flow of $C_{3+}$ olefin can commence before or simultaneously with the flow of ethylene regardless which of lines 147a, 147b, 147c, 147d, 147e, and/or 147f the $C_{3+}$ olefin flows. Alternatively, the flow of the $C_{3+}$ olefin can commence before the flow of ethylene (when the reaction zone 110 is empty, for example, during hard startup, or when the reaction zone 110 already contains material, for example, in a soft startup after temporary cessation of the flow of ethylene and/or catalyst system to the reaction zone 110 to address process or system issues), then be stopped temporarily, and then again commenced before or at the same time (simultaneously) as the flow of ethylene and/or catalyst system. With respect to the timing of the flow of the $C_{3+}$ olefin relative to the flow of catalyst system for the period of time, the flow of the $C_{3+}$ olefin can commence before, simultaneously, or after the flow of the catalyst system regardless of which lines 147a, 147b, 147c, 147d, 147e, and/or 147f the $C_{3+}$ olefin flows. With respect to the timing of the flow of the $C_{3+}$ olefin relative to the flow of organic reaction medium for the period of time, the flow of the $C_{3+}$ olefin can commence before, simultaneously, or after the flow of the organic reaction medium regardless of which lines 147a, 147b, 147c, 147d, 147e, and/or 147f the $C_{3+}$ olefin flows. With respect to the timing of the flow of the $C_{3+}$ olefin relative to the flow of scrub agent for the period of time, the flow of the $C_{3+}$ olefin can commence before, simultaneously, or after the flow of the scrub agent regardless of which lines 147a, 147b, 147c, 147d, 147e, and/or 147f the $C_{3+}$ olefin flows.

It is noted that in the system 200 of FIG. 2, the feedstock mixture comprising ethylene and at least a portion of the organic reaction medium (in the case of FIG. 2, all of the organic reaction medium used in system 200) can be fed to the reaction zone 110 separately with respect to the catalyst system. That is, the feedstock mixture is fed to the reaction zone 110 via lines 191 and 192 and via second reaction zone inlet 113; while, the catalyst system can be fed to the reaction zone 110 via line 152 and via first reaction zone inlet 111.

The separately fed feedstock mixture in any of lines 191 and 192 is substantially free of the catalyst system or at least a chromium component of the catalyst system. By "substantially free" it is meant that the feedstock mixture has equal to or less than 1.0, 0.9, 0.8, 0.7, 0.6, 0.5, 0.4, 0.3, 0.2, or 0.1 wt. % of the catalyst system present based on weight of the feedstock mixture entering the reaction zone 110.

FIG. 3 shows a process flow diagram of another reaction system 300 according to the present disclosure. The system 300 includes one or more of an ethylene source 140 in fluid communication with an ethylene feed line 142; a catalyst system source 150 in fluid communication with a catalyst system feed line 152; a $C_{3+}$ olefin source 145 in communication with a $C_{3+}$ feed line 146; an organic reaction medium source 160 in fluid communication with an organic reaction medium feed line 162; an optional scrub agent source 170 in communication with a scrub agent feed line 172; an optional hydrogen feed line 144 feeding to the ethylene feed line 142; an optional pump 180; an optional mixing device 190; a reaction zone 110 having a reaction zone inlet 119, an optional reaction zone inlet 115 for $C_{3+}$ olefin, and a reaction zone outlet 117 representing one or more reaction zone outlets; and a heat exchanger 120. It is contemplated that the reaction system 300 of FIG. 3 can include appropriate equipment (e.g., valves, control devices, sensors, electrical writing, insulation) which are not shown in FIG. 3 yet would be included according to those skilled in the art with the aid of this disclosure.

The reaction zone inlet 119 (representing one or more reaction zone inlets) can be configured to introduce the catalyst system and the feedstock mixture to the reaction zone 110, and the reaction zone outlet 117 (representing one or more reaction zone outlets) can be configured to discharge a reaction zone effluent comprising an ethylene oligomer product from the reaction zone 110 via line 118. Valve 130 can be used in line 118 to control a flow of the reaction zone effluent in line 118 and/or to control a pressure of the reaction zone 110. Reaction zone effluent in line 118 can then feed to equipment (not shown) for isolating various streams (e.g., the desired oligomer) from the reaction zone effluent.

An aspect of the disclosed systems and processes is that an optional reaction zone inlet 115 can be configured to introduce the $C_{3+}$ olefin for a period of time to the reaction zone 110. For the reaction zone 110 configuration shown in FIG. 3, the inlets 115 and 119 can be placed as far away from outlet 117. Other considerations for placement of the inlets 115 and 119 as well as outlet 117 may be taken into account, for example, when the reaction zone 110 includes a recycle feature.

The catalyst system can flow through catalyst system feed line 152 from the catalyst system source 150 to combine with an optionally dispersed feedstock mixture (containing the ethylene, organic reaction medium, the catalyst system, optionally hydrogen, and optionally the $C_{3+}$ olefin for a period of time) in line 192. Joining line 152 and line 192 yields combined feed line 193, which in FIG. 3, can feed to the reaction zone 110 via reaction zone inlet 119.

Alternatively (not shown), the catalyst system feed line 152 can combine with the feedstock mixture in line 191, and the feedstock mixture feed line 191 (containing the ethylene, organic reaction medium, the catalyst system, optionally hydrogen, and optionally for a period of time the $C_{3+}$ olefin) can flow directly to the reaction zone 110 via reaction zone inlet 119 or can flow through mixing device 190 to yield a dispersed mixture (containing dispersed feedstock mixture, including ethylene, the organic reaction medium, the catalyst system, optionally hydrogen, and optionally for a period of time the $C_{3+}$ olefin) which subsequently flows to the reaction zone 110 via line 192 and reaction zone inlet 119.

Alternatively (not shown), the catalyst system feed line 152 can combine with the organic reaction medium feed line 162. In such an aspect, the organic reaction medium feed line 162 (containing the organic reaction medium and catalyst system) can join with the ethylene feed line 142 to form the feedstock mixture feed line 191 comprising ethylene, organic reaction medium, catalyst system, optionally hydrogen, and optionally for a period of time the $C_{3+}$ olefin. Line 191 which additionally includes the catalyst system can flow directly to the reaction zone 110 via reaction zone inlet 119 or can flow through mixing device 190 to yield a dispersed feedstock mixture (containing ethylene, the organic reaction medium, the catalyst system, optionally hydrogen, and optionally for a period of time the $C_{3+}$ olefin) which subsequently flows to the reaction zone 110 via line 192 and reaction zone inlet 119.

In any of the above-described alternative catalyst system injection aspects, the $C_{3+}$ olefin for a period of time can combine with the catalyst system feed line 152 prior to the catalyst system feed line 152 joining with any of line 192 (e.g., via line 147d shown FIG. 3), line 191, line 162, or line 142.

The catalyst system feed line 152 can optionally include a solvent and/or diluent along with the catalyst system. The solvent and/or diluent can be any organic reaction medium described herein. In an embodiment, the solvent and/or diluent can be the organic reaction medium utilized in the process. The catalyst system can be dispersed in the solvent and/or diluent in the catalyst system feed line 152. For example, the catalyst system feed line 152 can include a mixing device (not shown), similar to mixing device 190 or in a precontactor apparatus (not shown), which is configured to disperse the catalyst system in the solvent and/or diluent prior to the catalyst system combining with the dispersed feedstock mixture in line 192. When the solvent and/or diluent and the catalyst system are present in the catalyst system feed line 152 in FIG. 3, the chromium:diluent mass ratio can be any disclosed herein.

Organic reaction medium (optionally combined with the catalyst system) can flow in organic reaction medium feed line 162 from the organic reaction medium source 160, through the pump 180, and to the point where the ethylene feed line 142 and the organic reaction medium feed line 162 join.

Similar to the system 200 of FIG. 2, at least a portion of the organic reaction medium in the system 300 of FIG. 3 can be contacted with a scrub agent (e.g., an alkylaluminum compound, any described herein) prior to introduction of the portion of the organic reaction medium to the reaction zone 110. FIG. 3 shows scrub agent can be added via feed line 172 to the organic reaction medium feed line 162 such that the organic reaction medium feed line 162 can contain both the organic reaction medium and the scrub agent. Alternatively, the scrub agent may not be combined with the organic reaction medium in the organic reaction medium feed line 162. The scrub agent is independently disclosed herein and can be utilized to further described reaction system 300.

Likewise, similar to the system 200 of FIG. 2, at least a portion of the organic reaction medium in the system 300 of FIG. 3 can be contacted with the scrub agent (e.g., an alkylaluminum compound) prior to contact of the portion of organic reaction medium with ethylene. FIG. 3 shows the co-catalyst can be added via line 172 to the organic reaction medium feed line 162, before the organic reaction medium contacts ethylene via combination of the organic reaction medium feed line 162 with the ethylene feed line 142. Alternatively, the scrub agent may not be combined with the organic reaction medium in the organic reaction medium feed line 162. The scrub agent is independently disclosed herein and can be utilized to further described reaction system 300.

In FIG. 3, all of the organic reaction medium can be fed to the reaction zone via line 162. However, as is discussed herein, it is contemplated that only a portion of the total amount of organic reaction medium which is used in the system 300 is in line 162 and optionally contacted with the scrub agent prior to introduction to the reaction zone 110; e.g., the other portions can be mixed with the catalyst system in catalyst system feed line 152 and/or can be included in a bypass line which can feed directly to the reaction zone 110. Alternatively, the scrub agent may not be combined with the organic reaction medium, and the organic reaction medium feed line 162 can flow directly to the suction side 181 of pump 180.

Ethylene (which can be optionally combined with the $C_{3+}$ olefin for a period of time, and/or option combined with hydrogen and/or the catalyst system) can flow in ethylene feed line 142 from the ethylene source 140 and can combine with organic reaction medium (which is optionally previously combined with scrub agent, $C_{3+}$ olefin, and/or catalyst system) flowing in line 162 on the head side 182 of the pump 180. Alternatively, ethylene can be combined with the organic reaction medium flowing in line 162 on the suction side 181 of the pump 180.

Combination of the ethylene in line 142 with the organic reaction medium in line 162 yields a feedstock mixture in feedstock mixture line 191. The feedstock mixture flows through an optional mixing device 190 where ethylene and the organic reaction medium (which can be optionally previously combined with scrub agent and/or $C_{3+}$ olefin) can be dispersed, and subsequently flow as a dispersed feedstock mixture in dispersed feedstock mixture line 192.

The feedstock mixture can be contacted with the catalyst system prior to introduction of the feedstock mixture into the reaction zone 110. In FIG. 3, the feedstock mixture in the form of dispersed feedstock mixture in line 192 can combine with the catalyst system in line 152 to form a combined feed line 193 which can flow to the reaction zone inlet 119 and feeds to the reaction zone 110. Alternatively, the feedstock mixture can be contacted with the catalyst system in line 152 via combination with line 191 and before the feedstock mixture enters the optional mixing device 190.

Hydrogen optionally can be used to control oligomerization reactions. The optional hydrogen can be fed into the ethylene feed line 142 of reaction system 300 via hydrogen feed line 144. The combination of hydrogen with ethylene in the ethylene feed line 144 can be upstream of valve 143 as shown in FIG. 3; or alternatively, downstream of valve 143. While the hydrogen feed line 144 in FIG. 3 is shown as feeding to the ethylene feed line 142, it is contemplated that the hydrogen feed line 144 can fluidly connect to any reaction zone inlet (e.g., reaction zone inlet 115 or reaction zone inlet 119) directly or via another line (e.g., line 146, line 147*a*, *b*, *c*, *d*, *e*, *f*, or *g*, line 152, line 162, line 172, line 191, line 192, or line 193).

The $C_{3+}$ olefin can be introduced, for a period of time, to the reaction system 300 via any one or more of lines 147*a-g* (the alternative nature being shown as dashed lines in FIG. 3). For example, the $C_{3+}$ olefin, which can be introduced/fed for a period of time to the reaction zone, can flow from the $C_{3+}$ olefin source 145 via line 146 and: i) via line 147*a* to combine with ethylene flowing in ethylene feed line 142, before ethylene joins with organic reaction medium flowing in feed line 162 to form the feedstock mixture in feedstock mixture line 191, ii) via line 147*b* to combine with the organic reaction medium flowing in line 162, before the organic reaction medium joins with ethylene to form the feedstock mixture in line 191, iii) via line 147*c* to add the $C_{3+}$ olefin directly to the reaction zone 110 via optional reaction zone inlet 115, iv) via line 147*d* to combine with the catalyst system flowing in line 152; v) via line 147*e* to combine with the feedstock mixture flowing in line 191, vi) via line 147*f* to combine with the dispersed feedstock mixture flowing in line 192, vii) via line 147*g* to combine with the components of the combined feedstock mixture 193 before entry into the reaction zone 110 via reaction zone inlet 119, or viii) any combination of i)-vii).

When introducing the $C_{3+}$ olefin for a period of time via line 146 and line 147*a*, the $C_{3+}$ olefin can combine with ethylene flowing in ethylene feed line 142. The ethylene feed line 142 (comprising ethylene, the $C_{3+}$ olefin, optionally hydrogen, and optionally catalyst system) can join with the organic reaction medium (which can be optionally previously combined with scrub agent) line 162 to form the feedstock mixture line 191. That is, in an aspect where the $C_{3+}$ olefin flows in line 147*a*, the feedstock mixture includes ethylene, organic reaction medium (which can optionally previously combined with the scrub agent), and the $C_{3+}$ olefin (and optionally hydrogen, and optionally the catalyst system). The feedstock mixture feed line 191 can flow into the optional mixing device 190 where the components in line 191 are dispersed. The dispersed components (e.g., the dispersed feedstock mixture) can flow from the optional mixing device 190 in the dispersed line 192. In aspects where the catalyst system has not previously been joined to a line upstream of the reaction zone inlet 119, the components in dispersed line 192 can join with the catalyst feed line 152 to form the combined feed line 193 which contains the dispersed components of line 191 and the catalyst system. Line 193 subsequently can flow to the reaction zone 110 via the reaction zone inlet 119. In the aspect where the $C_{3+}$ olefin is introduced via line 146 and line 147a, the $C_{3+}$ olefin can flow via lines 146, 147a, 142, 191, 192, and 193 to the reaction zone 110.

When introducing the $C_{3+}$ olefin for a period of time via line 146 and line 147b, the $C_{3+}$ olefin can combine with the organic reaction medium (which can be optionally previously combined with scrub agent) flowing in the organic reaction medium feed line 162. The organic reaction medium line 162 (comprising the organic reaction medium, the $C_{3+}$ olefin, optionally catalyst system, and/or optionally scrub agent) can join with the ethylene feed line 142 (comprising ethylene and optionally hydrogen) to form the feedstock mixture line 191. That is, in an aspect where the $C_{3+}$ olefin flows in line 147b, the feedstock mixture in line 191 includes ethylene, organic reaction medium, and the $C_{3+}$ olefin (optionally scrub agent, optionally hydrogen, and/or optionally catalyst system). The feedstock mixture feed line 191 can flow into the optional mixing device 190 where the components in line 191 can be dispersed. The dispersed components (e.g., the dispersed feedstock mixture) can flow from the optional mixing device 190 in the dispersed line 192. In aspects where the catalyst system has not previously been joined to a line upstream of the reaction zone inlet 119, the components in dispersed line 192 can join with the catalyst system feed line 152 to form the combined feed line 193 which contains the dispersed components of line 191 and the catalyst system. Line 193 subsequently can flow to the reaction zone 110 via the reaction zone inlet 119. In the aspect where the $C_{3+}$ olefin is introduced via line 146 and line 147b, the $C_{3+}$ olefin can flow via lines 146, 147b, 162, 191, 192, and 193 to the reaction zone 110.

When introducing the $C_{3+}$ olefin for a period of time via line 146 and line 147c, the $C_{3+}$ olefin can flow directly to the reaction zone 110 via the reaction zone inlet 115 which is configured to introduce the $C_{3+}$ olefin to the reaction zone 110.

When introducing the $C_{3+}$ olefin for a period of time via line 146 and line 147d, the $C_{3+}$ olefin can combine with the catalyst system flowing in catalyst system feed line 152. In such an aspect, the catalyst system can flow for a period of time with the $C_{3+}$ olefin in line 152 to join with the feedstock mixture outside the reaction zone 110. In FIG. 3, line 152 combines with the dispersed feedstock mixture in line 192 to form the combined feed stream 193, which flows to the reaction zone 110 via the reaction zone inlet 119. In the aspect where the $C_{3+}$ olefin is introduced via line 146 and line 147d, the $C_{3+}$ olefin can flow via lines 146, 147d, 152, and 193 to the reaction zone 110 via the reaction zone inlet 119.

When introducing the $C_{3+}$ olefin for a period of time via line 146 and line 147e, the $C_{3+}$ olefin can combine with the feedstock mixture in line 191. The feedstock mixture feed line 191 can flow into the optional mixing device 190 where the components (including $C_{3+}$ olefin) in line 191 can be dispersed. The dispersed components (e.g., the dispersed feedstock mixture) can flow from the optional mixing device 190 in dispersed line 192. In aspects where the catalyst system has not previously been joined to a line upstream of the reaction zone inlet 119, the components in dispersed line 192 can join with the catalyst system feed line 152 to form the combined feed line 193 which contains the dispersed components of line 191 and the catalyst system. Line 193 subsequently can flow to the reaction zone 110 via the reaction zone inlet 119. In the aspect where the $C_{3+}$ olefin can be introduced/fed for a period of time via line 146 and line 147e, the $C_{3+}$ olefin can flow via lines 146, 147e, 191, 192, and 193 to the reaction zone 110.

When introducing the $C_{3+}$ olefin for a period of time via line 146 and line 147f, the $C_{3+}$ olefin can combine with the dispersed feedstock mixture in line 192. In such an aspect, the feedstock mixture entering the mixing device 190 can comprise ethylene, organic reaction medium (optionally, scrub agent, hydrogen, and/or catalyst system. The dispersed components (e.g., the dispersed feedstock mixture) can flow from the optional mixing device 190 in dispersed line 192. Line 147f containing the $C_{3+}$ olefin can combine with dispersed line 192. In aspects where the catalyst system has not previously been joined to a line upstream of the reaction zone inlet 119, the components (including the $C_{3+}$ olefin) in dispersed line 192 can join with the catalyst system feed line 152 to form the combined feed line 193 which can contain the components of line 192 (e.g., the dispersed feedstock mixture and $C_{3+}$ olefin) and the catalyst system. Line 193 subsequently can flow to the reaction zone 110 via the reaction zone inlet 119. In the aspect where the $C_{3+}$ olefin is introduced via line 146 and line 147f, the $C_{3+}$ olefin can flow via lines 146, 147f, 192, and 193 to the reaction zone 110.

When introducing the $C_{3+}$ olefin for a period of time via line 146 and line 147g, the $C_{3+}$ olefin can combine with the combined feed components in combined feed line 193. In the aspect where the $C_{3+}$ olefin for a period of time is introduced/fed via line 146 and line 147g, the $C_{3+}$ olefin can flow via lines 146, 147g, and 193 to the reaction zone 110.

With respect to the commencement of the flow of the $C_{3+}$ olefin relative to the commencement of the flow of ethylene for the period of time, the flow of $C_{3+}$ olefin can commence before or simultaneously with the flow of ethylene regardless which of lines 147a, 147b, 147c, 147d, 147e, 147f, and/or 147g the $C_{3+}$ olefin flows. Alternatively, the flow of the $C_{3+}$ olefin can commence before the flow of ethylene (when the reaction zone 110 is empty, for example, during hard startup, or when the reaction zone 110 already contains material, for example, in a soft startup after temporary cessation of the flow of ethylene and/or catalyst system to the reaction zone 110 to address process or system issues), then be stopped temporarily, and then again commenced before or at the same time (simultaneously) as the flow of ethylene and/or catalyst system.

With respect to the commencement of the flow of the $C_{3+}$ olefin relative to the commencement of the flow of catalyst system for the period of time, the flow of the $C_{3+}$ olefin can commence before, simultaneously, or after the flow of the catalyst system regardless of which lines 147a, 147b, 147c, 147d, 147e, 147f, and/or 147g the $C_{3+}$ olefin flows.

With respect to the commencement of the flow of the $C_{3+}$ olefin relative to the commencement of the flow of organic reaction medium for the period of time, the flow of the $C_{3+}$ olefin can commence before, simultaneously, or after the flow of the organic reaction medium regardless of which lines 147a, 147b, 147c, 147d, 147e, 147f, and/or 147g the $C_{3+}$ olefin flows.

With respect to the commencement of the flow of the $C_{3+}$ olefin relative to the commencement of the flow of scrub agent for the period of time, the flow of the $C_{3+}$ olefin can commence before, simultaneously, or after the flow of the scrub agent regardless of which lines 147a, 147b, 147c, 147d, 147e, 147f, and/or 147g the $C_{3+}$ olefin flows.

Reaction zone 110 in FIGS. 1-3 is shown as a single continuous stirred-tank reactor operating in continuous mode with a continuous stirred-tank configuration. Various alternative configurations and/or operating modes that can achieve desired ethylene oligomerization results are contemplated for the reaction zone 110 and are discussed in more detail herein. In FIGS. 1-3, thermocouple 114 can read the temperature of the reaction zone 110 as the reaction proceeds. Stirrer 116 of FIGS. 1-3 operated by motor 112 can agitate the contents of the reaction zone 110. The stirrer 116 of FIGS. 1-3 can be an impeller coupled to the motor 112 via a rod. Heat exchanger 120 of FIGS. 1-3 can receive line 122 and can provide line 124 to the reaction zone 110 in order to maintain a temperature of the reaction zone 110.

A reaction zone effluent comprising ethylene oligomer product formed in the reaction zone 110 in FIGS. 1-3 can flow in line 118 from reaction zone outlet 117. In some embodiments, the ethylene oligomer product in line 118 can flow to the product recovery zone (not shown). The product recovery zone can include catalyst system deactivation, an ethylene oligomer product separation where the ethylene oligomer product (e.g., hexenes and/or octenes) can be recovered from the reaction zone effluent via techniques known in the art with the aid of this disclosure (e.g., distillation, flashing, absorption, stripping), by-product separation and/or isolation, and/or any steps which can facilitate the handling of the reaction zone effluent and the isolation of the desired ethylene oligomers.

The reaction zone of any process, system and/or reaction system (e.g., reaction zone 110 of the figures) can comprise any reactor which can oligomerize ethylene to an ethylene oligomer product. In an embodiment, the reaction zone of any process, system, or reaction system described herein can comprise a stirred tank reactor, a plug flow reactor, or any combination thereof; alternatively, a stirred tank reactor; or alternatively, a plug flow reactor. In an embodiment, the reaction zone of any process, system, or reaction system described herein can comprise an autoclave reactor, a continuous stirred tank reactor, a loop reactor, a gas phase reactor, a solution reactor, a tubular reactor, a recycle reactor, a bubble reactor, or any combination thereof; alternatively, an autoclave reactor; alternatively, a stirred tank reactor; alternatively, a loop reactor; alternatively, a gas phase reactor; alternatively, a solution reactor; alternatively, a tubular reactor; alternatively, a recycle reactor; or alternatively, a bubble reactor. In some embodiments, the reaction zone can comprise multiple reactor; or alternatively, only on reactor. When multiple reactors are present, each of the reactors can be the same or different types of reactors. The reaction zone (e.g., reaction zone 110) can comprise single or multiple reactors of any of the types disclosed herein operating in batch or continuous mode; alternatively, continuous mode.

Aspects and/or embodiments of the processes, systems, and/or reaction systems described herein can utilize a pump. In an embodiment, the pump can be any pump which can pump the organic reaction medium to the reaction zone. Generally, the pump can have a suction side which receives the organic reaction medium and a head side which provides the organic reaction medium at a pressure suitable for flow to the reaction zone. FIG. 1, FIG. 2, and FIG. 3 provide non-liming examples of reaction systems which can utilize a pump 180 having suction side 181 and head side 182. In FIG. 1, pump 180 is in fluid communication with the reaction zone inlet 215. In FIG. 2, pump 180 is in fluid communication with the reaction zone inlet 113. In FIG. 3, pump 180 is in fluid communication with reaction zone inlet 119. FIG. 1, FIG. 2, and FIG. 3 show that pump 180 can be located upstream of the point where ethylene (e.g., from the ethylene feed line 142) and the organic reaction medium (e.g., from the organic reaction medium feed line 162 which optionally contains scrub agent and/or catalyst system) join/combine to form the feedstock mixture. Feeding ethylene in this configuration can reduce flashing and recompression. In an embodiment, the pump 180 can be configured to receive the catalyst system and/or the scrub agent combined with the organic reaction medium on the suction side 181 of the pump 180; alternatively, the catalyst system and/or the scrub agent can be combined with the organic reaction medium on the head side 182 of the pump 180; alternatively, the catalyst system can be combined with the organic reaction medium on the suction side 181 of the pump 180 while the scrub agent can be combined with the organic reaction medium and catalyst system on the head side 182 of the pump; alternatively, the scrub agent can be combined with the organic reaction medium on the suction side 181 of the pump 180 while the catalyst system can be combined with the organic reaction medium and scrub agent on the head side 182 of the pump 180. In the system 300 in FIG. 3, pump 180 can be configured to receive the catalyst system combined with the organic reaction medium on the suction side 181 and to pump the catalyst system combined with the organic reaction medium and optional scrub agent on the head side 182 of the pump 180.

In configurations where the reaction zone 110 has a recycle features, a pump can be included in the path of the reaction zone 110 suitable for passing contents of the reaction zone 110 to heat exchangers. For example a pump suitable for pumping reaction zone contents can be placed in line 122 of FIG. 1, FIG. 2, or FIG. 3 to pass the contents to the heat exchanger 120.

Aspects and/or embodiments of the processes, systems, and/or reaction systems described herein can utilize a mixing device to mix/disperse the ethylene and the organic reaction medium. In an embodiment, the mixing device can be any device which can mix/disperse the organic reaction medium and ethylene in the feedstock mixture. Such mixing/dispersing can be implemented to minimize areas of high ethylene concentration within the feedstock mixture. The mixing device can provide mixing of ethylene and the organic reaction medium via agitation of the flow there through. For example, the mixing device can be a static mixer having fixed baffles (e.g., in a helical arrangement, or any other baffle arrangement) placed within a housing, where the baffles continuously blend the ethylene and organic reaction medium to disperse the ethylene and the organic reaction medium in the feedstock mixture. Alternatively, the mixing device can have moving parts such as a propeller or impeller. FIG. 2 shows an optional mixing device 190 that can be positioned between i) the joining of the ethylene feed line 142 and the organic reaction medium feed line 162 and ii) the second reaction zone inlet 113 such that ethylene and the organic reaction medium are dispersed in the feedstock mixture prior to the feedstock mixture entering the reaction zone 110. FIG. 3 shows an optional mixing device 190 can be positioned between i) the joining of the ethylene feed line 142 and the organic reaction medium feed line 162 and ii) the reaction zone inlet 119 such that ethylene and the organic reaction medium are dispersed in the feedstock mixture prior to the ethylene feedstock combining with the catalyst system and prior to the feedstock mixture entering the reaction zone 110. In some embodiments, the mixing/dispersion of the ethylene and the organic reaction medium can be accomplished using a precontactor device such a vessel with a mixing device.

Lines 118, 122, 124, 142, 146, 147a-g, 152, 162, 172, 191, 192, and 193 shown in the figures can be appropriate metal piping or tubing for ethylene oligomerization reaction system components.

The reaction zone inlets 111, 113, 115, 119, 213, and 215 as well as the reaction zone outlet 117, shown in the figures can be in the form of flanges and/or appropriate piping and valves for receiving the various feed components and removing the reaction zone effluent from the reaction zone 110. The reaction zone outlet 117 can be one or more physical outlets. For example, the reaction zone 110 shown in FIG. 1, FIG. 2, and FIG. 3 can have one outlet 117; alternatively, the reaction zone 110 can have one or more other outlets in addition to outlet 117; alternatively, the reaction zone 110 can include multiple reactors, each having a single outlet or multiple outlets which amount to more than one outlet for the collection of multiple reactors which define the reaction zone 110. Additionally, each reaction zone inlet which is shown as a single reaction zone inlet can represent one or more reaction inlets feeding the designated materials to the reaction zone.

Ethylene for any of the processes, systems, and/or reaction systems described herein (e.g., ethylene source 140) can be oligomerization or polymerization grade ethylene. By "oligomerization or polymerization grade ethylene" it is meant that ethylene is present in ethylene feed line 142 in an amount of at least 98.0, 98.5, 99.0, 99.1, 99.2, 99.3, 99.4, 99.5, 99.6, 99.7, 99.8, 99.9, 99.99, 99.999 mol % based on the total moles of components in the ethylene composition (e.g., ethylene feed line 142). The ethylene for any of the processes, systems, and/or reaction systems (e.g., ethylene source 140) can be any source of oligomerization or polymerization grade ethylene, for example, a storage tank or a line from a cracking process, monomer recovery process, and the like. In an embodiment of the processes, systems, and/or reaction systems (e.g., reaction systems 100 and 200) disclosed herein, substantially all of the ethylene can be contacted with the catalyst system and/or introduced/fed to the reaction zone (e.g., reaction zone 110) via the feedstock mixture. By "substantially all" it is meant that at least 99.0, 99.1, 99.2, 99.3, 99.4, 99.5, 99.6, 99.7, 99.8, 99.9, 99.99, 99.999 mol % of the total ethylene in system 200 or 300 can be fed to the reaction zone via the feedstock mixture.

The $C_{3+}$ olefin can be one or a combination of olefins having three or more carbon atoms. In an aspect, the $C_{3+}$ olefin can be a $C_3$ to $C_{18}$ olefin, a $C_4$ to $C_{14}$ olefin, or a $C_6$ to $C_{12}$ olefin. In an embodiment, any olefin which can be utilized in the processes, systems, and/or reaction systems described herein can be an internal olefin, or an alpha olefin. In some embodiments, the internal olefin or alpha olefin can be branched or linear; alternatively, branched; or alternatively, linear. In some embodiments, as the $C_{3+}$ olefin any olefin which can be utilized in the processes, systems, and/or reaction systems described herein can be a normal alpha olefin. Suitable non-limiting examples of the $C_{3+}$ olefin include one or more of propylene, butene, pentene, hexene, heptene, octene, nonene, decene, undecene, dodecene, tridecene, tetradecene, pentadecene, hexadecene, heptadecene, octadecene, or any combination thereof. In an embodiment, the $C_{3+}$ olefin can comprise iso-butene. In an embodiment, the $C_{3+}$ olefin can comprise, or consist essentially of, propene, 1-butene, 1-hexene, 1-octene, 1-decene, 1-dodecene, 1-tetradecene, 1-hexedecene, 1-octacene, or any combination thereof; alternatively, 1-butene, 1-hexene, 1-octene, 1-decene, 1-dodecene, 1-tetradecene, or any combination thereof; alternatively, 1-hexene, 1-octene, 1-decene, 1-docene, or any combination thereof; alternatively, 1-hexene, 1-octene, or any combination thereof; alternatively, propene; alternatively, 1-butene; alternatively, 1-hexene; alternatively, 1-octene; alternatively, 1-decene; or alternatively, 1-dodecene. The $C_{3+}$ olefin source (e.g., $C_{3+}$ olefin source 145) for the processes, systems, and/or reaction systems disclosed herein can be any source of olefin(s) described herein, including a recycle line which flows a $C_{3+}$ olefin recovered from an ethylene oligomer product to the $C_{3+}$ olefin feed line 146.

The processes, systems, and/or reaction systems described herein can use an organic reaction medium. Generally, the organic reaction can act as a solvent or a diluent in the processes described herein. In an aspect, the organic reaction medium can be a hydrocarbon, a halogenated hydrocarbon, or a combination thereof, for example. Hydrocarbons and halogenated hydrocarbons which can be used as an organic reaction medium can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as an organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as an organic reaction medium can be cyclic or acyclic and/or can be linear or branched, unless otherwise specified. Non-limiting examples of suitable acyclic aliphatic hydrocarbon organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbons which can be used as an organic reaction medium include cyclohexane, and methyl cyclohexane, for example. Aromatic hydrocarbons which can be useful as an organic reaction medium include $C_6$ to $C_{10}$ aromatic hydrocarbons. Non-limiting examples of suitable aromatic hydrocarbons that can be utilized singly or in any combination as an organic reaction medium include benzene, toluene, xylene (including ortho-xylene, meta-xylene, para-xylene, or mixtures thereof), ethylbenzene, or combinations thereof. Halogenated aliphatic hydrocarbons which can be useful as an organic reaction medium include $C_1$ to $C_{15}$ halogenated aliphatic hydrocarbons, $C_1$ to $C_{10}$ halogenated aliphatic hydrocarbons, or $C_1$ to $C_5$ halogenated aliphatic hydrocarbons, for example. The halogenated aliphatic hydrocarbons which can be used as an organic reaction medium can be cyclic or acyclic and/or can be linear or branched, unless otherwise specified. Non-limiting examples of suitable halogenated aliphatic hydrocarbons which can be utilized as an organic reaction medium include methylene chloride, chloroform, carbon tetrachloride, dichloroethane, trichloroethane, and combinations thereof. Halogenated aromatic hydrocarbons which can be useful as an organic reaction medium include $C_6$ to $C_{20}$ halogenated aromatic hydrocarbons, or $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of organic reaction medium can be made on the basis of convenience in processing. For example, isobutane can be chosen to be compatible with solvents and diluents used in processes using the product(s) of the process described herein (e.g., using the product for the formation of polymer in a subsequent processing step). In some embodiments, the organic reaction medium can be chosen to be easily separable from the one or more of the oligomer in the ethylene oligomer product. In some embodiments, an oligomer of the ethylene oligomer product can be utilized as the reaction system solvent. For example, when 1-hexene is an oligomer of an ethylene trimerization process, 1-hexene can be chosen as the reaction system solvent to decrease the need for separation.

The organic reaction medium source (e.g., organic reaction medium source 160) can be any source for an organic reaction medium, including a storage tank of the organic reaction medium and any line from an oligomerization process, a polymerization process, monomer recovery process, and the like.

While in FIG. 1, FIG. 2, and FIG. 3 the entire supply of organic reaction medium is shown flowing in line 162 from the organic reaction medium source 160 to the reaction zone 110, it is contemplated that only a portion of the total amount of organic reaction medium used in systems 100, 200, and 300 flows in line 162, and that a bypass line can be alternatively utilized to flow another portion of the organic reaction medium (e.g., a portion which is not combined with any other reaction component) directly to the reaction zone 110 and in parallel flow to line 162. Additionally or alternatively, a portion of the total amount of organic reaction medium in the system 100, 200, or 300 can be utilized in the catalyst system feed line 152. That is, a portion of the organic reaction medium can be used to dilute or act as a carrying fluid for the catalyst system in catalyst system feed line 152.

As described herein, aspects and embodiments of the disclosed processes, systems, and/or reaction systems can include combining ethylene and an organic reaction medium to form a feedstock mixture. The minimum ethylene concentration in the feedstock mixture can be 4 mass %, 10 mass %, 25 mass %, 35 mass %, or 40 mass % based upon the total mass in the feedstock mixture; alternatively or additionally, at a maximum ethylene concentration of the feedstock mixture can be 65 mass %, 60 mass %, 55 mass %, 50 mass %, 48 mass % based upon the total mass in the reaction zone. In an embodiment, ethylene concentration in the feedstock mixture can from any minimum ethylene concentration in the feedstock mixture disclosed herein to any maximum ethylene concentration in the feedstock mixture disclosed herein. In some non-limiting embodiments, the ethylene concentration in the feedstock mixture can be in a range of from 4 mass % to 60 mass %, from 10 mass % to 60 mass %, from 25 mass % to 55 mass %, 35 mass % to 50 mass %, or 40 mass % to 48 mass % based upon the total mass in the reaction zone. Other ethylene concentrations in the feedstock mixture ranges that can be utilized are readily apparent to those skilled in the art with the aid of this disclosure.

Aspects and embodiments of this invention of the herein described processes, systems, and/or reaction systems can utilize a catalyst system comprising i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and ii) an aluminoxane. In some embodiments, the catalyst system can comprise i) a chromium component comprising an $N^2$-phosphinyl formamidine chromium compound complex and ii) an aluminoxane; alternatively, i) a chromium component comprising an $N^2$-phosphinyl amidine chromium compound complex and ii) an aluminoxane; or alternatively, i) a chromium component comprising an $N^2$-phosphinyl guanidine chromium compound complex and ii) an aluminoxane. Generally, the $N^2$-phosphinyl amidine chromium compound complex, the $N^2$-phosphinyl formamidine chromium compound complex, the $N^2$-phosphinyl guanidine chromium compound complex, the aluminoxane, and any other element of the catalyst system described herein are independent elements of the catalyst systems. These catalyst system elements are independently described herein and can be utilized without limitation, and in any combination, to further describe a catalyst system utilized in aspects and/or embodiments of the processes, systems, and/or reaction systems described herein.

In an embodiment, the $N^2$-phosphinyl formamidine chromium compound complex utilized in the catalyst systems described herein can comprise, can consist essentially of, or can be, a $N^2$-phosphinyl formamidine chromium compound complex having the Structure NPFCr1. In an embodiment, the $N^2$-phosphinyl amidine chromium compound complex utilized in the catalyst systems described herein can comprise, can consist essentially of, of can be, a $N^2$-phosphinyl amidine chromium compound complex having the Structure NPACr1. In an embodiment, the $N^2$-phosphinyl guanidine chromium compound complex utilized in the catalyst systems described herein can comprise, can consist essentially of, or can be, a $N^2$-phosphinyl guanidine chromium compound complex having the Structure GuCr1, GuCr2, GuCr3, GuCr4, or GuCr5; alternatively, alternatively, a $N^2$-phosphinyl guanidine chromium compound complex having the Structure GuCr1; alternatively, a $N^2$-phosphinyl guanidine chromium compound complex having the Structure GuCr2; alternatively, a $N^2$-phosphinyl guanidine chromium compound complex having the Structure GuCr3; alternatively, a $N^2$-phosphinyl guanidine chromium compound complex having the Structure GuCr4; or alternatively, a $N^2$-phosphinyl guanidine chromium compound complex having the Structure GuCr5.

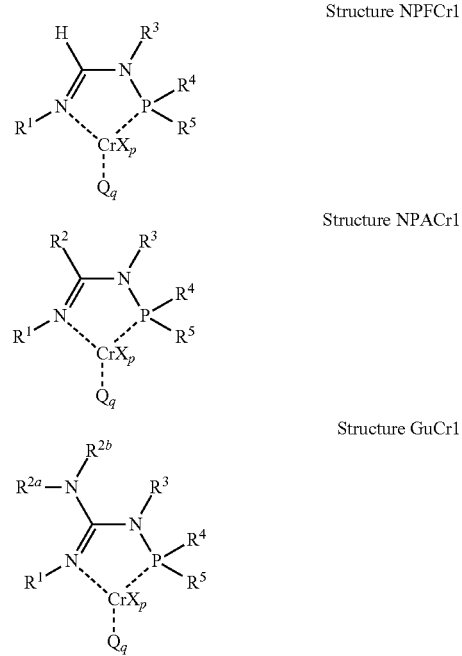

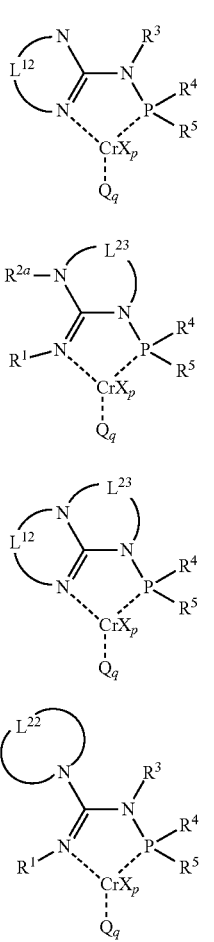

Structure GuCr2

Structure GuCr3

Structure GuCr4

Structure GuCr5

Within the $N^2$-phosphinyl formamidine chromium compound complexes and the $N^2$-phosphinyl amidine chromium compound complexes, the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidine chromium compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidine transition metal complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

$R^1$, $R^3$, $R^4$, and $R^5$ within the $N^2$-phosphinyl formamidine chromium compound complexes having Structure NPFCrl, the $N^2$-phosphinyl amidine chromium compound complexes having Structure NPACrl, and the $N^2$-phosphinyl guanidine chromium compound complexes having the Structures GuCr1, GuCr2, GuCr3, GuCr4, and/or GuCr5 are independently described herein and can be utilized without limitation to further describe the $N^2$-phosphinyl formamidine chromium compound complexes having Structure NPFCrl, the $N^2$-phosphinyl amidine chromium compound complexes having Structure NPACrl, and/or the $N^2$-phosphinyl guanidine chromium compound complexes having the Structures GuCr1, GuCr2, GuCr3, GuCr4, and/or GuCr5. Similarly, $R^2$ within the $N^2$-phosphinyl amidine chromium compound complexes having Structure NPACrl are independently described herein and can be utilized without limitation to further describe the $N^2$-phosphinyl amidine chromium compound complexes having Structure NPACrl. Similarly, $R^{2a}$, $R^{2b}$, $L^{12}$, $L^{22}$, and $L^{23}$ within the $N^2$-phosphinyl guanidine chromium compound complexes having the Structures GuCr1, GuCr2, GuCr3, GuCr4, or GuCr5 are independently described herein and can be utilized without limitation to further describe the $N^2$-phosphinyl guanidine chromium compound complexes having the Structures GuCr1, GuCr2, GuCr3, GuCr4, and/or GuCr5. $MX_p$, Q, and q of the $N^2$-phosphinyl formamidine chromium compound complexes, the $N^2$-phosphinyl amidine chromium compound complexes, and the $N^2$-phosphinyl guanidine chromium compound complexes are independently described herein and can be utilized in any combination, and without limitation, to further describe the $N^2$-phosphinyl formamidine chromium compound complexes, the $N^2$-phosphinyl amidine chromium compound complexes, and the $N^2$-phosphinyl guanidine chromium compound complexes. Additionally, $MX_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complexes, the $N^2$-phosphinyl amidine chromium compound complexes, and the $N^2$-phosphinyl guanidine chromium compound complexes described herein which have an $R^1$, $R^2$, $R^{2a}$, $R^{2b}$, $R^3$, $R^4$, $R^5$, $L^{12}$, $L^{22}$, and/or $L^{23}$.

Generally, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an organyl group; alternatively, an organyl group consisting essentially of inert functional groups; or alternatively, a hydrocarbyl group. In an embodiment, the $R^1$ organyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group. In an embodiment, the $R^1$ organyl group consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^1$ hydrocarbyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ hydrocarbyl group.

In an embodiment, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group. In some embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^1$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^1$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^1$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^1$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^1$ can be a $C_6$ to $C_{20}$ a $C_6$ to $C_{15}$, or a $C_6$ to $C_{10}$ aryl group. In any aspect or embodiment disclosed herein, the substituted aryl group which can be utilized as $R^1$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^1$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^1$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$.

In an embodiment, $R^1$ can be a methyl group, an ethyl group, a propyl group, a butyl group, a pentyl group, a hexyl group, a heptyl group, or an octyl group. In some embodiments, one or more of $R^1$ can be a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an embodiment, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^1$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting embodiments, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general and specific), and/or dialkylcyclopentyl groups (general and specific) which can be utilized as $R^1$. Generally, the alkyl substituents of a disubstituted cyclohexyl group or a dialkylcyclopentyl group can be the same; or alternatively, the alkyl substituents of a dialkylcyclohexyl group or a dialkylcyclopentyl group can be different. In some non-limiting embodiments, any one or more of $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, one or more of $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^1$ can be a phenyl group, a substituted phenyl group; alternatively, a phenyl group; or alternatively, a substituted phenyl group. In an embodiment, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting embodiment, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting embodiments, one or more of $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^1$ can be a phenyl group, a 2-alkoxyphenyl group, or a 4-alkoxyphenyl group. In some non-limiting embodiments, $R^1$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiment, $R^1$ can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^1$ can be a phenyl group, a 2-fluorophenyl group, a 4-fluorophenyl group, or a 2,6-difluorophenyl group.

In an embodiment, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidine chromium compound complexes can be an organyl group; alternatively, an organyl group consisting essentially of inert functional groups; or alternatively, a hydrocarbyl group. In an embodiment, $R^2$ organyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group. In an embodiment, $R^2$ organyl group consisting essentially of inert functional groups of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, $R^2$ hydrocarbyl group of the $N^2$-phosphinyl amidine chromium compound complexes can be a $C_1$ to $C_{20}$, a $C_1$ to $C_{15}$, a $C_1$ to $C_{10}$, a $C_1$ to $C_5$ hydrocarbyl group.

In an embodiment, $R^2$ of the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group. In some embodiments, $R^2$ of the $N^2$-phosphinyl amidine chromium compound complexes can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^2$ of the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^2$ can be a $C_1$ to $C_{20}$, a $C_1$ to $C_{10}$, or $C_1$ to $C_5$ alkyl group. In any aspect or embodiment disclosed herein, alkyl group; alternatively, a $C_1$ to, or a $C_1$ to $C_5$ substituted alkyl group. In any aspect or embodiment disclosed herein, the cycloalkyl group which can be utilized as $R^2$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^2$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^2$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^2$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^2$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^2$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an embodiment, $R^2$ can be a methyl group, an ethyl group, a propyl group, a butyl group, a pentyl group, a hexyl group, a heptyl group, or an octyl group. In some embodiments, one or more of $R^2$ can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an embodiment, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized as $R^2$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting embodiments, $R^2$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, any one or more of $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, one or more of $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^2$ can be a phenyl group, a substituted phenyl group; alternatively, a phenyl group; or alternatively, a substituted phenyl group. In an embodiment, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general or specific), and substituent hydrocarboxy groups (general or specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting embodiment, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting embodiments, one or more of $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^2$ can be a phenyl group, a 2-alkoxyphenyl group, or a 4-alkoxyphenyl group. In some non-limiting embodiments, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiments, $R^2$ can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^2$ can be a phenyl group, a 2-fluorophenyl group, a 4-fluorophenyl group, or a 2,6-difluorophenyl group.

In an embodiment, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

Generally, $R^{2a}$ and/or $R^{2b}$, of the $N^2$-phosphinyl guanidine chromium compound complexes which have an $R^{2a}$ and/or $R^{2b}$ group, independently can be hydrogen or an organyl group; alternatively, hydrogen; or alternatively, an organyl group. In another aspect, $R^{2a}$ and/or $R^{2b}$, of the $N^2$-phosphinyl guanidine chromium compound complexes which have an $R^{2a}$ and/or $R^{2b}$ group, independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$, of the $N^2$-phosphinyl guanidine chromium compound complexes which have an $R^{2a}$ and/or $R^{2b}$ group, independently can be hydrogen or a hydrocarbyl group; alternatively, hydrogen; or alternatively, a hydrocarbyl group. In an embodiment, the $R^{2a}$ and $R^{2b}$ organyl groups, of the $N^2$-phosphinyl guanidine chromium compound complexes which have an $R^{2a}$ and/or $R^{2b}$ organyl group, independently can be a $C_1$ to $C_{20}$, a $C_1$ to $C_{15}$, a $C_1$ to $C_{10}$, or a $C_1$ to $C_5$ organyl group. In some embodiments, the $R^{2a}$ and/or $R^{2b}$ organyl groups consisting of inert functional groups, of the $N^2$-phosphinyl guanidine chromium compound complexes which have an $R^{2a}$ and/or $R^{2b}$ organyl consisting of inert functional groups, independently can be a $C_1$ to $C_{20}$, a $C_1$ to $C_{15}$, a $C_1$ to $C_{10}$, or a $C_1$ to $C_5$ organyl group consisting essentially of inert functional groups. In other embodiments, the $R^{2a}$ and/or $R^{2b}$ hydrocarbyl groups, of the $N^2$-phosphinyl guanidine chromium compound complexes which have an $R^{2a}$ and/or $R^{2b}$ hydrocarbyl group, independently can be a $C_1$ to $C_{20}$, a $C_1$ to $C_{15}$, a $C_1$ to $C_{10}$, or a $C_1$ to $C_5$ hydrocarbyl group.

In an embodiment, $R^{2a}$ and $R^{2b}$, of the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group. In some embodiments, $R^{2a}$ and $R^{2b}$, of the $N^2$-phosphinyl guanidine chromium compound complexes which have an $R^{2a}$ and/or $R^{2b}$ organyl group, independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^{2a}$ and $R^{2b}$, of the $N^2$-phosphinyl guanidine chromium compound complexes which have an $R^{2a}$ and/or $R^{2b}$ organyl group, independently can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^{2a}$ and/or $R^{2b}$ independently can be $C_1$ to $C_{20}$, a $C_1$ to $C_{10}$, or a $C_1$ to $C_5$ alkyl group. In any aspect or embodiment disclosed herein, the cycloalkyl group which can be utilized as $R^{2a}$ and/or $R^{2b}$ independently can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{2a}$ and/or $R^{2b}$ independently can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{2a}$ and/or $R^{2b}$ independently can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{2a}$ and/or $R^{2b}$ independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidine chromium compound complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine chromium compound complexes can be joined to form a group, $L^{23}$, wherein $L^{23}$, the $N^2$ nitrogen atom, and the $N^3$ nitrogen atom can form a ring or a ring system. In an embodiment, $L^{12}$ and/or $L^{23}$, of the $N^2$-phosphinyl guanidine chromium compound complexes which have an $L^{12}$ group and/or an $L^{23}$ group, independently can be an organylene group; alternatively, an organylene group consisting of inert functional groups; or alternatively, a hydrocarbylene group. The organylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group. The organylene group consisting of inert functional groups which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group consisting of inert functional groups. The hydrocarbylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ hydrocarbylene group.

In an embodiment, $L^{12}$ and/or $L^{23}$ can have any structure provided in Table 1. In some embodiments, $L^{12}$ and/or $L^{23}$ can have Structure 1L, Structure 2L, Structure 3L, Structure 4L or Structure 5L. In some embodiments, $L^{12}$ and/or $L^{23}$ can have Structure 2L or Structure 3L; alternatively, Structure 4L or Structure 5L. In other embodiments, $L^{12}$ and/or $L^{23}$ can have Structure 1L; alternatively, Structure 2L; alternatively, Structure 3L; alternatively, Structure 4L; or alternatively, Structure 5L. In some embodiments, $L^{12}$ and/or $L^{23}$ can have Structure 6L. It should be noted that when $L^{12}$ has Structure 6L the corresponding $R^{2b}$ is null because of the double bond link (depicted as real but can be delocalized through aromatic resonance) with the $N^3$ nitrogen atom of the $N^2$-phosphinyl guanidine metal complex.

TABLE 1

Structures for Linking Groups $L^{12}$ and/or $L^{23}$.

| | |
|---|---|
| —(CR$^{L1}$R$^{L2}$)$_m$— | Structure 1L |
| —CR$^{L3}$R$^{L4}$—CR$^{L5}$R$^{L6}$— | Structure 2L |
| —CR$^{L3}$R$^{L4}$—CR$^{L7}$R$^{L8}$—CR$^{L5}$R$^{L6}$— | Structure 3L |
| —CR$^{11L}$═CR$^{12L}$— | Structure 4L |
| 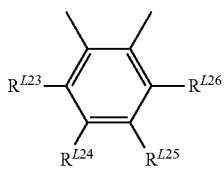 | Structure 5L |
| ═CR$^{27}$—CR$^{28}$═CR$^{29}$— | Structure 6L |

Within the structures of Table 1, the undesignated valences represent the points at which $L^{12}$ and/or $L^{23}$, when present, attach to the respective nitrogen atoms of the $N^2$-phosphinyl guanidine chromium compound complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, and/or Structure 5L. In an embodiment, $L^{12}$ and/or $L^{23}$ can be an eth-1,2-ylene group (—CH$_2$CH$_2$—), an ethen-1,2-ylene group (—CH═CH—), a prop-1,3-ylene group (—CH$_2$CH$_2$CH$_2$—), a 1-methylethen-1,2-ylene group (—C(CH$_3$)═CH—), a but-1,3-ylene group (—CH$_2$CH$_2$CH(CH$_3$)—), a 3-methylbut-1,3-ylene group (—CH$_2$CH$_2$C(CH$_3$)$_2$—), or a phen-1,2-ylene group. In some non-limiting embodiments, $L^{12}$ and/or $L^{23}$ be an eth-1,2-ylene group (—CH$_2$CH$_2$—), a prop-1,3-ylene group (—CH$_2$CH$_2$CH$_2$—), a 1-methylethen-1,2-ylene group (—C(CH$_3$)═CH—), a but-1,3-ylene group (—CH$_2$CH$_2$CH(CH$_3$)—), or a 3-methylbut-1,3-ylene group (—CH$_2$CH$_2$C(CH$_3$)$_2$—); alternatively, an eth-1,2-ylene group (—CH$_2$CH$_2$—), an ethen-1,2-ylene group (—CH═CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH═CH—) or a phen-1,2-ylene group. In other embodiments, $L^{12}$ and/or $L^{23}$ can be an eth-1,2-ylene group (—CH$_2$CH$_2$—); alternatively, an ethen-1,2-ylene group (—CH═CH—); alternatively, a prop-1,3-ylene group (—CH$_2$CH$_2$CH$_2$—); alternatively, a 1-methylethen-1,2-ylene group (—C(CH$_3$)═CH—); alternatively, a but-,3-lene group (—CH$_2$CH$_2$CH(CH$_3$)—); alternatively, a 3-methylbut-1,3-ylene group (—CH$_2$CH$_2$C(CH$_3$)$_2$—); or alternatively, a phen-1,2-ylene group. In some embodiments, $L^{12}$ and/or $L^{23}$ can be a —CH═CH—CH═group.

In an embodiment, $L^{12}$ can have a structure that can comprise at least one substituent located on the carbon atom attached to the $N^1$ nitrogen atom of the $N^2$-phosphinyl guanidine chromium compound complex; alternatively, can comprise only one substituent located on the carbon atom attached to the $N^1$ nitrogen atom of the $N^2$-phosphinyl guanidine chromium compound complex; or alternatively, can comprise two substituents located on the carbon atom attached to the $N^1$ nitrogen atom of the $N^2$-phosphinyl guanidine chromium compound complex. In another embodiment, $L^{12}$ can have a structure that can consist of one substituent located on the carbon atom attached to the $N^1$ nitrogen atom of the $N^2$-phosphinyl guanidine chromium compound complex; or alternatively, can consist of two substituents located on the carbon atom attached to the $N^1$ nitrogen atom of the $N^2$-phosphinyl guanidine chromium compound complex.

In an embodiment, $R^{2a}$ and $R^{2b}$ of the $N^2$-phosphinyl guanidine chromium compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an embodiment, $L^{22}$ of the $N^2$-phosphinyl guanidine chromium compound complexes having an $L^{22}$ group can be an organylene group; alternatively, an organylene group consisting of inert functional groups; or alternatively, a hydrocarbylene group. The organylene group which can be utilized as $L^{22}$ of the $N^2$-phosphinyl guanidine chromium compound complexes having an $L^{22}$ group can be a $C_3$ to $C_{20}$, a $C_3$ to $C_{15}$ organylene, or a $C_3$ to $C_{10}$ organylene group. The organylene group consisting of inert functional groups which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group consisting of inert functional groups. The hydrocarbylene group which can be utilized as $L^{22}$ of the $N^2$-phosphinyl guanidine chromium compound complexes having an $L^{22}$ group can be a $C_4$ to $C_{20}$, a $C_4$ to $C_{15}$, or a $C_4$ to $C_{10}$ hydrocarbylene group.

In an embodiment, $L^{22}$ can have any structure provided in Table 2. In some embodiments, $L^{22}$ can have Structure 11L, Structure 12L, Structure 13L, Structure 14L, Structure 15L; or Structure 16L. In other embodiments, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

| | |
|---|---|
| —(CR$^{L31}$R$^{L32}$)$_n$- | Structure 11L |
| —CR$^{L41}$R$^{L42}$—CR$^{L45}$R$^{L46}$CR$^{L47}$R$^{L48}$ CR$^{L43}$R$^{L44}$— | Structure 12L |
| —CR$^{L41}$R$^{L42}$—CR$^{L45}$R$^{L46}$—CR$^{L49}$R$^{L50}$—CR$^{L47}$R$^{L48}$—CR$^{L43}$R$^{L44}$— | Structure 13L |
| —CR$^{L41}$R$^{L42}$—C$^{RL45}$R$^{L46}$—O—CR$^{L47}$R$^{L48}$—C$^{RLA3}$R$^{L44}$— | Structure 14L |
| —CR$^{L51}$═CR$^{L53}$—CR$^{L54}$═C$^{RL52}$— | Structure 15L |

Within the structures of Table 2, the undesignated valences represent the points at which $L^{22}$ of the $N^2$-phosphinyl guanidine chromium compound complexes, when present, attach to the $N^3$ nitrogen atom of the $N^2$-phosphinyl guanidine chromium compound complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L4}$, $R^{L2}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be hydrogen or an organyl group; hydrogen or an organyl group consisting essentially of inert functional group; alternatively, hydrogen or a hydrocarbyl group; alternatively, hydrogen; alternatively, an organyl group; alternatively, an organyl group consisting essentially of inert functional group; or alternatively, a hydrocarbyl group. In an embodiment, the organyl group which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ organyl group. In an embodiment, the organyl group consisting essentially of inert functional groups which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ organyl group consisting essentially of inert functional groups. In an embodiment, the hydrocarbyl group which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ hydrocarbyl group. In other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ alkyl group. In yet other embodiments, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the $N^2$-phosphinyl formamidine chromium compound complexes, the $N^2$-phosphinyl amidine chromium compound complexes, and/or the $N^2$-phosphinyl guanidine chromium compound complexes having a non-hydrogen $R^3$ group.

Generally, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an organyl group; alternatively, an organyl group consisting essentially of inert functional groups; or alternatively, a hydrocarbyl group. In an embodiment, the $R^4$ and/or $R^5$ organyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group. In an embodiment, the $R^4$ and/or $R^5$ organyl groups consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an embodiment, the $R^4$ and/or $R^5$ hydrocarbyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$ hydrocarbyl, or a $C_1$ to $C_5$ hydrocarbyl group. In further embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes can be joined to form a ring or a ring system.

In an embodiment, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group, a substituted alkyl group, a cycloalkyl group, a substituted cycloalkyl group, an aryl group, a substituted aryl group, an aralkyl group, or a substituted aralkyl group. In some embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other embodiments, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^4$ and/or $R^5$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^4$ and/or $R^5$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^4$ and/or $R^5$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^4$ and/or $R^5$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^4$ and/or $R^5$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^4$ and/or $R^5$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^4$ and/or $R^5$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^4$ and/or $R^5$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an embodiment, $R^4$ and $R^5$ independently can be a methyl group, an ethyl group, a propyl group, a butyl group, a pentyl group, a hexyl group, a heptyl group, or an octyl group. In some embodiments, $R^4$ and $R^5$ independently can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some embodiments, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^4$ and/or $R^5$ independently.

In an embodiment, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an embodiment, the substituted cycloalkyl group, which can be utilized for $R^4$ and $R^5$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an embodiment where the substituted cycloalkyl group (general or specific) has more the one substituent, the substituents can be the same or different; alternatively, the same; or alternatively, different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general or specific), and substituent hydrocarboxy groups (general or specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting embodiments, $R^4$ and $R^5$ independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or 2,5-dialkylcyclopentyl group. Alkyl substituent groups (general or specific) are independently described herein and these alkyl substituent groups can be utilized, without limitation, to further described an alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting embodiments, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting embodiments, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an embodiment, $R^4$ and $R^5$ independently can be a phenyl group, a substituted phenyl group; alternatively, a phenyl group; or alternatively, a substituted phenyl group. In an embodiment, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an embodiment, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general or specific), and substituent hydrocarboxy groups (general or specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting embodiment, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting embodiments, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting embodiment, $R^4$ and/or $R^5$ can be a phenyl group, a 2-alkoxyphenyl group, or a 4-alkoxyphenyl group. In some non-limiting embodiments, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting embodiments, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some embodiments, $R^4$ and $R^5$ independently can be a phenyl group, a 2-fluorophenyl group, a 4-fluorophenyl group, or a 2,6-difluorophenyl group.

In an embodiment, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

Generally, the chromium compound of the $N^2$-phosphinyl formamidine chromium compound complexes, the $N^2$-phosphinyl amidine chromium compound complexes, and/or the $N^2$-phosphinyl guanidine chromium compound complexes described herein has the formula $CrX_p$ where X represents a monoanionic ligand, and p represent the number of monoanionic ligands (and the oxidation state of the chromium in the chromium compound). The monoanionic ligand (X), and p are independent elements of the chromium compound and are independently described herein. The independent descriptions of the monoanionic ligand (X) and p can be utilized without limitation, and in any combination, to further describe the chromium compound of the $N^2$-phosphinyl formamidine chromium compound complexes, the $N^2$-phosphinyl amidine chromium compound complexes, and/or the $N^2$-phosphinyl guanidine chromium compound complexes.

Generally, the chromium atom of the chromium compound ($CrX_p$) can have any positive oxidation state available to a chromium atom. In an embodiment, the chromium atom can have an oxidation state of from +2 to +6; alternatively, from +2 to +4; or alternatively, from +2 to +3. In some embodiments, the chromium atom of the chromium compound (CrX$_p$) can have an oxidation state of +1; alternatively, +2; alternatively, +3; or alternatively, +4.

The monoanion, X, of the chromium compound can be any monoanion. In an embodiment, the monoanion, X, can be a halide, a carboxylate, a β-diketonate, a hydrocarboxide, a nitrate, or a chlorate. In some embodiments, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other embodiments, the monoanion, X, can be a halide, a carboxylate, a β-diketonate, or an alkoxide; or alternatively, a halide or a β-diketonate. In other embodiments, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an embodiment, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion, X, of the chromium compound independently can be fluorine, chlorine, bromine, or iodine; or alternatively, chlorine, bromine, or iodine. In an embodiment, each halide monoanion, X, of the chromium compound can be chlorine; alternatively, bromine; or alternatively, iodine.

Generally, each carboxylate monoanion of the chromium compound independently can be a $C_1$ to $C_{20}$ carboxylate; or alternatively, a $C_1$ to $C_{10}$ carboxylate. In an embodiment, each carboxylate monoanion of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some embodiments, each carboxylate monoanion of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some embodiments, the carboxylate monoanion of the chromium compound can be triflate (trifluoroacetate).

Generally, each β-diketonate monoanion of the chromium compound independently can be any $C_1$ to $C_{20}$ a β-diketonate; or alternatively, any $C_1$ to $C_{10}$ β-diketonate. In an embodiment, each β-diketonate monoanion of the chromium compound independently can be acetylacetonate (i.e., 2,4-pentanedionate), hexafluoroacetylacetone (i.e., 1,1,1,5,5,5-hexafluoro-2,4-pentanedionate), or benzoylacetonate); alternatively, acetylacetonate; alternatively, hexafluoroacetylacetone; or alternatively, benzoylacetonate.

Generally, each hydrocarboxide monoanion of the chromium compound independently can be any $C_1$ to $C_{20}$ hydrocarboxide; or alternatively, any $C_1$ to $C_{10}$ hydrocarboxide. In an embodiment, each hydrocarboxide monoanion of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an embodiment, each alkoxide monoanion of the chromium compound independently can be methoxide, ethoxide, a propoxide, or a butoxide. In some embodiments, each alkoxide monoanion of the chromium compound independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In a non-limiting embodiment, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(III) halide, a chromium(II) carboxylate, chromium(III) carboxylate, a chromium(II) β-diketonate, or a chromium(III) β-diketonate. In some non-limiting embodiments, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting embodiment, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(II) chloride, chromium(III) chloride, chromium(II) fluoride, chromium(III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (III) benzoylacetonate, or chromium(III) benzoylacetonate. In some non-limiting embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium (III) acetylacetonate, chromium(III) hexafluoracetylacetonate, or chromium(III) benzoylacetonate. In further embodiments, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can be chromium(III) chloride, or chromium(III) acetylacetonate; alternatively, chromium(III) chloride; or alternatively, chromium(III) acetylacetonate.

Generally, the neutral ligand, Q, of any of the $N^2$-phosphinyl formamidine chromium compound complexes, the $N^2$-phosphinyl amidine chromium compound complexes, and/or the $N^2$-phosphinyl guanidine chromium compound complexes described herein, if present, independently can be any neutral ligand that forms an isolatable compound with the $N^2$-phosphinyl formamidine chromium compound complex, the $N^2$-phosphinyl amidine chromium compound complex, and/or the $N^2$-phosphinyl guanidine chromium compound complex. In an aspect, each neutral ligand independently can be a nitrile or an ether; alternatively, a nitrile; or alternatively, an ether. The number of neutral ligands, q, can be any number that forms an isolatable compound with the $N^2$-phosphinyl formamidine chromium compound complexes, the $N^2$-phosphinyl amidine chromium compound complexes, and/or the $N^2$-phosphinyl guanidine chromium compound complexes. In an aspect, the number of neutral ligands of any of the $N^2$-phosphinyl formamidine chromium compound complexes, the $N^2$-phosphinyl amidine chromium compound complexes, and/or the $N^2$-phosphinyl guanidine chromium compound complexes described herein can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an embodiment, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each aliphatic nitrile independently can be acetonitrile, propionitrile, a butyronitrile, benzonitrile, or any combination thereof; alternatively, acetonitrile; alternatively; propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an embodiment, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

In a non-limiting embodiment, the $N^2$-phosphinyl formamidine chromium compound complex can be any one or more of NPFCr I, NPFCr II, NPFCrR III, NPFCr IV, NPFCr V, and NPFCr VI. In a non-limiting embodiment, the $N^2$-phosphinyl amidine chromium compound complex can be any one or more of NPACR I, NPACR II, NPACr III, NPACr IV, NPACr V, NPACr VI, NPACr VII, NPACr VIII, NPACr IX, NPACr X, NPACr XI, and NPACr XII. In a non-limiting embodiment, the $N^2$-phosphinyl guanidine chromium compound complex can be any one or more of GuFCr I, GuCr II, GuCr III, GuCr IV, GuCr V, and GuCr VI. In a non-limiting embodiments, the chromium compound, $CrX_3$, of any of NPFCr I, NPFCr II, NPFCrR III, NPFCr IV, NPFCr V, NPFCr VI, NPACR I, NPACR II, NPACr III, NPACr IV, NPACr V, NPACr VI, NPACr VII, NPACr VIII, NPACr IX, NPACr X, NPACr XI, NPACr XII, GuFCr I, GuCr II, GuCr III, GuCr IV, GuCr V, and GuCr VI can be chromium(III) chloride or chromium(III) acetylacetonate; alternatively, chromium(III) chloride; or alternatively, chromium(III) acetylacetonate.

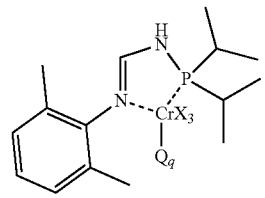

NPFCr I

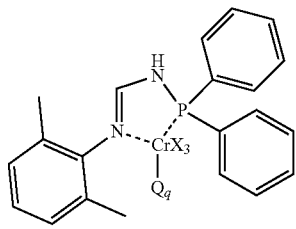

NPFCr II

NPFCr III
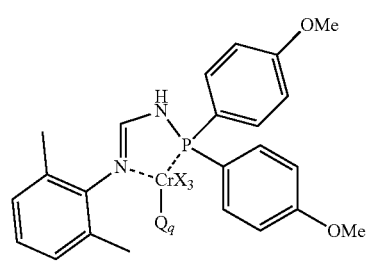
NPFCr IV
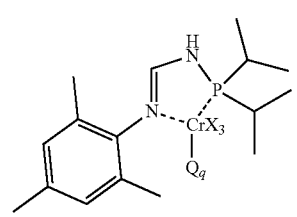
NPFCr V
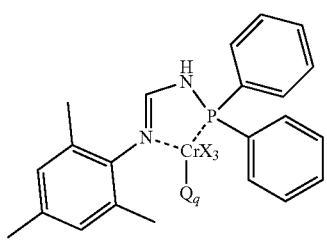
NPFCr VI
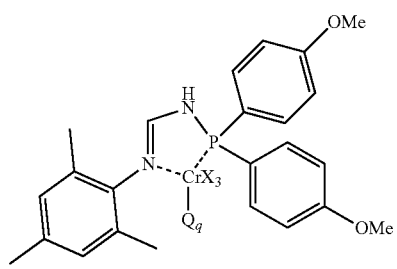
NPACr I
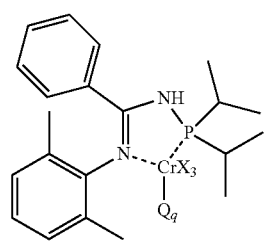
NPACr II
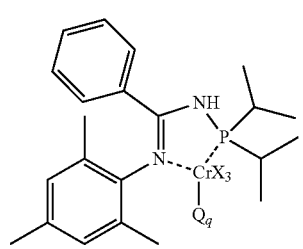
NPACr III
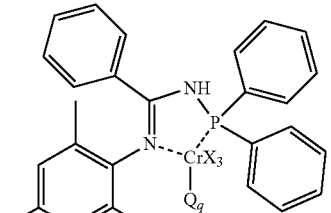
NPACr IV
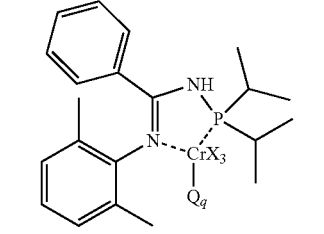
NPACr V
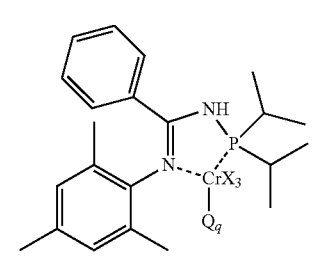
NPACr VI
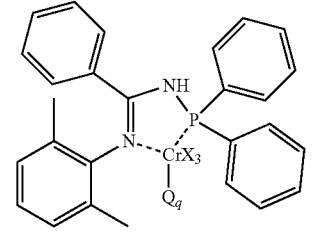
NPACr VII
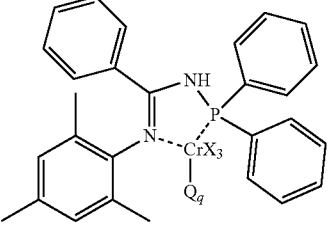
NPACr VIII
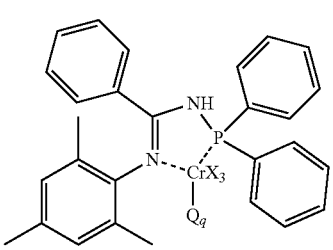

-continued
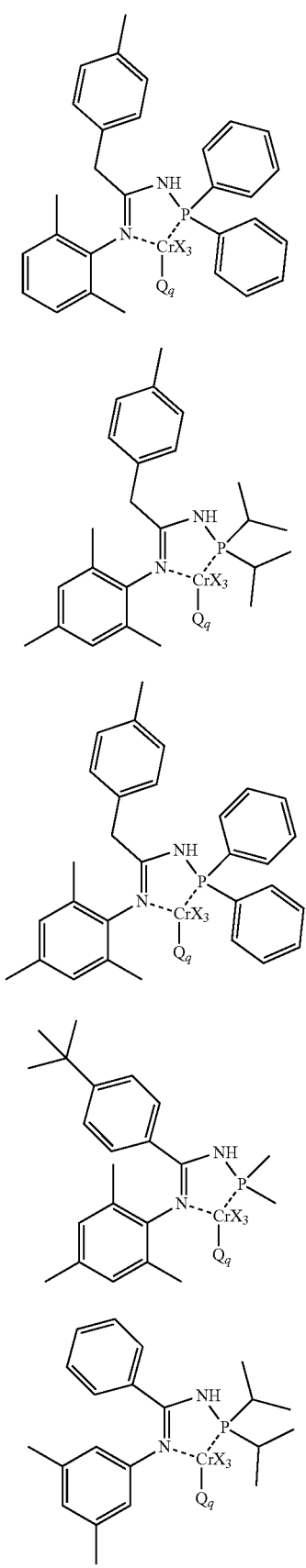
NPACr IX
NPACr X
NPACr XI
NPACr XII
NPACr I
-continued
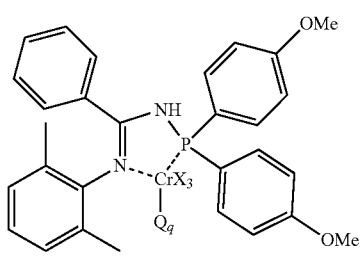
NPACr I
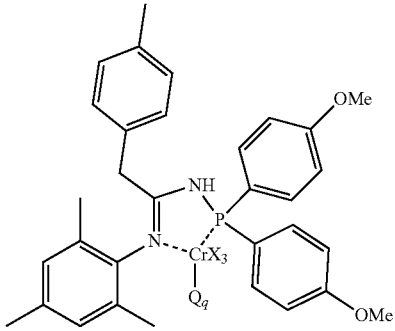
NPACr I
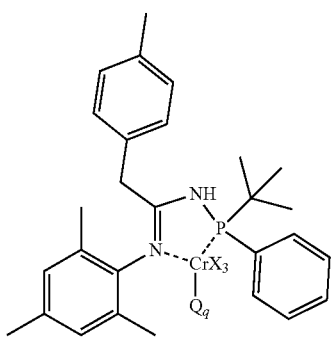
NPACr I
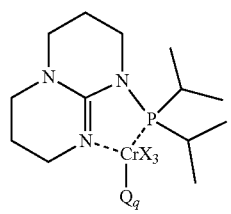
GuCr I
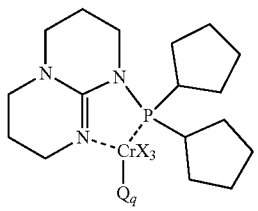
GuCr II
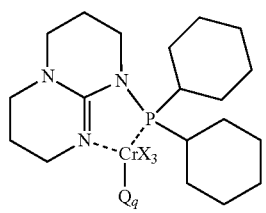
GuCr III

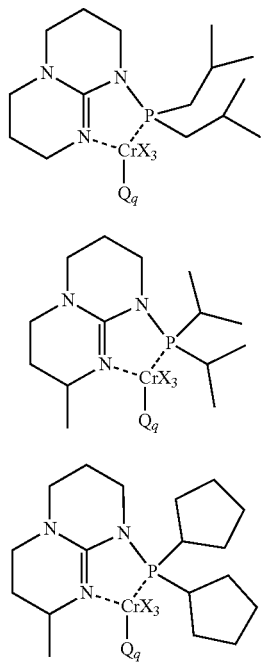

GuCr IV

GuCr V

GuCr VI

Generally, the aluminoxane utilized in the catalyst systems which are utilized in the processes, systems, and/or reaction systems can be any aluminoxane which can, in conjunction with the $N^2$-phosphinyl formamidine chromium compound complex, the $N^2$-phosphinyl amidine chromium compound complex, and/or the $N^2$-phosphinyl guanidine chromium compound complex, catalyze the formation of an ethylene oligomer product. In a non-limiting embodiment, the aluminoxane can have a repeating unit characterized by the Formula I:

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each alkyl group of the aluminoxane independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an embodiment, each alkyl group of the aluminoxane independently can be, comprise, or consist essentially of, a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group or the aluminoxane independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In a non-limiting embodiment, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-pentylaluminoxane, 3-pentyl-aluminoxane, iso-pentyl-aluminoxane, neopentylaluminoxane, or mixtures thereof. In some non-limiting embodiments, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting embodiments, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

The scrub agent which can be utilized in aspects and embodiments of any of the processes, systems, and/or reaction systems described herein can be any compound(s) which can remove water, oxygen, and/or other species detrimental to the ability of the catalyst system to oligomerize ethylene. In some embodiments, the scrub agent can be an organoaluminum compound. In an embodiment, the organoaluminum compound can be an alkylaluminum compound. In an embodiment, the alkylaluminum compound can be a trialkylaluminum, an alkylaluminum halide, an alkylaluminum alkoxide, or any combination thereof. In some embodiments, the alkylaluminum compound can be a trialkylaluminum, an alkylaluminum halide, or any combination thereof; alternatively, a trialkylaluminum, an alkylaluminum halide, or any combination thereof; or alternatively, a trialkylaluminum. In other embodiments, the alkylaluminum compound can be a trialkylaluminum; alternatively, an alkylaluminum halide; or alternatively, an alkylaluminum alkoxide. In yet other embodiments, the alkylaluminum compound which can be utilized as the scrub agent can be an aluminoxane (described herein). In a non-limiting embodiment, the trialkylaluminum compound can be, comprise, or consist essentially of, trimethylaluminum, triethylaluminum, tripropylaluminum, tributylaluminum, trihexylaluminum, trioctylaluminum, or mixtures thereof. In some non-limiting embodiments, the trialkylaluminum compound can be, comprise, or consist essentially of, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can be, comprise, or consist essentially of, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum. In a non-limiting embodiment, the alkylaluminum halide can be, comprise, or consist essentially of, diethylaluminum chloride, diethylaluminum bromide, ethylaluminum dichloride, ethylaluminum sesquichloride, or mixtures thereof. In some non-limiting embodiments, the alkylaluminum halide can be, comprise, or consist essentially of, diethylaluminum chloride, ethylaluminum dichloride, ethylaluminum sesquichloride, or mixtures thereof. In other non-limiting embodiments, the alkylaluminum halide can be, comprise, or consist essentially of, diethylaluminum chloride; alternatively, diethylaluminum bromide; alternatively, ethylaluminum dichloride; or alternatively, ethylaluminum sesquichloride. In particular aspects of this invention, the organoaluminum compound can comprise trimethylaluminum (TMA), triethylaluminum (TEA), tri-n-propylaluminum (TNPA), tri-n-butylaluminum (TNBA), tri-isobutylaluminum (TIBA), tri-n-hexylaluminum, tri-n-octylaluminum, diisobutylaluminum hydride, diethylaluminum ethoxide, diethylaluminum chloride, or combinations thereof.

In an embodiment, the alkylaluminum compound which can be utilized as the scrub agent can be an aluminoxane. Aluminoxanes are independently disclosed herein (e.g., as a component of the catalyst system) and any of the general or specific aluminoxanes disclosed herein can be utilized without limitation as the scrub agent utilized in the processes, systems and/or reaction systems disclosed herein.

The herein disclosed scrub agent(s) optionally can be indirectly introduced to the reaction zone 110 from a scrub agent source 170 via feed line 172. The scrub agent feed line 172, when present in system 100, 200, or 300, is defined as having at least one scrub agent. While the scrub agent is shown in FIG. 1, FIG. 2, and FIG. 3 as feeding into organic reaction medium feed line 162, it is contemplated the scrub agent alternatively can feed into any of line 142, line 152, line 191, line 192, and line 193.

Generally, the ethylene oligomer product that can be produced using the processes, systems, and/or reaction system described herein can be formed at conditions (or alternatively, the reaction zone can have any conditions) which can 1) facilitate ethylene oligomer product formation, 2) provide a desired ethylene oligomer product formation rate, 3) provide acceptable catalyst system productivity, 4) provide acceptable oligomer selectivity, and/or 5) provide acceptable polymer formation. In an embodiment, conditions under which the ethylene oligomer product can be formed (or alternatively, the reaction zone can have any conditions) can include one or more of catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity. Catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity are independently described herein and these independent descriptions can be used without limitation, and in any combination, to describe the process, system, and/or reaction zone conditions at which the ethylene oligomer product can be formed for any of the processes, systems, and/or reaction systems described herein.

In an embodiment, the ethylene oligomer product can be formed (or the reaction zone can operate) at a minimum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., minimum Al to Cr molar ratio) of 10:1, 50:1, 75:1, or 100:1; alternatively or additionally, at a maximum aluminum of the aluminoxane to chromium of the chromium component (e.g., $N^2$-phosphinyl formamidine chromium compound complex, the $N^2$-phosphinyl amidine chromium compound complex, and/or the $N^2$-phosphinyl guanidine chromium compound complex) molar ratio (i.e., maximum Al to Cr molar ratio) of 5,000:1, 3,000:1, 2,000:1, 1,500:1, or 1,000:1. In an embodiment, the ethylene oligomer product can be formed (or the reaction zone can operate) at an Al to Cr molar ratio ranging from any minimum Al to Cr molar ratio disclosed herein to any maximum Al to Cr molar ratio disclosed herein. In a non-limiting embodiment, the Al to Cr molar ratio can range from 10:1 to 5,000:1, from 50:1 to 3,000:1, from 50:1 to 3,000:1, from 75:1 to 2,000:1, from 100:1 to 2,000:1, of from 100:1 to 1,000:1. Other Al to Cr molar ratio ranges that can be utilized are readily apparent to those skilled in the art with the aid of this disclosure.

In an embodiment, the ethylene oligomer product can be formed (or the reaction zone can operate) at a minimum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., minimum chromium concentration) of $1 \times 10^{-6}$ Cr equivalents/liter, $1 \times 10^{-5}$ Cr equivalents/liter, or $5 \times 10^{-4}$ Cr equivalents/liter; alternatively or additionally, at a maximum reaction zone chromium concentration of the chromium component (e.g., $N^2$-phosphinyl formamidine chromium compound complex, the $N^2$-phosphinyl amidine chromium compound complex, and/or the $N^2$-phosphinyl guanidine chromium compound complex) concentration (i.e., maximum chromium concentration) of 1 Cr equivalents/liter, $5 \times 10^{-1}$ Cr equivalents/liter, or $1 \times 10^{-1}$ Cr equivalents/liter. In an embodiment, the ethylene oligomer product can be formed (or the reaction zone can operate) at a reaction zone chromium concentration ranging from any minimum chromium concentration disclosed herein to any maximum chromium concentration disclosed herein. In a non-limiting embodiment, the reaction zone chromium concentration can range from $1 \times 10^{-6}$ Cr equivalents/liter to 1 Cr equivalents/liter, from $1 \times 10^{-5}$ Cr equivalents/liter to $5 \times 10^{-1}$ Cr equivalents/liter, from $5 \times 10^{-4}$ Cr equivalents/liter to $1 \times 10^{-1}$ Cr equivalents/liter. Other chromium concentration ranges that can be utilized are readily apparent to those skilled in the art with the aid of this disclosure.

In an embodiment, the ethylene oligomer product can be formed (or the reaction zone can operate) at a minimum pressure of 5 psi (34.5 kPa), 50 psi (345 kPa); 100 psi (689 kPa), 150 psi (1.03 MPa), 250 psi (1.72 MPa), 500 psi (3.5 MPa), or 600 psi (4.1 MPa); alternatively or additionally at a maximum pressure of 2,500 psi (17.2 MPa), 2,000 psi (13.8 MPa), 1,500 psi (10.3 MPa), 1400 psi (9.65 MPa), 1250 psi (8.62 MPa), or 1000 psi (6.89 MPa). In an embodiment, the ethylene oligomer product can be formed (or the reaction zone can operate) at a pressure ranging from any minimum pressure disclosed herein to any maximum pressure disclosed herein. In some non-limiting embodiments, the ethylene oligomer product can be formed (or the reaction zone can operate) at a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 250 psi (1.72 MPa) to 1000 psig (6.89 MPa), or from 600 psi (4.1 MPa) to 1400 psi (9.65 MPa). Other pressure ranges that can be utilized are readily apparent to those skilled in the art with the aid of this disclosure.

In an embodiment, the ethylene oligomer product can be formed (or the reaction zone can operate) at a minimum ethylene partial pressure of 5 psi (34.5 kPa), 50 psi (345 kPa); 100 psi (689 kPa), 150 psi (1.03 MPa), 250 psi (1.72 MPa), or 500 psi (3.5 MPa); alternatively or additionally, at a maximum ethylene partial pressure of 2,500 psi (17.2 MPa), 2,000 psi (13.8 MPa), 1,500 psi (10.3 MPa), 1250 psi (8.62 MPa), or 1000 psi (6.89 MPa). In an embodiment, the ethylene oligomer product can be formed (or the reaction zone can operate) at an ethylene partial pressure ranging from any minimum ethylene partial pressure disclosed herein to any maximum ethylene partial pressure disclosed herein. In some non-limiting embodiments, the ethylene oligomer product can be formed (or the reaction zone can operate) at an ethylene partial pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 150 psi (1.03 MPa) to 1250 psi (8.62 MPa), or from 250 psi (1.72 MPa) to 1000 psi (6.89 MPa). Other ethylene partial pressure ranges are readily apparent to those skilled in the art with the aid of this disclosure.

In an embodiment, the ethylene oligomer product can be formed (or the reaction zone can operate) at a minimum ethylene concentration of 4 mass %, 10 mass %, 25 mass %, 35 mass %, or 40 mass % based upon the total mass in the reaction zone; alternatively or additionally, at a maximum ethylene concentration of 70 mass %, 65 mass %, 60 mass %, 55 mass %, 50 mass %, 48 mass % based upon the total mass in the reaction zone. In an embodiment, the ethylene oligomer product can be formed (or the reaction zone can operate) at an ethylene concentration ranging from any minimum ethylene concentration disclosed herein to any maximum ethylene concentration disclosed herein. In some non-limiting embodiments, the ethylene oligomer product can be formed (or the reaction zone can operate) at an ethylene concentration from 4 mass % to 70 mass %, from 4 mass % to 60 mass %, from 10 mass % to 60 mass %, from 25 mass % to 55 mass %, 35 mass % to 50 mass %, or 40 mass % to 48 mass % based upon the total mass in the reaction zone. Other ethylene concentration ranges that can be utilized are readily apparent to those skilled in the art with the aid of this disclosure.

In an embodiment, the ethylene oligomer product can be formed (or the reaction zone can operate) at a minimum ethylene:chromium mass ratio of 50,000:1, 150,000:1, 250,000:1, or 400,000:1; alternatively or additionally, at a maximum ethylene:chromium mass ratio of 5,000,000:1, 2,500,000:1, 1,500,000:1, or 1,000,000:1. In an embodiment, the ethylene oligomer product can be formed (or the reaction zone can operate) at an ethylene:chromium mass ratio ranging from any minimum ethylene:chromium mass ratio disclosed herein to any maximum ethylene:chromium mass ratio disclosed herein. In some non-limiting embodiments, the ethylene oligomer product can be formed (or the reaction zone can operate) at an ethylene:chromium mass ratio from 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure.

In an embodiment wherein hydrogen is utilized, the oligomer product can be formed (or the reaction zone can operate) at a minimum hydrogen partial pressure of 1 psi (6.9 kPa), 2 psi (14 kPa); 5 psi (34 kPa), 10 psi (69 kPa), or 15 psi (103 kPa); alternatively or additionally at a maximum hydrogen partial pressure of 200 psi (1.4 MPa), 150 psi (1.03 MPa), 100 psi (689 kPa), 75 psig (517 kPa), or 50 psi (345 kPa). In an embodiment, the oligomer product can be formed (or the reaction zone can operate) at a hydrogen partial pressure ranging from any minimum hydrogen partial pressure disclosed herein to any maximum hydrogen partial pressure disclosed herein. In some non-limiting embodiments wherein hydrogen is utilized, the oligomer product can be formed (or the reaction zone can operate) at a hydrogen partial pressure from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

In an embodiment wherein hydrogen is utilized, the ethylene oligomer product can be formed (or the reaction zone can operate) at a minimum hydrogen to ethylene mass ratio of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); alternatively or additionally, at a maximum hydrogen to ethylene mass ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). In an embodiment, the ethylene oligomer product can be formed (or the reaction zone can operate) at a hydrogen to ethylene mass ratio ranging from any minimum hydrogen to ethylene mass ratio disclosed herein to any maximum hydrogen to ethylene mass ratio disclosed herein. In some non-limiting embodiments, the ethylene oligomer product can be formed (or the reaction zone can operate) at a hydrogen to ethylene mass ratio from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

In an embodiment, the ethylene oligomer product can be formed (or the reaction zone can operate) at a minimum hydrogen:chromium mass ratio of 1:1, 50:1, 100:1, or 200:1; alternatively or additionally, at a maximum hydrogen:chromium mass ratio of 100,000:1, 50,000:1, 10,000:1, or 3,000:1. In an embodiment, the ethylene oligomer product can be formed (or the reaction zone can operate) at a hydrogen:chromium mass ratio ranging from any minimum hydrogen:chromium mass ratio disclosed herein to any maximum hydrogen:chromium mass ratio disclosed herein. In some non-limiting embodiments, the ethylene oligomer product can be formed (or the reaction zone can operate) at a hydrogen:chromium mass ratio from 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure.

In an embodiment, the ethylene oligomer product can be formed (or the reaction zone can operate) at a minimum temperature of 0° C., 25° C., 40° C., or 50° C.; alternatively or additionally, at a maximum temperature of 200° C., 150° C., 100° C., or 90° C. In an embodiment, the ethylene oligomer product can be formed (or the reaction zone can operate) at a temperature ranging from any minimum temperature disclosed herein to any maximum temperature disclosed herein. In some non-limiting embodiments, the ethylene oligomer product can be formed (or the reaction zone can operate) at a temperature from 0° C. to 200° C., from 25° C. to 150° C., from 40° C. to 100° C., from 50° C. to 100° C., or from 50° C. to 90° C. Other temperature ranges that can be utilized are readily apparent to those skilled in the art with the aid of this disclosure.

The reaction time (or residence time), for example, in the reaction zone can comprise any time that can produce the desired quantity of ethylene oligomer product; alternatively, any reaction time (or residence time) that can provide a desired catalyst system productivity; alternatively, any reaction time (or residence time) that can provide a desired ethylene conversion. Relating to forming the ethylene oligomer product, the ethylene oligomer product can be formed over a period of time (or an average time) that can produce the desired quantity of olefin product or polymer product, provide a desired catalyst system productivity, and/or provide a desired conversion of monomer. In some embodiments, the time can range from 1 minute to 5 hours; alternatively, ranges from 5 minutes to 2.5 hours; alternatively, ranges from 10 minutes to 2 hours; or alternatively, ranges from 15 minutes to 1.5 hours. In some embodiments (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

In an embodiment, the processes, systems, and/or reaction systems described herein can have an ethylene conversion of at least 30%, 35%, 40%, or 45%.

In an embodiment, the process and/or reaction systems described herein can have a catalyst system productivity of greater than 10,000, 50,000, 100,000, 150,000, 200,000, 300,000, or 400,000 grams ($C_6+C_8$) per gram of chromium. In some embodiments (but not all embodiments), the processes, systems, and/or reaction systems described herein can have a productivity higher than a productivity in an otherwise similar process which does not contact ethylene with the at least a portion of the organic reaction medium prior to contact of ethylene with the catalyst system; alternatively, does not introduce or feed the feedstock mixture into the reaction zone separately from the catalyst system; or alternatively, productivity greater than a productivity in an otherwise similar process which does not: i) contact ethylene with the at least a portion of the organic reaction medium prior to contact of ethylene with the catalyst system, and/or ii) introduce or feed the feedstock mixture into the reaction zone separately from the catalyst system. In an embodiment (but not all embodiments), the productivity can be increased by at least 5%, 7.5%, 10%, or 12.5%.

In some aspects and/or embodiments (but not necessarily all aspects and/or embodiments), the processes, systems, and/or reaction systems described herein can produce less polymer per gram of ethylene oligomer product than an otherwise similar process which i) does not contact ethylene with the at least a portion of the organic reaction medium prior to contact of ethylene with the catalyst system, ii) does not introduce or feed the feedstock mixture into the reaction zone separately from the catalyst system, iii) the $C_{3+}$ olefin is not introduced to the reaction zone, or iv) ethylene is introduced into the reaction zone which does not contain $C_{3+}$ olefin. In an embodiment (but not all embodiments), the mass of polymer per mass of oligomer in the reaction zone can decrease by 10%, 25%, 40%, 50%, 60%, 70%, or 80%.

Depending upon the catalyst system utilized, the processes, systems, and/or reaction systems described herein can be an ethylene oligomerization process, system, and/or reaction system, an ethylene trimerization process, system, or reaction system, an ethylene tetramerization process, system, or reaction system or an ethylene trimerization and tetramerization process system, or reaction system; alternatively, an ethylene oligomerization process system, or reaction system; alternatively, an ethylene trimerization process, system, or reaction system; alternatively, an ethylene tetramerization process, system, or reaction system; or alternatively an ethylene trimerization and tetramerization process, system, or reaction system. In an ethylene trimerization embodiment, the ethylene oligomer product can comprise at least 70 wt. % hexenes, at least 75 wt. % hexenes, at least 80 wt. % hexenes, at least 85 wt. % hexenes, or at least 90 wt. % hexene based upon the weight of the ethylene oligomer product. In some ethylene trimerization embodiments, the ethylene oligomer product can comprise from 70 wt. % to 99.8 wt. % hexenes, from 75 wt. % to 99.7 wt. % hexenes, or from 80 wt. % to 99.6 wt. % hexenes based upon the weight of the ethylene oligomer product. In an ethylene tetramerization embodiment, the ethylene oligomer product can comprise at least 70 wt. % octene, at least 75 wt. % octene, at least 80 wt. % octenes, at least 85 wt. % octenes, or at least 90 wt. % octenes based upon the weight of the ethylene oligomer product. In some ethylene tetramerization embodiments, the ethylene oligomer product can comprise from 70 wt. % to 99.8 wt. % octenes, from 75 wt. % to 99.7 wt. % octenes, or from 80 wt. % to 99.6 wt. % octenes based upon the weight of the ethylene oligomer product. In an ethylene trimerization and tetramerization embodiment, the ethylene oligomer product can comprise at least 70 wt. % hexenes and octenes, at least 75 wt. % hexenes and octenes, at least 80 wt. % hexenes and octenes, at least 85 wt. % hexene and octene, or at least 90 wt. % hexenes and octenes based upon the weight of the ethylene oligomer product. In some ethylene trimerization and tetramerization embodiments, the ethylene oligomer product can comprise from 70 wt. % to 99.8 wt. % hexenes and octenes, from 75 wt. % to 99.7 wt. % hexenes and octenes, or from 80 wt. % to 99.6 wt. % hexenes and octenes based upon the weight of the ethylene oligomer product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. %

1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

The processes, systems, and/or reaction systems described herein can provide various advantages. Without being limited to theory, it is believed that the presence of a $C_{3+}$ olefin during the initial startup of a selective oligomerization process or reaction system can decrease the mass of polymer during the startup of oligomerization processes, systems, and/or reaction system. This reduction in the mass of polymer during startup of oligomerization processes, systems, and/or reaction systems described herein can lead to improved process, system, and/or reaction system operability and/or productivity. Another source of polymer formation can result when high concentrations of ethylene contact the catalyst system. The processes, systems, and/or reaction systems (e.g., reaction systems 100, 200, and/or 300) described herein can reduce the amount of polymer formed by the use of a $C_{3+}$ olefin during the initial stages of ethylene oligomerization and/or contacting ethylene with at least a portion of the organic reaction medium prior to ethylene contacting the catalyst system. For example, as is seen in the examples provided herein, the mass of polymer (e.g., polyethylene in contrast to desired oligomers of ethylene) per mass of oligomer in the reaction zone (e.g., reaction zone 110 in reactions systems 100, 200, and 300) can be less than a mass of polymer per mass of oligomer in the reaction zone of otherwise similar processes, systems, and/or reaction systems where the $C_{3+}$ olefin is not introduced to the reaction zone 110 or ethylene is introduced into the reaction zone 110 which does not contain $C_{3+}$ olefin.

Additionally, the mass of polymer (e.g., polyethylene in contrast to desired oligomers of ethylene) per mass of oligomer in the reaction zone (e.g., reaction zone 110) for the processes, systems, and/or reaction system (e.g., reaction systems 200 and 300) can be less than a mass of polymer per mass of oligomer in the reaction zone of otherwise similar systems or process which do not include contacting ethylene with at least a portion of the organic reaction medium prior to contact of ethylene with the catalyst systems disclosed herein. The mass of polymer per mass of oligomer in the reaction zone (e.g., reaction zone 110) for the processes, systems, and/or reaction system (e.g., reaction systems 200 and 300) can be less than a mass of polymer per mass of ethylene oligomer in the reaction zone of an otherwise similar system or process which does not introduce or feed the feedstock mixture to the reaction zone separately from the catalyst systems disclosed herein.

Additionally, the productivity of the processes, system, and/or reaction systems (e.g., reaction systems 100, 200, and 300) can be higher than otherwise similar processes, systems, and/or reaction system where the $C_{3+}$ olefin is not introduced to the reaction zone 110 and/or ethylene is introduced into the reaction zone 110 which does not contain $C_{3+}$ olefin. Productivity is defined as the mass of liquid ethylene oligomer product (or alternatively, $C_6$ product, $C_8$ product, or ($C_6+C_8$) product) formed per mass of chromium or aluminum.

Additionally, the productivity of the processes, systems, and/or reaction systems (e.g., reaction systems 200 and 300) can be greater than other similar systems and processes, systems, and/or reaction systems which do not contact ethylene with at least a portion of the organic reaction medium prior to contact of ethylene with the chromium component of the catalyst systems disclosed herein. The productivity of the processes, systems, and/or reaction system (e.g., reaction systems 200 and 300) can be greater than other similar processes, systems, and/or reaction systems which do not introduce or feed the feedstock mixture to the reaction zone separately from the catalyst systems disclosed herein.

The disclosed processes, systems and/or reaction system can provide improved commercial applicability for the use of catalysts in ethylene oligomerization. While not wishing to be bound by theory, it is believed that longer operating times are possible because the disclosed systems and processes can reduce polymerization during oligomerization, thus reducing the levels of problematic fouling and plugging which can occur in oligomerization reactor components.

Further, the disclosed systems and processes provide improved ethylene utilization as indicated by improved ethylene conversion and higher $C_6$ purity in the ethylene oligomer product.

EXAMPLES

The subject matter having been generally described, the following examples are given as particular aspects of the disclosure and to demonstrate the practice and advantages thereof. It is understood that the examples are given by way of illustration and are not intended to limit the specification of the claims to follow in any manner.

The catalyst system was prepared in a dry box by mixing 25-30 mg of Chromium Component I into 6 mL of ethylbenzene and stirred until the chromium component was fully dissolved. The aluminoxane MMAO-3A (7 wt. % Al) was then added to the chromium component/ethylbenzene mixture in an amount to achieve an Al:Cr molar ratio of 800:1 and mixed for 5 to 10 minutes. The chromium component/ethylbenzene/aluminoxane mixture was then diluted with methyl cyclohexane (MCH) to provide a catalyst system mixture having a concentration of 0.025 mg Cr/mL.

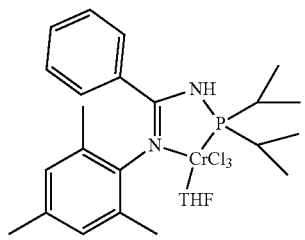

Chromium Component I

Table 3 provides a summary of the operating parameters for the selective oligomerization of ethylene presented in Examples 1 to 3.

TABLE 3

Operating Parameters

|  | Example 1 | Example 2 | Example 3 |
|---|---|---|---|
| Temperature (° C.) | 70 | 70 | 70 |
| Pressure (psig; MPag) | 900; 6.21 | 900; 6.21 | 900; 6.21 |
| Organic Reaction Medium | Cyclohexane | Cyclohexane | Cyclohexane |
| Organic reaction Medium Feed Rate (g/h) | 400 | 400 | 400 |
| Hydrogen Feed Rate (sccm) | 24 | 24 | 24 |
| Catalyst System Mixture Feed Rate (mL/h) | 12.5 | 12.5 | 12.5 |

In Table 3 and the other tables included herein, use of "g" refers to grams, "h" refers to hours, "mL" refers to milliliters, "min" refers to minutes, "sccm" refers to standard cubic centimeters per minute, "MPag" refers to megapascals gauge, and "psig" refers to pounds per square inch gauge.

The organic reaction medium (cyclohexane) was treated with mole sieves and copper oxide prior to being used for the ethylene oligomerization.

Example 1 (Comparative)

In Example 1 (comparative), the oligomerization of ethylene was performed without using $C_{3+}$ olefin in the reaction zone during reaction zone startup.

A 300 cc autoclave reactor having the feed line configurations shown in FIG. 2 was used as the reaction zone 110 and reaction system for Example 1. Although the system 200 of FIG. 2 was used for Example 1, the lines 146 and 147a-f, which can provide $C_{3+}$ olefin, were not used in Example 1. That is, a $C_{3+}$ olefin was not utilized in Example 1 for comparison purposes to Example 3. As can be seen, the ethylene feed line 142 joins with the organic reaction medium feed line 162 to yield the feedstock mixture feed line 191, which flows through a mixing device 190, which for Example 1, was a static mixer. Dispersed feedstock mixture leaves the mixing device 190 in line 192, which feeds to the reaction zone 110 via second reaction zone inlet 113. The catalyst system feed line 152 feeds to the reaction zone 110 via first reaction zone inlet 111 without any combination with other streams or dilution. For Example 1, the control valve 130 shown in FIG. 2 was a pair of control valves placed in parallel flow, with the second valve of the two control valves being used only upon plugging of the first control valve, if plugging were to occur. That is, the second of the two control valves was used as a backup to the first of the two control valves so as to keep the experiment running, if needed.

Prior to startup, the reactor was pressure tested with nitrogen and purged to ensure that no residual air or moisture was present in the reactor.

For startup, the organic reaction medium (anhydrous cyclohexane) was pumped using pump 180 from the organic reaction medium source 160 to the reaction zone 110 via line 162, line 191, mixing device 190, and line 192. Once flow of the organic reaction medium was established, the pressure of the reaction zone 110 was adjusted to 900 psig (6.21 MPag), and the temperature of the autoclave was increased to 70° C. After the pressure and temperature were reached, hydrogen flow at 24 sccm was initiated via line 144, line 142, line 191, mixing device 190, and line 192, and 15.7 mL of the catalyst system was charged to the reactor via line 152. Catalyst system flow rate was then set to 15.7 mL/h. Thirty minutes after setting the catalyst system flow rate, ethylene was fed at 50 g/h to the reaction zone 110 via line 142, line 191, mixing device 190, and line 192. Every 15 minutes thereafter, the ethylene flow rate was increased by 50 g/h until 250 g/h was reached. The first of the two control valves plugged at 187 minutes. High catalyst productivity was observed at this point. The run was terminated at 307 minutes due to plugging/fouling of the autoclave reactor and additional plugging of the second of the two control valves. Samples of the reaction zone effluent were taken every 30 minutes via a sample port located on the reaction zone effluent line 118. After run completion, the reactor was disassembled, the polymer recovered and weighed. The amount of polymer recovered from the reactor is reported in Table 5 along with additional ethylene oligomerization run data.

Example 2 (Comparative)

In Example 2 (comparative), the oligomerization of ethylene was performed without using $C_{3+}$ olefin in the reaction zone startup.

A 300 cc autoclave reactor having the feed line configurations shown in FIG. 2 was used as the reaction zone 110 and reaction system for Example 2. Although the system 200 of FIG. 2 was used for Example 2, the lines 146 and 147a-f, which can provide $C_{3+}$ olefin, were not used in Example 2. That is, a $C_{3+}$ olefin was not utilized in Example 2 for comparison purposes to Example 3. As can be seen, the ethylene feed line 142 joins with the organic reaction medium feed line 162 to yield the feedstock mixture feed line 191, which flows through a mixing device 190 (which was a static mixer). Dispersed feedstock mixture leaves the mixing device 190 in line 192, which feeds to the reaction zone 110 via second reaction zone inlet 113. The catalyst system feed line 152 feeds directly to the reaction zone 110 via first reaction zone inlet 111 without any combination with other streams or dilution. For Example 2, the control valve 130 shown in FIG. 2 was a pair of control valves placed in parallel flow, with the second valve of the two control valves being used only upon plugging of the first control valve, if plugging were to occur. That is, the second of the two control valves was used as a backup to the first of the two control valves so as to keep the experiment running, if needed.

Prior to startup, the reactor was pressure tested with nitrogen and purged to ensure that no residual air or moisture was present in the reactor.

For startup, the organic reaction medium (anhydrous cyclohexane) was pumped using pump 180 from the organic reaction medium source 160 to the reaction zone 110 via line 162, pump 180, line 191, mixing device 190, and line 192. Once flow of the organic reaction medium was established, the pressure of the reaction zone 110 was adjusted to 900 psig (6.21 MPag), and the temperature of the autoclave reactor was increased to 70° C. After the pressure and temperature were reached, hydrogen flow at 24 sccm was initiated via line 144, line 142, line 191, mixing device 190, and line 192, and 15.7 mL of the catalyst system was charged to the reactor via line 152. Catalyst system flow rate in line 152 was then set to 15.7 mL/h for 30 minutes. After 30 minutes, ethylene was fed at 50 g/h to the reaction zone 110 via line 142, line 191, mixing device 190, and line 192. Every 15 minutes, the ethylene flow rate was increased by 50 g/h until 200 g/h was reached. The first of the two control valves plugged at 165 minutes. The run was terminated at 285 minutes due to plugging/fouling of the autoclave reactor and complete consumption of the runs catalyst system mixture. During the run reaction zone effluent samples were periodically removed via a sample port located on the reaction zone effluent line 118. After run completion, the reactor was disassembled, the polymer recovered and weighed. The amount of polymer recovered from the reactor is reported in Table 5 along with additional ethylene oligomerization run data.

Example 3

In Example 3, the oligomerization of ethylene was performed, using 1-hexene as the $C_{3+}$ olefin during the reaction zone startup.

A 300 cc autoclave reactor having the configuration shown in FIG. 2 was used. The catalyst system feed line 152 was fed directly to the reaction zone 110, and ethylene and hydrogen were combined with the organic reaction medium feed line 162 to yield a feedstock mixture in line 191. In Example 3, 1-hexene flowed through line 146, line 147a, line 142, line 191, mixing device 190 (which was a static mixer), and line 192 to the reaction zone 110. For Example 3, the control valve 130 shown in FIG. 2 was a pair of control valves placed in parallel flow, with the second valve of the two control valves being used only upon plugging of the first control valve, if plugging were to occur. That is, the second of the two control valves was used as a backup to the first of the two control valves so as to keep the experiment running, if needed.

Prior to startup, the reactor was pressure tested with nitrogen and purged to ensure that no residual air or moisture was present in the reactor.

For startup, the organic reaction medium (anhydrous cyclohexane) was pumped using pump 180 from the organic reaction medium source 160 to the reaction zone 110 via line 162, line 191, mixing device 190, and line 192. Once flow of the organic reaction medium was established, the pressure of the reaction zone 110 was adjusted to 900 psig (6.21 MPag), and the temperature of the autoclave reactor was increased to 70° C. After the pressure and temperature were reached, hydrogen flow at 24 sccm was initiated via line 144, line 142, line 191, mixing device 190, and line 192, and 15.7 mL of the catalyst system was charged to the reactor via line 152. Catalyst system flow rate was then set to 15.7 mL/h for 30 minutes. After 30 minutes of catalyst flow, 1-hexene flow was initiated at 200 g/hour via line 146, line 147a, line 142, line 191, mixing device 190 (which was a static mixer), and line 192. After 15 minutes, the 1-hexene flow rate was reduced by 50 g/hour and the ethylene flow was initiated at 50 g/hour via line 142, line 191, mixing device 190, and line 192. Thereafter, every 15 minutes the 1-hexene flow rate was reduced by 50 g/hour and the ethylene flow rate was increased by 50 g/hour until the 1-hexene flow rate became zero and the ethylene flow rate became 200 g/hour, which was achieved one hour after initiating the 1-hexene flow. The ethylene oligomerization was continued until the complete consumption of the catalyst system mixture at 345 minutes. During the run reaction zone effluent samples were periodically removed via a sample port located on the reaction zone effluent line 118. After run completion, the reactor was disassembled, the polymer recovered and weighed.

Figure 4:
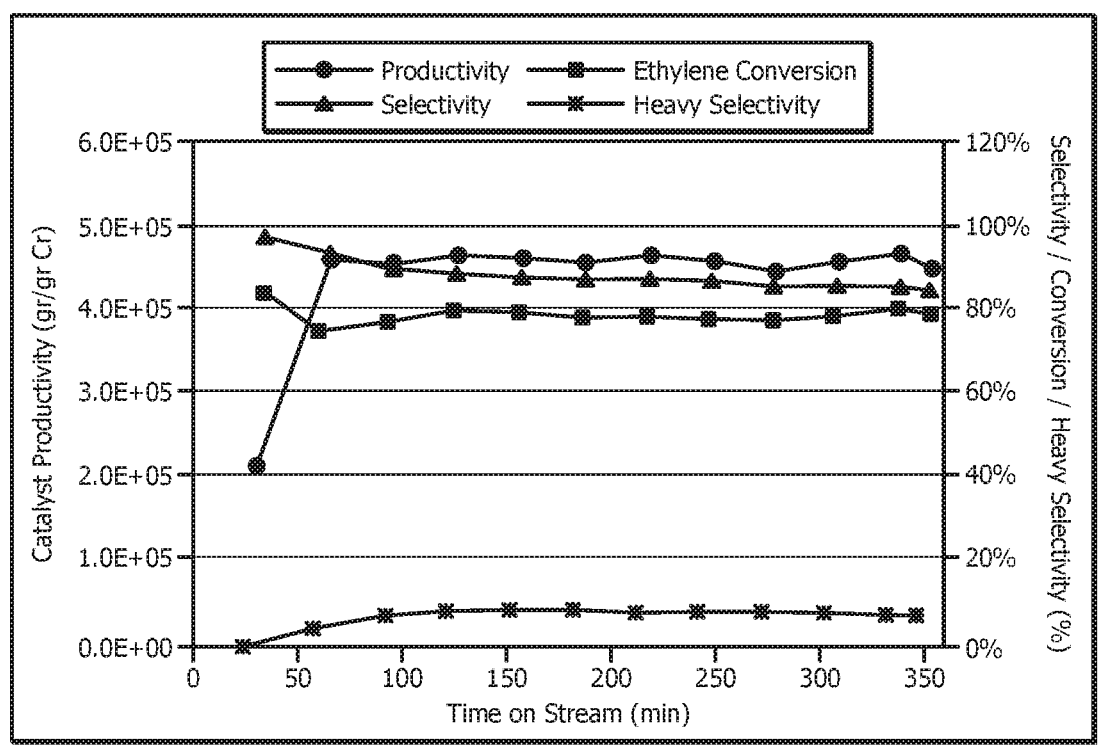
FIG. 4 shows a graph of catalyst productivity, selectivity, conversion, and heavy selectivity versus time for Example 3.

Performance metrics for Example 3 are shown in FIG. 4. As can be seen, after about 50 minutes of time on stream, the catalyst productivity reached above 450,000 g NAO/g Cr and remained at this level for the remainder of the run. FIG. 4 also shows selectivity, ethylene conversion, and heavy selectivity.

The amount of polymer recovered from the reactor is reported in Table 5 along with additional ethylene oligomerization run data.

TABLE 5

| | Example 1 (comparative) | Example 2 (comparative) | Example 3 |
|---|---|---|---|
| Run Length (min) | 307 | 285 | 345 |
| Operating Time at Steady State | 180 | 150 | 285 |
| Total 1-hexene and 1-octene Produced (g) | 675 | 585 | 668 |
| Recovered Polymer (g) | 6.377 | 2.708 | 0.559 |
| g Polymer/g 1-hexene and 1-octene | 0.0094 | 0.0046 | 0.0008 |
| Polymer Formation Rate (g Polyethylene/minute) | 0.0208 | 0.0095 | 0.0016 |
| Reasons for Termination | Plugged Reactor and Plugged Control Valves | One Plugged Control Valve at End of Run | End of Run |

As can be seen in Table 5, Example 3 provided improved operating time without pugging, reduced polymer production, polymer ratio, and polymer formation rate. Compared with Examples 1 and 2, Example 3 has a much longer time at steady state (285 minutes compared to 180 min and 150 min). Moreover, the autoclave reactor and none of the control valves in Example 3 plugged with polymer, while control valves and the reactor plugged in Example 1 and a control valve plugged in Example 2. While it can be noted that the total $C_6$ and $C_8$ produced in Example 3 was comparable to Examples 1 and 2, the run in Example 3 could have run longer since the control valves and the reactor had not plugged. When comparing Example 1 to Example 2, it appears that lowering the maximum ethylene flow rate from 250 g/h in Example 1 to 200 g/h in Example 2 provided less plugging in that only one control value had plugged in Example 2.

Surprisingly and unexpectedly, the amount of polyethylene recovered in Example 3 (0.0008 g) was over 11 times less than the amount of polyethylene recovered from comparative Example 1 (6.377 g) and almost 5 times less than the amount of polyethylene recovered from comparative Example 2 (2.708 g). Additionally, the polymer to $C_6$ and $C_8$ ratio for comparative Example 1 is a magnitude greater than that of Example 3, and the solids ratio for comparative Example 2 is over 5 times greater than Example 3. Moreover, the solids formation rate for Example 3 is much less than for Examples 1 and 2.

The run of comparative Example 1 terminated because of the plugged reactor and two reactor control valves. Although comparative Example 2 terminated because of end of run conditions, one control valve had plugged and it was expected that other control valves would have eventually plugged if the run had continued. In fact, after reactor disassembly in Example 2, it was observed that additional valve were close to plugging when the ethylene oligomerization run was terminated. In contrast, Example 3 exhibited excellent ethylene oligomerization run stability and could have continued for many more hours since upon reactor disassembly it was observed that no reactor control values were close to plugging.

In summary, the surprising and unexpected results of the disclosed systems and processes include:

i) between 5 and 11 times reduction in polyethylene recovered from the reactor in Example 3 versus the polyethylene recovered from the reactor in Example 1 and Example 2;

ii) improved run stability for Example 3 compared to Example 1 and Example 2;

iii) an order of magnitude reduction in the solids ratio when comparing Example 3 with Example 1, and significant reduction in solids ratio when comparing Example 3 with Example 2; and iv) the oligomerization reaction in Example 3 was only terminated due to end of run with no plugging of any equipment.

While Example 3 utilized the configuration of system 200 shown in FIG. 2, it is expected, without being limited to theory, that the configuration of system 100 in FIG. 1, system 300 of FIG. 3, and other similar methods of initiating ethylene oligomerization in a reaction zone in the presence of a $C_3$ olefin would perform similarly because any ethylene is still contacted with the catalyst system in the presence of $C_{3+}$ olefin at reaction conditions-even though no feedstock mixture is utilized in FIG. 1 and the contact between ethylene and the catalyst system in FIG. 3 is outside the reaction zone 110. Thus, it is expected that system 100 and system 300 would have the same surprising and unexpected results as system 200.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference.

Embodiment 1

A process comprising: a) introducing into a reaction zone containing a $C_{3+}$ olefin (any disclosed herein) and optionally an organic reaction medium (any disclosed herein) wherein the reaction zone is substantially devoid of ethylene; i) ethylene ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iii) the organic reaction medium, and iv) optionally hydrogen; and b) forming an ethylene oligomer product in the reaction zone; wherein the $C_{3+}$ olefin is not an ethylene oligomer formed in-situ within the reaction zone.

Embodiment 2

A process comprising: a) contacting in a reaction zone i) a $C_{3+}$ olefin (e.g., any disclosed herein), ii) ethylene, iii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iv) an organic reaction medium (any disclosed herein), and v) optionally hydrogen into the reaction zone; and c) forming an ethylene oligomer product; wherein the $C_{3+}$ olefin is not an ethylene oligomer formed in-situ within the reaction zone.

Embodiment 3

A process comprising: a) contacting i) ethylene, ii) a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), iii) an organic reaction medium (any described herein), and iv) optionally hydrogen in a reaction zone; b) forming an ethylene oligomer product in the reaction zone; wherein ethylene, the catalyst system, and the organic reaction medium are introduced into the reaction zone and for a period of time a $C_{3+}$ olefin is introduced into the reaction zone.

Embodiment 4

The process of embodiment 2 or 3, wherein ethylene, the organic reaction medium, and for the period of time the $C_{3+}$ olefin are separately introduced into the reaction zone.

Embodiment 5

The process of embodiment 2 or 3, wherein ethylene and at least a portion of the organic reaction medium are contacted to form a feedstock mixture prior to the ethylene contacting the catalyst system and the feedstock mixture and for the period of time the $C_{3+}$ olefin are separately introduced to the reaction zone.

Embodiment 6

The process of embodiment 4 or 5, further comprising introducing the $C_{3+}$ olefin to the reaction zone prior to introducing the ethylene, the catalyst system, or both the ethylene and the catalyst system to the reaction zone.

Embodiment 7

The process of embodiment 2 or 3, wherein ethylene, at least a portion of the organic reaction medium, and for the period of time the $C_{3+}$ olefin are contacted to form a feedstock mixture prior to the ethylene contacting the catalyst system.

Embodiment 8

A process comprising: a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); b) for a period of time separately feeding to the reaction zone a feedstock mixture comprising ethylene and i) a $C_{3+}$ olefin (e.g., any described herein), and ii) at least a portion of an organic reaction medium (e.g., any described herein), or iii) combinations of i) and ii); wherein the feedstock mixture is substantially free of the catalyst system; c) contacting the catalyst system and the feedstock mixture in the reaction zone; and d) forming an ethylene oligomer product in the reaction zone.

Embodiment 9

A process comprising: a) contacting i) ethylene, ii) at least a portion of an organic reaction medium (e.g., any disclosed herein), and iii) for a period of time a $C_{3+}$ olefin (e.g., any disclosed herein) to form a feedstock mixture; b) subsequent to a), contacting in a reaction zone the feedstock mixture with a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) forming an ethylene oligomer product in the reaction zone.

Embodiment 10

A process comprising: a) diluting ethylene by addition of at least i) a portion of an organic reaction medium (any described herein), ii) for a period of time a $C_{3+}$ olefin (e.g., any described herein), or iii) for a period of time at least a portion of an organic reaction medium (any described herein) and a $C_{3+}$ olefin to form a feedstock mixture prior to contacting the ethylene with a catalyst system in a reaction zone; b) contacting in the reaction zone the feedstock mixture and the catalyst system, wherein the catalyst system comprises i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) forming an ethylene oligomer product in the reaction zone.

Embodiment 11

A system comprising: a) a feedstock mixture comprising ethylene, an organic reaction medium (e.g., any described herein), and for a period of time a $C_{3+}$ olefin (e.g., any described herein); b) a catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); and c) a reaction zone receiving the feedstock mixture separately from the catalyst stream.

Embodiment 12

The system of embodiment 11, further comprising a reaction zone effluent line comprising an ethylene oligomer product formed in the reaction zone.

Embodiment 13

The subject matter of any one of embodiments 7-11, wherein for the period of time the $C_{3+}$ olefin is dispersed in the feedstock mixture prior to introducing/feeding the feedstock mixture into the reaction zone.

Embodiment 14

The subject matter of any one of embodiments 5-13, wherein ethylene is dispersed within the feedstock mixture prior to ethylene contacting the catalyst system.

Embodiment 15

The subject matter of any one of embodiments 5-14, wherein ethylene is dispersed with the organic reaction medium prior to introduction of the feedstock mixture into the reaction zone.

Embodiment 16

The subject matter of any one of embodiments 5-14, wherein the period of time occurs during a reaction zone startup.

Embodiment 17

A process comprising: a) feeding a catalyst system to a reaction zone, the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane (any disclosed herein); b) separately feeding to the reaction zone a feedstock mixture comprising i) ethylene, ii) an organic reaction medium (e.g., any described herein), and iii) for a period of time a $C_3$ olefin (e.g., any described herein) to contact the catalyst system; wherein during a reaction zone startup the feedstock mixture $C_{3+}$ olefin:ethylene weight ratio periodically or continuously decreases; c) forming an ethylene oligomer product in the reaction zone; and d) operating the reaction zone in about steady-state conditions subsequent to the reaction zone start-up; wherein the feedstock mixture comprising i) ethylene, ii) a $C_{3+}$ olefin, and iii) an organic reaction medium is fed to the reaction zone for a period of time.

Embodiment 18

A process for startup of a reaction zone, the process comprising: contacting in the reaction zone 1) ethylene, 2) a catalyst system comprising a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and b) an aluminoxane (any disclosed herein), 3) an organic reaction medium, and 4) optionally hydrogen to form an ethylene oligomer product; wherein: the catalyst system is fed to the reaction zone, a feedstock mixture comprising i) ethylene, ii) an organic reaction medium (any described herein), and iii) for a period of time a $C_{3+}$ olefin (any described herein) is fed to the reaction zone, wherein the feedstock mixture is substantially free of the catalyst system prior to the feedstock mixture contacting the catalyst system in the reaction zone.

Embodiment 19

The process of embodiment 17 or 18, wherein for the period of time the $C_{3+}$ olefin is dispersed in the feedstock mixture prior to introducing/feeding the feedstock mixture into the reaction zone.

Embodiment 20

The process of any one of embodiments 17-19, wherein ethylene is dispersed within the feedstock mixture prior to ethylene contacting the catalyst system.

Embodiment 21

The subject matter of any one of embodiments 5-20, wherein the period of time begins at a point when the reaction zone is not producing the ethylene oligomer product.

Embodiment 22

The subject matter of any one of embodiments 5-21, wherein over a $C_{3+}$ olefin/ethylene feed period of time a $C_{3+}$ olefin:ethylene weight ratio fed/introduced to the reaction zone decreases from a value of at least 0.5:1 (or any other at least value disclosed herein) to a value less than 0.2:1 (or any other less than value disclosed herein).

Embodiment 23

The subject matter of any one of embodiments 5-22, wherein the $C_{3+}$ olefin:ethylene weight ratio has an initial value of about 1:0.

Embodiment 24

The subject matter of any one of embodiments 5-23, wherein the $C_{3+}$ olefin:ethylene weight ratio decreases to a value of about 0:1.

Embodiment 25

The subject matter of any one of embodiments 1-24, wherein over a reaction zone period of time the reaction zone has a $C_{3+}$ olefin to ethylene zone weight ratio that decreases from a value of at least 0.5:1 (or any other reaction zone at least value disclosed herein) to a value less than 0.2:1 (or any other reaction zone less than value disclosed herein), wherein the $C_{3+}$ olefin in the reaction zone and the $C_{3+}$ olefin of the $C_{3+}$ olefin:ethylene weight ratio is not an ethylene oligomer formed in-situ within the reaction zone.

Embodiment 26

The subject matter of any one of embodiments 1-25, further comprising contacting the $C_{3+}$ olefin with the catalyst system prior to introducing (or feeding) the $C_{3+}$ olefin and the catalyst system to the reaction zone.

Embodiment 27

The subject matter of any one of embodiments 1-26, wherein substantially no $C_{3+}$ olefin is introduced or fed to the reaction zone after the period of time, wherein the period of time is a reaction zone period of time or a $C_{3+}$ olefin/ethylene feed period of time.

Embodiment 28

The subject matter of any one of embodiments 1-27, wherein the reaction zone is operated under steady-state conditions after the period of time (or subsequent to the reaction zone start-up period), wherein the period of time is a reaction zone period of time or a $C_{3+}$ olefin/ethylene feed period of time.

Embodiment 29

The subject matter of any one of embodiments 1-27, wherein the contacting of ethylene and the organic reaction medium to form the feedstock mixture occurs subsequently, but not exclusively, after the period of time (or after reaction zone startup), wherein the period of time is a reaction zone period of time or a $C_{3+}$ olefin/ethylene feed period of time.

Embodiment 30

The subject matter of any one of embodiments 27-29, wherein substantially all of the ethylene is introduced to the reaction zone via the feedstock mixture.

Embodiment 31

The subject matter of any one of embodiments 27-30, wherein the catalyst system is introduced into the reaction zone separately from feedstock mixture.

Embodiment 32

The subject matter of any one of embodiments 1-31, wherein the at least a portion of the organic reaction medium is contacted with an alkylaluminum compound prior to introduction of the at least a portion of the organic reaction medium to the reaction zone.

Embodiment 33

The subject matter of any one of embodiments 1-32, wherein the at least a portion of the organic reaction medium is contacted with an alkylaluminum compound prior to contact of ethylene with the at least a portion of the organic reaction medium.

Embodiment 34

The subject matter of any one of embodiments 1-33, wherein the catalyst system mixture comprises a diluent.

Embodiment 35

The subject matter of embodiment 34, wherein the diluent comprises the organic reaction medium.

Embodiment 36

The subject matter of any one of embodiments 1-35, wherein a reaction zone effluent comprising the ethylene oligomer product is removed from the reaction zone.

Embodiment 37

The subject matter of any one of embodiments 1-36, wherein hexenes and/or or octenes are separated from the reaction zone effluent.

Embodiment 38

The subject matter of any one of embodiments 1-37, wherein the feedstock mixture, the catalyst system, and optionally, hydrogen are periodically or continuously introduced into the reaction zone and a reaction zone effluent comprising the ethylene oligomer product is periodically or continuously removed from the reaction zone.

Embodiment 39

The subject matter of any one of embodiments 1-38, wherein a mass of polymer per mass of oligomer in the reaction zone is less than the mass of polymer per mass of oligomer in the reaction zone in an otherwise similar process or system where a $C_{3+}$ olefin:ethylene weight ratio does not decrease over the period of time.

Embodiment 40

The subject matter of any one of embodiments 1-39, wherein a mass of polymer per mass of oligomer in the reaction zone is less than the mass of polymer per mass of oligomer in the reaction zone in an otherwise similar process or system which does not: i) contact ethylene with the at least a portion of the organic reaction medium prior to contact of ethylene with the catalyst system, or ii) introduce or feed the feedstock mixture into the reaction zone separately from the catalyst system.

Embodiment 41

The subject matter of any one of embodiments 1-40, having a productivity higher than a productivity in an otherwise similar process or system where the reaction zone $C_{3+}$ olefin:ethylene weight ratio does not decrease over the period of time.

Embodiment 42

The subject matter of any one of embodiments 1-41, having a productivity higher than a productivity in an otherwise similar process or system which does not: i) contact ethylene with the at least a portion of the organic reaction medium prior to contact of ethylene with the catalyst system, or ii) introduce or feed the feedstock mixture into the reaction zone separately from the catalyst system.

Embodiment 43

A reaction system comprising: a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein) to the reaction zone; a second reaction zone inlet configured to introduce ethylene, an organic reaction medium, and optionally hydrogen to the reaction zone; a $C_{3+}$ olefin feed line in fluid communication with the first reaction zone inlet, the second reaction zone inlet, or a third reaction zone inlet configured to introduce a $C_{3+}$ olefin to the reaction zone; and one or more reaction zone outlets configured to discharge the reaction zone effluent comprising an ethylene oligomer product from the reaction zone.

Embodiment 44

The reaction system of embodiment 43, further comprising: a catalyst system feed line flowing the catalyst system to the first reaction zone inlet; an ethylene feed line comprising the ethylene; an organic reaction medium feed line comprising the organic reaction medium, wherein the organic reaction medium feed line and the ethylene feed line combine to yield the feedstock mixture which is introduced to the reaction zone via the second reaction zone inlet, wherein the $C_{3+}$ olefin feed line combines with at least one of the catalyst system feed line, the ethylene feed line, the organic reaction medium feed line, the feedstock mixture feed line, or a dispersed feedstock mixture feed line formed by passing the feedstock mixture through a mixing device prior to flowing to the reaction zone via the second reaction zone inlet.

Embodiment 45

The reaction system of embodiment 43 or 44, further comprising: a pump in fluid communication with the second reaction zone inlet and which is located upstream of a point where the ethylene feed line and the organic reaction medium feed line join to produce the feedstock mixture; and a mixing device positioned between i) the joining of the ethylene feed line and the organic reaction medium feed line and ii) the second reaction zone inlet to disperse the ethylene and the organic reaction medium prior to the feedstock mixture entering the reaction zone.

Embodiment 46

The reaction system of any one of embodiments 43-45, wherein during steady state operation, the first reaction zone inlet is configured to periodically or continuously introduce the catalyst system to the reaction zone, the second reaction zone inlet is configured to periodically or continuously introduced the feedstock mixture to the reaction zone, and the one or more reaction zone outlets are configured to periodically or continuously discharge the reaction zone effluent from the reaction zone.

Embodiment 47

A reaction system comprising: a reaction zone; a reaction zone inlet configured to introduce a catalyst system, ethylene, an organic reaction medium, and a $C_{3+}$ olefin to the reaction zone; an ethylene feed line comprising ethylene, a $C_{3+}$ olefin feed line comprising a $C_{3+}$ olefin, an organic reaction medium feed line comprising an organic reaction medium and optionally a hydrogen feedline comprising hydrogen all in fluid communication with the reaction zone inlet, wherein the organic reaction medium feed line combines with the ethylene feed line to form a feedstock mixture feed line in fluid communication with the reaction zone inlet; a catalyst system feed line comprising the catalyst system in fluid communication with the reaction zone inlet, wherein the catalyst system feed line combines with the ethylene feed line, the organic reaction medium feed line, the feedstock mixture feed line, or a dispersed feedstock mixture feed line formed by passing the feedstock mixture feed line through a mixing device; one or more reaction zone outlets configured to discharge the reaction zone effluent comprising an ethylene oligomer product from the reaction zone, wherein the catalyst system comprises (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein), and wherein the $C_{3+}$ olefin feed line joins with one or more of the ethylene feed line, the organic reaction medium feed line, the feedstock mixture feed line, the dispersed feedstock mixture feed line, or a combined feed line formed by joining the catalyst system feed line and the dispersed feedstock mixture feed line.

Embodiment 48

The reaction system of embodiment 47, further comprising: a mixing device positioned between i) the joining of the ethylene feed line and the organic reaction medium feed line and ii) the reaction zone inlet to disperse the ethylene and the organic reaction medium prior to the feedstock mixture joining with the catalyst system and entering the reaction zone.

Embodiment 49

The reaction system of any one of embodiments 47-48, wherein the reaction zone inlet is configured to periodically or continuously introduce the catalyst system and the feedstock mixture to the reaction zone, and the one or more reaction zone outlets are configured to periodically or continuously discharge the reaction zone effluent from the reaction zone.

Embodiment 50

A reaction system comprising: a reaction zone; a first reaction zone inlet configured to introduce a catalyst system comprising (a) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and (b) an aluminoxane (any disclosed herein) to the reaction zone; a second reaction zone inlet configured to introduce ethylene and optionally hydrogen to the reaction zone; a third reaction zone inlet configured to introduce an organic reaction medium to the reaction zone; a $C_{3+}$ olefin feed line in fluid communication with one or more of the first reaction zone inlet, the second reaction zone inlet, the third reaction zone inlet, or a fourth reaction zone inlet which is configured to introduce the $C_{3+}$ olefin directly to the reaction zone; and one or more reaction zone outlets configured to discharge the reaction zone effluent comprising an ethylene oligomer product from the reaction zone.

Embodiment 51

The reaction system of embodiment 50, further comprising: a catalyst system feed line flowing the catalyst system to the first reaction zone inlet; an ethylene feed line comprising flowing ethylene to the second reaction zone inlet; and an organic reaction medium feed line flowing the organic reaction medium to the third reaction zone inlet, wherein the $C_{3+}$ olefin feed line i) combines with at least one of the catalyst system feed line, the ethylene feed line, or the organic reaction medium feed line, or ii) flows directly to the fourth reaction zone inlet.

Embodiment 52

The subject matter of any one of embodiments 1-51, wherein the $C_{3+}$ olefin comprises a $C_4$ to $C_{16}$ internal olefin or alpha olefin.

Embodiment 53

The subject matter of any one of embodiments 1-51, wherein the $C_{3+}$ olefin comprises 1-hexene, 1-octene, or 1-hexene and 1-octene.

The inventions illustratively disclosed herein suitably can be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims herein.

What is claimed is:

1. A reaction system comprising:
   a reaction zone configured to form an oligomer product, the reaction zone comprising ethylene, an organic reaction medium, a catalyst system, a $C_3+$ olefin, and optionally hydrogen;
   a first reaction zone inlet configured to introduce the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone;
   a second reaction zone inlet configured to introduce ethylene, the organic reaction medium, and optionally hydrogen to the reaction zone;
   a $C_3+$ olefin feed line in fluid communication with the first reaction zone inlet, the second reaction zone inlet, or a third reaction zone inlet, wherein the $C_3+$ olefin feed line is configured to introduce the $C_3+$ olefin to the reaction zone; and
   one or more reaction zone outlets configured to discharge a reaction zone effluent comprising an ethylene oligomer product from the reaction zone.

2. The reaction system of claim 1, further comprising:
   a catalyst system feed line configured to flow the catalyst system to the first reaction zone inlet.

3. The reaction system of claim 2, wherein the $C_{3+}$ olefin feed line is configured to combine with the catalyst system feed line prior to the $C_{3+}$ olefin flowing to the reaction zone via the first reaction zone inlet.

4. The reaction system of claim 1, further comprising:
an ethylene feed line comprising ethylene and optionally hydrogen, wherein the ethylene feed line is configured to flow ethylene and optionally hydrogen to the reaction zone via the second reaction zone inlet; and
an organic reaction medium feed line comprising the organic reaction medium, wherein the organic reaction medium feed line is configured to flow the organic reaction medium to the reaction zone via the second reaction zone inlet.

5. The reaction system of claim 4, wherein the $C_{3+}$ olefin feed line is configured to combine with the ethylene feed line or the organic reaction medium feed line prior to the $C_{3+}$ olefin flowing to the reaction zone via the second reaction zone inlet.

6. The reaction system of claim 4, wherein the organic reaction medium feed line and the ethylene feed line combine to yield a feedstock mixture that is introduced to the reaction zone via the second reaction zone inlet.

7. The reaction system of claim 6, wherein the $C_{3+}$ olefin feed line is configured to combine with the feedstock mixture prior to the $C_{3+}$ olefin flowing to the reaction zone via the second reaction zone inlet.

8. The reaction system of claim 6, further comprising:
a mixing device configured to disperse the organic reaction medium and ethylene in the feedstock mixture before the feedstock mixture flows to the reaction zone via the second reaction zone inlet; and
a pump in fluid communication with the second reaction zone inlet, wherein the pump is located upstream of a point where the ethylene feed line and the organic reaction medium feed line combine to yield the feedstock mixture.

9. The reaction system of claim 8, wherein the $C_{3+}$ olefin feed line is configured to combine with the feedstock mixture at a location between the mixing device and the second reaction zone inlet.

10. The reaction system of claim 6, wherein during steady state operation, the first reaction zone inlet is configured to periodically or continuously introduce the catalyst system to the reaction zone, the second reaction zone inlet is configured to periodically or continuously introduced the feedstock mixture to the reaction zone, and the one or more reaction zone outlets are configured to periodically or continuously discharge the reaction zone effluent from the reaction zone.

11. The reaction system of claim 1, wherein the $C_{3+}$ olefin comprises hexene, 1-octene, or a combination thereof; and wherein the ethylene oligomer product comprises hexenes and/or octenes.

12. The reaction system of claim 1, wherein the reaction zone has a $C_3+$ olefin:ethylene weight ratio that decreases from a value of equal to or greater than 0.5:1 to a value less than 0.2:1 over a period of time, wherein the $C_3+$ olefin in the reaction zone that is used to determine the $C_3$, olefin:ethylene weight ratio in the reaction zone is not an ethylene oligomer formed in-situ within the reaction zone.

13. A reaction system comprising:
a reaction zone configured to form an oligomer product, the reaction zone comprising ethylene, an organic reaction medium, a catalyst system, a $C_3+$ olefin, and optionally hydrogen;
a first reaction zone inlet configured to introduce the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone;
a second reaction zone inlet configured to introduce ethylene and optionally hydrogen to the reaction zone;
a third reaction zone inlet configured to introduce the organic reaction medium to the reaction zone;
a $C_3+$ olefin feed line in fluid communication with the first reaction zone inlet, the second reaction zone inlet, the third reaction zone inlet, or a fourth reaction zone inlet wherein the $C_3+$ olefin feed line is configured to introduce the $C_3+$ olefin to the reaction zone; and
one or more reaction zone outlets configured to discharge a reaction zone effluent comprising an ethylene oligomer product from the reaction zone.

14. The reaction system of claim 13, further comprising:
a catalyst system feed line configured to flow the catalyst system to the first reaction zone inlet, wherein the $C_{3+}$ olefin feed line is configured to combine with the catalyst system feed line prior to the $C_{3+}$ olefin flowing to the reaction zone via the first reaction zone inlet;
an ethylene feed line comprising the ethylene and optionally hydrogen, wherein the ethylene feed line is configured to flow ethylene and optionally hydrogen to the reaction zone via the second reaction zone inlet, wherein the $C_{3+}$ olefin feed line is configured to combine with the ethylene feed line prior to the $C_{3+}$ olefin flowing to the reaction zone via the second reaction zone inlet; or
an organic reaction medium feed line comprising the organic reaction medium and configured to flow the organic reaction medium to the reaction zone via the third reaction zone inlet, wherein the $C_{3+}$ olefin feed line is configured to combine with the organic reaction medium feed line prior to the $C_{3+}$ olefin flowing to the reaction zone via the third reaction zone inlet.

15. The reaction system of claim 13, wherein the reaction zone has a $C_3+$ olefin:ethylene weight ratio that decreases from a value of equal to or greater than 0.5:1 to a value less than 0.2:1 over a period of time, wherein the $C_3+$ olefin in the reaction zone that is used to determine the $C_3$, olefin:ethylene weight ratio in the reaction zone is not an ethylene oligomer formed in-situ within the reaction zone.

16. A reaction system comprising:
a reaction zone configured to form an oligomer product, the reaction zone comprising ethylene, an organic reaction medium, a catalyst system, a $C_3+$ olefin, and optionally hydrogen;
a first reaction zone inlet configured to introduce ethylene, the organic reaction medium, optionally hydrogen, and the catalyst system comprising i) a chromium component comprising an $N^2$-phosphinyl amidine chromium compound complex, an $N^2$-phosphinyl formamidine chromium compound complex, an $N^2$-phosphinyl guanidine chromium compound complex, or any combination thereof, and ii) an aluminoxane to the reaction zone;
a $C_3+$ olefin feed line in fluid communication with the first reaction zone inlet or a second reaction zone inlet, wherein the $C_3+$ olefin feed line is configured to introduce the $C_3+$ olefin to the reaction zone; and
one or more reaction zone outlets configured to discharge a reaction zone effluent comprising an ethylene oligomer product from the reaction zone.

17. The reaction system of claim 16, further comprising:
an ethylene feed line comprising ethylene and optionally hydrogen, wherein the ethylene feed line is configured to flow ethylene and optionally hydrogen to the reaction zone via the first reaction zone inlet;
an organic reaction medium feed line comprising the organic reaction medium, wherein the organic reaction medium feed line is configured to flow the organic reaction medium to the reaction zone via the first reaction zone inlet; and
a catalyst system feed line configured to flow the catalyst system to reaction zone via the first reaction zone inlet.

18. The reaction system of claim 17, wherein the $C_{3+}$ olefin feed line is configured to combine with the ethylene feed line, the organic reaction medium feed line, or the catalyst system feed line prior to the $C_{3+}$ olefin flowing to the reaction zone via the first reaction zone inlet.

19. The reaction system of claim 17, wherein the organic reaction medium feed line and the ethylene feed line combine to yield a feedstock mixture that is introduced to the reaction zone via the first reaction zone inlet.

20. The reaction system of claim 19, wherein the $C_{3+}$ olefin feed line is configured to combine with the feedstock mixture prior to the $C_{3+}$ olefin flowing to the reaction zone via the second reaction zone inlet.

21. The reaction system of claim 19, further comprising:
a mixing device configured to disperse the organic reaction medium and ethylene in the feedstock mixture before the feedstock mixture flows to the reaction zone via the first reaction zone inlet.

22. The reaction system of claim 21, wherein the $C_{3+}$ olefin feed line is configured to combine with the feedstock mixture at a location between the mixing device and the first reaction zone inlet.

23. The reaction system of claim 21, wherein the catalyst system feed line is configured to combine with the feedstock mixture downstream of the mixing device.

24. The reaction system of claim 23, wherein the $C_{3+}$ olefin feed line is configured to combine with the feedstock mixture at a location between the mixing device and the point where the catalyst system feed line combines with the feedstock mixture.

25. The reaction system of claim 23, wherein the $C_{3+}$ olefin feed line is configured to combine with the feedstock mixture at a location between the point where the catalyst system feed line combines with the feedstock mixture and the first reaction zone inlet.

26. The reaction system of claim 16, wherein the reaction zone has a $C_3+$ olefin:ethylene weight ratio that decreases from a value of equal to or greater than 0.5:1 to a value less than 0.2:1 over a period of time, wherein the $C_3+$ olefin in the reaction zone that is used to determine the $C_3$, olefin:ethylene weight ratio in the reaction zone is not an ethylene oligomer formed in-situ within the reaction zone.

* * * * *